(12) United States Patent
Koga et al.

(10) Patent No.: US 8,598,328 B2
(45) Date of Patent: Dec. 3, 2013

(54) TOL1 FACTOR TRANSPOSASE AND DNA INTRODUCTION SYSTEM USING THE SAME

(75) Inventors: Akihiko Koga, Nagoya (JP); Satoshi Hamaguchi, Niigata (JP)

(73) Assignees: National University Corporation Nagoya University, Nagoya-shi (JP); Niigata University, Niigata-shi (JP)

(*) Notice: Subject to any disclaimer, the term of this patent is extended or adjusted under 35 U.S.C. 154(b) by 740 days.

(21) Appl. No.: 12/518,967

(22) PCT Filed: Dec. 6, 2007

(86) PCT No.: PCT/JP2007/073565
§ 371 (c)(1),
(2), (4) Date: Jan. 5, 2010

(87) PCT Pub. No.: WO2008/072540
PCT Pub. Date: Jun. 19, 2008

(65) Prior Publication Data
US 2010/0129914 A1  May 27, 2010

(30) Foreign Application Priority Data

Dec. 13, 2006 (JP) ................ 2006-335786
Sep. 28, 2007 (JP) ................ 2007-253321

(51) Int. Cl.
*C12N 15/09* (2006.01)
*C12N 15/12* (2006.01)
*C07H 21/04* (2006.01)

(52) U.S. Cl.
USPC ....... 536/23.2; 435/455; 435/473; 435/320.1; 536/23.1

(58) Field of Classification Search
None
See application file for complete search history.

(56) References Cited

U.S. PATENT DOCUMENTS

2011/0045532 A1* 2/2011 Kawakami et al. .......... 435/69.1

FOREIGN PATENT DOCUMENTS

JP      2001-218588 A    8/2001
WO    WO-03/100070 A2   12/2003

OTHER PUBLICATIONS

Koga et al, The Tol1 transposable element of the medaka fish moves in human and mouse cells, J Hum Genet (2007) 52:628-635.*
Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Richard, Protein stability: still an unsolved problem (1997) Cell Mol. Life Sci. 53:790-80.*
Koga, A. et al., "Transposable Elements in Medaka Fish," Zoological Science 19, 2002, pp. 1-6.
Koga, A. et al., "Insertion of a novel transposable element in the tyrosinase gene is responsible for an albino mutation in the medaka fish, *oryzias latipes*," Mol Gen Genet 249, 1995, pp. 400-405.
Tsutsumi, M. et al.,"Color reversion of the albino medaka fish associated with spontaneous somatic excision of the *Tol-1* transposable element from the tyrosinase gene," Pigment Cell Res. 19, 2006, pp. 243-247.
Koga, A. et al., "Gene transfer and Cloning of Flanking Chromosomal Regions Using the Medaka Fish *Tol2* Transposable Element," Mar Biotechnol 4, 2002, pp. 6-11.
Hamlet, M. R. J. et al., "*Tol2* Transposon-Mediated Transgenesis in *Xenopus tropicalis*," Genesis 44, 2006, pp. 438-445.
Choo, B. G. et al., "Zebrafish transgenic Enhancer TRAP line database (ZETRAP)," BMC Dev Biol 6:5, 2006, pp. 1-7.
Ivics, Z. et al., "Molecular Reconstruction of Sleeping Beauty a *Tc1*-like Transposon form Fish, and Its Transposition in Human Cells," Cell 91, 1997, pp. 501-510.
Miskey, C. et al, "The Frog Prince: a reconstructed transposon from *Rana pipiens* with high transpositional activity in vertebrate cells," Nucleic Acids Research 31, 2003, pp. 6873-6881.
Wu, S. C-Y. et al., "*piggyBac* is a flexible and highly active transposon as compared to Sleeping Beauty, *Tol2*, and *Mos1* in mammalian cells," PNAS 103, 2006, pp. 15008-15013.
Koga, a. et al., "The *Tol1* Transposable element of the medaka fish moves in human and mouse cells," J Hum Genet 52, 2007, pp. 628-635.

* cited by examiner

*Primary Examiner* — Maria Marvich
(74) *Attorney, Agent, or Firm* — Edwards Wildman Palmer LLP; James E. Armstrong, IV; Kellie K. DiNapoli

(57) ABSTRACT

An object is to provide a Tol1 element transposase and a use thereof. Provided is a Tol1 element transposase containing (a) a protein having the amino acid sequence of SEQ ID No: 1 or (b) a protein having an amino acid sequence homologous to the amino acid sequence of SEQ ID NO: 1 and having an enzymatic activity for transferring Tol1 element. Further, provided are a polynucleotide encoding the transposase and an expression construct containing the polynucleotide therein. The present invention also provides a DNA introduction system including (a) a donor factor having such a structure that a desired DNA is inserted in a transposase gene-defected Tol1 element and (b) a helper factor containing the transposase or the polynucleotide.

10 Claims, 30 Drawing Sheets

| Donor plasmid | TSD | Tol1 | TSD | |
|---|---|---|---|---|
| CTTGCATGGTCT | CCTTTAGC | CAGTAGCG----CGCCACTG | CCTTTAGC | AGACATTCACTG |

New insertions:

| | TSD | Tol1 | TSD | |
|---|---|---|---|---|
| AGGGAAACCATT | CCAAACCC | CAGTAGCG----CGCCACTG | CCAAACCC | CATGCTTTAACC |
| GGGTCAGTCTTA | TTCCTTGGG | CAGTAGCG----CGCCACTG | TTCCTTGGG | CAAAGGGAGAAT |
| CTTACGAGAGCG | CTCATACA | CAGTAGCG----CGCCACTG | CTCATACA | GCTCACTTCATA |
| AAGGCATTGGAT | CCCATTAC | CAGTAGCG----CGCCACTG | CCCATTAC | AGATGGTTGTGA |
| CTAGCCTGAAGG | ACCAGGGG | CAGTAGCG----CGCCACTG | ACCAGGGG | CTTGAAAGGTGG |
| GCCTGCTTCTGC | CTCCCGAG | CAGTAGCG----CGCCACTG | CTCCCGAG | TGCTGGGGTCAA |
| ACAACGTCGTGA | CTGGGAAA | CAGTAGCG----CGCCACTG | CTGGGAAA | ACCCTGGCGTTA |
| TGGTTTTTTTCC | CCTGTTTA | CAGTAGCG----CGCCACTG | CCTGTTTA | GGATAGCTTGCT |

```
          10         20         30         40         50         60
TGACGTGAGGACATTTATGCCAAACAAACGCCAAAAACATCTAAAATATGGAGAAAAAAA
                                                       M  E  K  K  R 70         80         90        100        110        120
GGTCAAAGCCATCTGGTGCCCAATTTAGAAAGAAAAGAAAAGAAGAAGAGGAGAAAAGAG
   S  K  P  S  G  A  Q  F  R  K  K  R  K  E  E  E  E  K  R  D 130        140        150        160        170        180
ATAAAGAAAAGGGGGCACTTCTAAGATATTTTGGATCGTCTACCACTGCTCAAGATGAGA
   K  E  K  G  A  L  L  R  Y  F  G  S  S  T  T  A  Q  D  E  T 190        200        210        220        230        240
CATCTACCTCCCTGCCAGCTATCTCATCAGCCACAGTCACAGTCTCACCCCCTCAGGATG
   S  T  S  L  P  A  I  S  S  A  T  V  T  V  S  P  P  Q  D  E 250        260        270        280        290        300
AGCTACCATCTACATCCTCTGCTACTCATGTAGTTCCACAGTTGTTACCTGAGCAAAGTT
   L  P  S  T  S  S  A  T  H  V  V  P  Q  L  L  P  E  Q  S  F 310        320        330        340        350        360
TTGATAGTGAGGCTGAAGACGTTGTTCCATCTACGTCTACCCAGCTTGAGACTTCAGAAA
   D  S  E  A  E  D  V  V  P  S  T  S  T  Q  L  E  T  S  E  M 370        380        390        400        410        420
TGCCTGGTGATGAAACCCCACTGACCCCGACTGCTGAGGACCAGCCTCTACCAACTGACC
   P  G  D  E  T  P  L  T  P  T  A  E  D  Q  P  L  P  T  D  P 430        440        450        460        470        480
CTGCAAAGTGGCCCTCACCTCTGACTGACAGGATACGGATGGAGCTGGTTCGAAGAGGAC
   A  K  W  P  S  P  L  T  D  R  I  R  M  E  L  V  R  R  G  P 490        500        510        520        530        540
CAAGTAGCATACCACCTGACTTTGTTTTCCCAAGAAATGACAGTGATGGGAGAAGTTGTC
   S  S  I  P  P  D  F  V  F  P  R  N  D  S  D  G  R  S  C  H 550        560        570        580        590        600
ATCACCACTATTTCAGGAAGACACTAGTAAGTGGTGAAAAAATAGCAAGAACTTGGTTGA
   H  H  Y  F  R  K  T  L  V  S  G  E  K  I  A  R  T  W  L  M 610        620        630        640        650        660
TGTATTCAAAAGTGAAGAACAGCCTCTTTTGCTTTTGTTGCAAATTGTTTTCCAACAAAA
   Y  S  K  V  K  N  S  L  F  C  F  C  C  K  L  F  S  N  K  N 670        680        690        700        710        720
ACATTAATTTAACAACTTCTGGTACAGCAAACTGGAAACATGCAAGCACATACCTCACAG
   I  N  L  T  T  S  G  T  A  N  W  K  H  A  S  T  Y  L  T  A 730        740        750        760        770        780
CACACGAAAAAAGCCCAGAACACCTCAATTGTATGAAAGCATGGAAGGAACTGTCAGGGA
   H  E  K  S  P  E  H  L  N  C  M  K  A  W  K  E  L  S  G  R 790        800        810        820        830        840
GGATCAGAAGTGGGAAAACAATTGATAAGCAGGAGATGGCACTTCTGGAAGAGGAGCGGG
   I  R  S  G  K  T  I  D  K  Q  E  M  A  L  L  E  E  E  R  V 850        860        870        880        890        900
TGAGATGGAGAGCAGTGCTAACCCGTCTCATTGCTATTGTGCAGTCACTGGCAGTTCGGA
   R  W  R  A  V  L  T  R  L  I  A  I  V  Q  S  L  A  V  R  N 910        920        930        940        950        960
ATTTGGCTCTAAGGGGACACACAGAAACACTGTTCACATCATCAAATGGGAATTTTTTGA
   L  A  L  R  G  H  T  E  T  L  F  T  S  S  N  G  N  F  L  K 970        980        990       1000       1010       1020
AAGAGGTTGAACTGATGGCCAGGTTTGATCCCATAATGAAAGATCATCTTAACCGTGTAT
```

*Fig. 11*

```
                E   V   E   L   M   A   R   F   D   P   I   M   K   D   H   L   N   R   V   L
         1030        1040        1050        1060        1070        1080
TAAGAGGAACAGCAAGTCACAACAGCTACATAGGCCATCATGTGCAGAATGAACTTATTG
  R   G   T   A   S   H   N   S   Y   I   G   H   H   V   Q   N   E   L   I   D 1090        1100        1110        1120        1130        1140
ATTTGTTGAGCAGCAAAATCCTATCCGCTATAGTGGATGACATCAAAAAGGCAAAATATT
  L   L   S   S   K   I   L   S   A   I   V   D   D   I   K   K   A   K   Y   F 1150        1160        1170        1180        1190        1200
TTTCAATAATTCTGGACTGCACTCTGGATATAAGCCACACAGAACAGTTGTCAGTTATAA
  S   I   I   L   D   C   T   L   D   I   S   H   T   E   Q   L   S   V   I   I 1210        1220        1230        1240        1250        1260
TTAGAGTGGTGTCACTGATGGAGAAGCCTCAGATCAGGGAACATTTTATGGGGTTTTTGG
  R   V   V   S   L   M   E   K   P   Q   I   R   E   H   F   M   G   F   L   E 1270        1280        1290        1300        1310        1320
AGGCAGAGGAGTCCACAGGCCAGCACTTGGCATCCATGATCTTAAACAGACTTGAGGAGT
  A   E   E   S   T   G   Q   H   L   A   S   M   I   L   N   R   L   E   E   L 1330        1340        1350        1360        1370        1380
TAGGAATTTCTTTTGAAGACTGCAGAGGACAATCATATGATAATGGGGCAAATATGAAAG
  G   I   S   F   E   D   C   R   G   Q   S   Y   D   N   G   A   N   M   K   G 1390        1400        1410        1420        1430        1440
GCAAAAATAAGGGAGTACAAGCCAGGCTCTTAGAAAAGAATCCCCGTGCTCTGTTTTTGC
  K   N   K   G   V   Q   A   R   L   L   E   K   N   P   R   A   L   F   L   P 1450        1460        1470        1480        1490        1500
CATGCGGTGCACACACATTGAATTTAGTTGTGTGTGATGCTGCTAAGAGATCTGTTGATG
  C   G   A   H   T   L   N   L   V   V   C   D   A   A   K   R   S   V   D   A 1510        1520        1530        1540        1550        1560
CTATGAGCTACTTTGGTGTCCTGCAAAAGCTTTACACTTTATTTTCAGCCTCTGCCCAAC
  M   S   Y   F   G   V   L   Q   K   L   Y   T   L   F   S   A   S   A   Q   R 1570        1580        1590        1600        1610        1620
GATGGGCCATACTGAAGAGTCAGGTGAGCATCACTCTAAAGTCGTGGACAGAAACAAGGT
  W   A   I   L   K   S   Q   V   S   I   T   L   K   S   W   T   E   T   R   W 1630        1640        1650        1660        1670        1680
GGGAGAGCAAAATCAAAAGCATCGAGCCCATGAGGTACCAGGGAGCTGCAGTGAGAGAGG
  E   S   K   I   K   S   I   E   P   M   R   Y   Q   G   A   A   V   R   E   A 1690        1700        1710        1720        1730        1740
CTTTAATAGAAGTGAGAGACAAGACCAAAGACCCAGTTATAAAGGCTGAGGCCCAGTCTT
  L   I   E   V   R   D   K   T   K   D   P   V   I   K   A   E   A   Q   S   L 1750        1760        1770        1780        1790        1800
TGTCTGAAGAGGTAGGGTCGTACCGCTTCAACATCTGCACAGTCGTATGGCATGACATTC
  S   E   E   V   G   S   Y   R   F   N   I   C   T   V   V   W   H   D   I   L 1810        1820        1830        1840        1850        1860
TATCTACAATAAAGCATGTCAGCAAACTCATGCAGTCTCCAAATATGCATGTGGACCTAG
  S   T   I   K   H   V   S   K   L   M   Q   S   P   N   M   H   V   D   L   A 1870        1880        1890        1900        1910        1920
CTGTGAGTCTTTTGAAGAAGACTGAACAAAGTCTCCAGAGCTACAGGGCAAATGGCTTTG
  V   S   L   L   K   K   T   E   Q   S   L   Q   S   Y   R   A   N   G   F   V 1930        1940        1950        1960        1970        1980
TGAATGCACAGATGGCAGCCAAAGAAATGTGCAAGGAAATGAATGTCGAGGCTATTTTGA
  N   A   Q   M   A   A   K   E   M   C   K   E   M   N   V   E   A   I   L   K 1990        2000        2010        2020        2030        2040
AACAAAAAAGAATAAGATCCACAAAGTGCCAATTCTCGTATGAATCACACGATGAGCCTT
  Q   K   R   I   R   S   T   K   C   Q   F   S   Y   E   S   H   D   E   P   F
```

*Fig. 12*

```
      2050       2060       2070       2080       2090       2100
TCAGTGACGCACTTAAAAAGTTGGAGGTTGAATTTTTCAATGTTGTTGTTGATGAAGCCT
  S   D   A   L   K   K   L   E   V   E   F   F   N   V   V   V   D   E   A   L 2110       2120       2130       2140       2150       2160
TGTCAGCCATCGCGGAGAGGTTTTCCACATTGGAAGTTGTACAAAACAGATTTGGGGTTT
  S   A   I   A   E   R   F   S   T   L   E   V   V   Q   N   R   F   G   V   L 2170       2180       2190       2200       2210       2220
TGACCAATTTCCCAAGCCTTGGAGACGAGGAGCTGACGGAGCAATGCGAGGCACTAGGCA
  T   N   F   P   S   L   G   D   E   E   L   T   E   Q   C   E   A   L   G   N 2230       2240       2250       2260       2270       2280
ACATACTCCATTTTGAGAAGAACTGGGATTTGGACAGTAGAGAGCTTGTTCAGGAAATCA
  I   L   H   F   E   K   N   W   D   L   D   S   R   E   L   V   Q   E   I   K 2290       2300       2310       2320       2330       2340
AGAACTTGCCTAACTTACCATCAACGACTCCAAGTCTCCTTGAGCTCATCTCTTTCATGT
  N   L   P   N   L   P   S   T   T   P   S   L   L   E   L   I   S   F   M   S 2350       2360       2370       2380       2390       2400
CTGATAAGGATCTATCAGAAATCTATCCGAACTTTTGGACTGCTCTCAGGATTGCACTCA
  D   K   D   L   S   E   I   Y   P   N   F   W   T   A   L   R   I   A   L   T 2410       2420       2430       2440       2450       2460
CCTTGCCAGTCACTGTGGCTCAAGCAGAGAGGAGCTTTTCAAAACTAAAATTGATCAAGT
  L   P   V   T   V   A   Q   A   E   R   S   F   S   K   L   K   L   I   K   S 2470       2480       2490       2500       2510       2520
CGTACCTGAGGTCAACAATGTCACAGGAGCGACTCACTAACCTTGCCGTTGTTAGCATCA
  Y   L   R   S   T   M   S   Q   E   R   L   T   N   L   A   V   V   S   I   N 2530       2540       2550       2560       2570       2580
ATCACTCAGTAGGGGAGCAGATATCATATGATGATGTTATTGACGAGTTTGCATCAAGAA
  H   S   V   G   E   Q   I   S   Y   D   D   V   I   D   E   F   A   S   R   K 2590       2600       2610       2620       2630       2640
AGGCTAGGAAGGTTAGGTTTTAGTTGGTGTTTTCTGTTATTGTATTGGTGCTGCAGTTAT
  A   R   K   V   R   F   *

2650       2660       2670       2680       2690       2700
ATTTATTTTAGCGTGTCATTTGTGTGATAAAAGGTTTGTGCTTTATAATATTTATTTTAT 2710       2720       2730       2740       2750       2760
ATTATTTATTCAATATTGAGTTTGATTCAATATTTTCTTAGCTAACTGTATTTTTGCCAT 2770       2780       2790       2800       2810       2820
GCTTATGGTCTTTTATTTTTTGTGTTCTTATAACTATTATAATGCTGTTCAGAATTCTGA 2830       2840       2850       2860       2870       2880
CATCTTTTGTATCCACTTCTTAATTTCAATGACAATAAAACATGTCAGTTGACAAAGACA 2890       2900
AAAAAAAAAAAAAAAAAAAA
```

*Fig. 13*

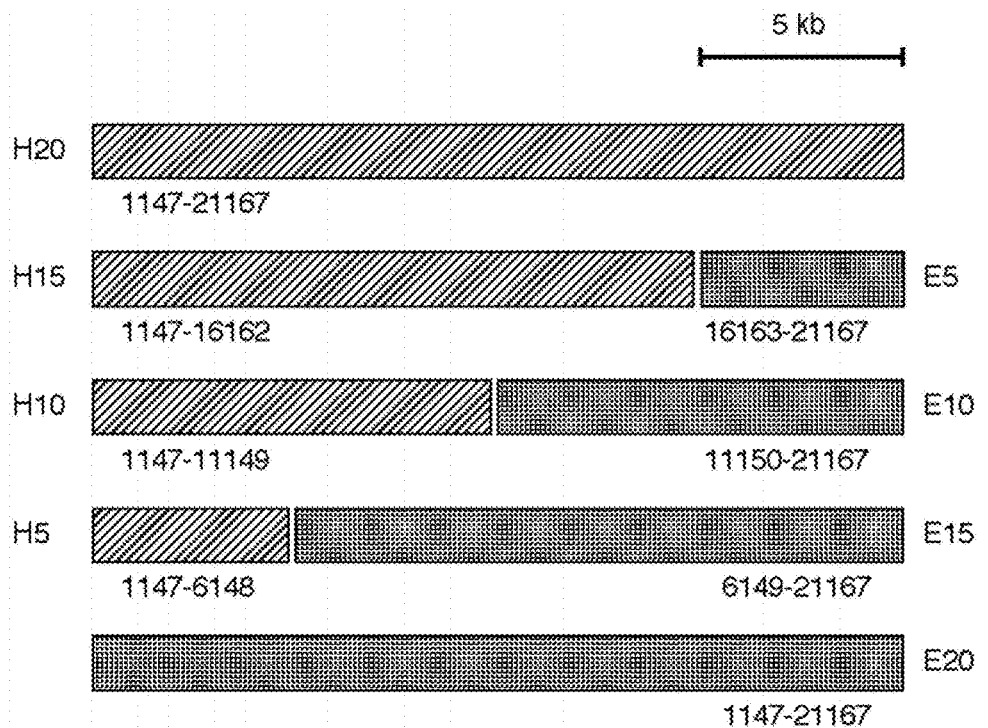
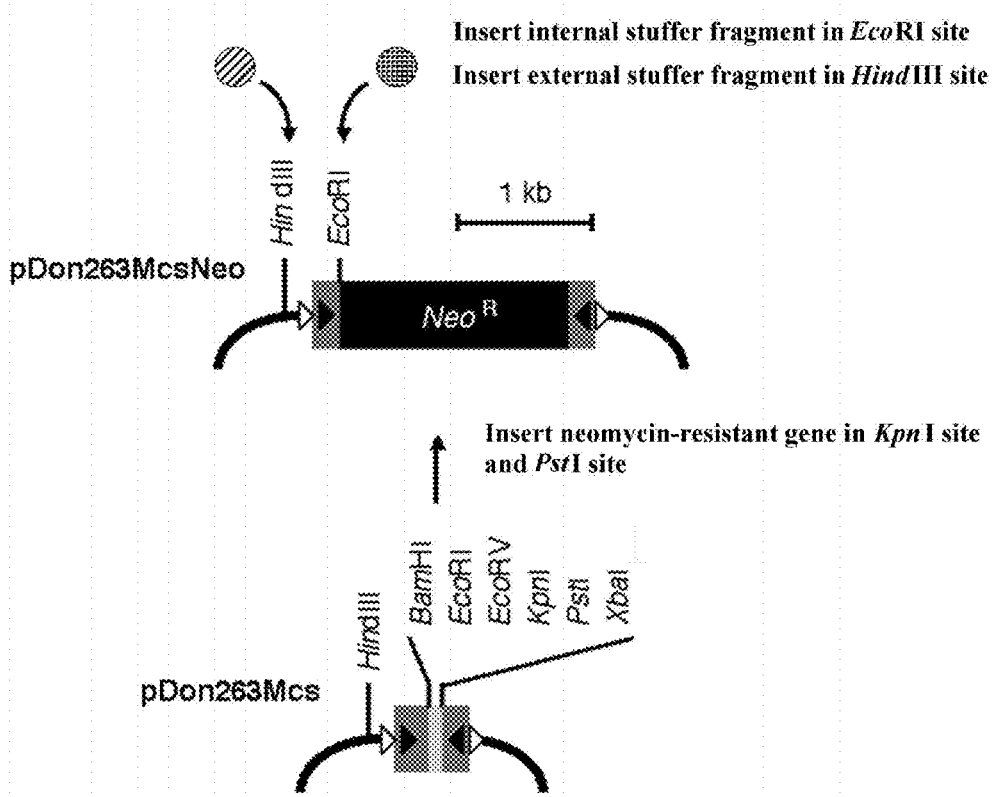
Fig. 17

NNNN  
NNNN Target site duplication  
NNNN Toll arm  
☐ Region used for PCR primer  
▶ Direction of PCR primer ] Plasmid vector (pDon)  
Chromosomes (N1, N2)

pDon TGTGAGCGGATAACAATTTCACACAGGAAACAGCTATGACCATGATTA
N1   ATCTGACTGTTTAATACACACATACCCATCCGAAGGTCCTTAGAAACC
N2   ACTATCTATGTTTAGTACTCTGCTATACATGTAAACAAACACTGTGAT

CGCCAAGCTTGCATGGTCCCTTTAGCCAGTAGCGGTTCTAGGCACGGG
AAGCAATTTAGCCTCACAGTAAGAATCAGTAGCGGTTCTAGGCACGGG
AAATGTTTATGTCATTTTTAGCACTTCAGTAGCGGTTCTAGGCACGGG

CCGTCCGGCGGTGGC..............GGGATGGTCTCGCCCGGG
CCGTCCGGCGGTGGC..............GGGATGGTCTCGCCCGGG
CCGTCCGGCGGTGGC..............GGGATGGTCTCGCCCGGG

ATTCAGGGTAGAACCGCCACTGCCTTTAGCGACATTCACTGGCCGTCG
ATTCAGGGTAGAACCGCCACTGGTAAGAATTTACAGACGGTGAAGAGT
ATTCAGGGTAGAACCGCCACTGTAGCACTTGCAGAATAGTATATAATT

TTTTACAACGTCGTGACTGGGAAAACCCTGGCGTTACCCAACTTAATC
CAGGGTTTATTTATTTACATCTAAAGTATTTTGCGTGGCACCTGCCTC
ATGCTTAAGCAATCTCTTATACTTAGGTTTTCAAATTCTCAGTGGGAA

*Fig. 19*

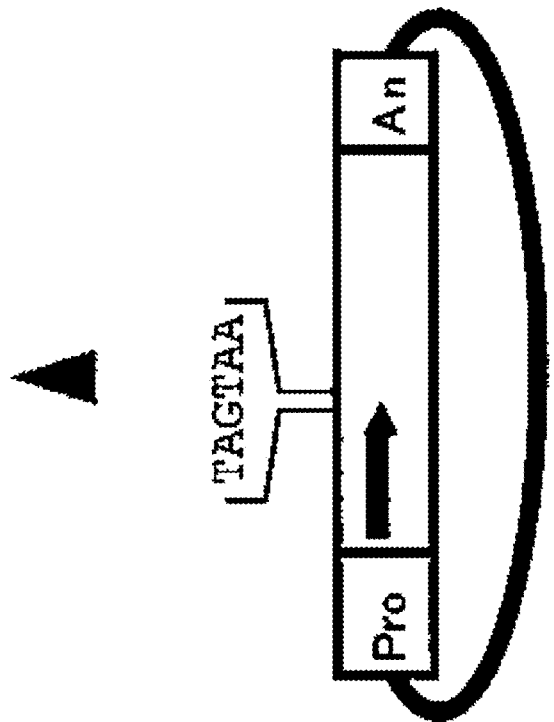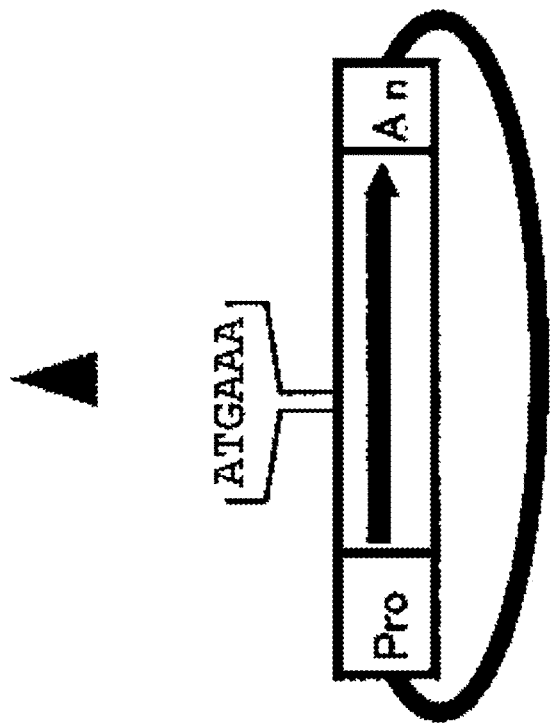
Fig. 26

| | |
|---|---|
| Donor | CTGTGGGCCCTGTCTGGTCGCGGGTTCTGTGCAGACGTCTC |
| Clone 1 | ACGCAGTGGCTCCAGGTAGTATGGAATAGAGGAATAGACTTT |
| Clone 2 | AAGTGAGCTGTATTACCGATAGTAACATGCTATGACAATGAA |

GGTTTCAGACGAGCCCAACGGGCCGCAGTACCCTCACAGCGG
CTTCACACTAGTAAAACAATGGTAGACGTGATGGAAAACAAG
TACGGGCTGACGATCTGATCAAGAGTGCGGGAAATATTGCGA

GATCGATGACAGGGAGCGCTGGCCTTTAGC`CAGTAGCGGTTC`
TGTGCTCACAACATCACACAATTAAAAATT`CAGTAGCGGTTC`
GAAGGATGCCACGCATTGGTCACTTCGAAA`CAGTAGCGGTTC`

`TAGGCACGGGCCGTCCGG------GGGGAGTAATTCAGGGTA`
`TAGGCACGGGCCGTCCGG------GGGGAGTAATTCAGGGTA`
`TAGGCACGGGCCGTCCGG------GGGGAGTAATTCAGGGTA`

`GAACCGCCACTG`CCTTTAGCTTTCTTCAACCGGACGTGTCGT
`GAACCGCCACTG`TCTGCGTATTATTAATTCTCGCTCCGGGAA
`GAACCGCCACTG`CTAAGGAGATAGAGAATAAGGGTTTTATCT

TGTGCAGGAAACTATGGAGGGTTTAACTGTGGGGAATGCAGA
CTATCCGAGAGATATTAGCAAGACAATAATACACTAAAAGTA
GAAGGGTAGGCAACGCACTGGCGTAAACGCTGGTGACCGTGG

TTCGGTTACTGGGGCTCCAACTGTGCTGAGTACAGAGAGTCA
TTTNCTACGATTCTCGCGAGACGTATGATAATATAATGGCAG
GCGGCGGTGAATCACTTACCATCAGGTGACCCGTCTTGCTCG

*Fig. 30*

TOL1 FACTOR TRANSPOSASE AND DNA INTRODUCTION SYSTEM USING THE SAME

CROSS-REFERENCE TO RELATED APPLICATIONS

This application is the U.S. national phase, pursuant to 35 U.S.C. §371, of PCT international application Ser. No. PCT/JP2007/073565, filed Dec. 6, 2007, designating the United States and published in Japanese on Jun. 19, 2008 as publication WO 2008/072540. PCT/JP2007/073565 claims priority to Japanese Patent Application Ser. No. 2007-253321, filed Sep. 28, 2007 and to Japanese Patent Application Ser. No. 2006-335786, filed Dec. 13, 2006. The entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 26, 2012, is named 84239305.txt and is 96,675 bytes in size.

TECHNICAL FIELD

The present invention relates to an enzyme for catalyzing transposition of a transposon (hereinafter referred to as a transposase) and uses thereof. Specifically, the present invention relates to a transposase of Tol1 element (Transposable element of Oryzias latipes, no. 1) which is a transposon derived from medaka fish. The invention also relates to a polynucleotide encoding the transposase, a DNA introduction system and a DNA introduction method using the transposase, and a DNA introducing kit using the system.

BACKGROUND ART

A DNA transposable element is one kind of DNA repeat sequence, and are common in vertebrate genomes. However, most vertebrate transposable elements have lost their transposition activities. Among vertebrate DNA transposable elements, transposition activities have only been directly demonstrated in the zebrafish Tzf element (Lam W L, Lee T S, Gilbert W. (1996) Proc Natl Acad Sci USA 93: 10870-10875) and in the medaka fish (*Oryzias latipes*) Tol2 element (Transposable element of *Oryzias latipes*, no. 2) (Koga A., Suzuki M., Inagaki H., Bessho Y. and Hori H. (1996) Transposable element in fish. Nature 383: 30).

The Tol1 element is a DNA transposable element present in medaka fish and at 100 to 200 copies per genome (Koga A., Sakaizumi M., Hori H. (2002) Zoolog Sci 19: 1 to 6 (Non-patent Document 1)). This element was discovered as an insert into a mutant tyrosinase gene. The mutant tyrosinge gene has a phenotype of a complete albino body color (Koga A., Inagaki H., Bessho Y., and Hori H. (1995) Mol Gen Genet 249: 400-405. (Non-patent Document 2)). Tyrosinase is an enzyme essential in the biosynthesis of melanin. Tol2's transposition activity was demonstrated in Tol2 thereafter. Unlike Tol2, since excision and insertion was not directly detected in the Tol1 element, it was originally believed that the Tol1 element had already lost its transposition activity. In addition to the copy first discovered in a tyrosinase gene, other copies were also isolated and examined; however, none had the structure of a gene (Koga A., Inagaki H., Bessho Y., and Hori H. (1995) Mol Gen Genet 249: 400-405. (Non-patent Document 2)). This further contributed to the belief that Tol1 had lost its transposition activity.

In 2001, a fish from an albino subline was found to have partial pigmentation, i.e., a mosaic pigmentation. Analysis of this fish, demonstrated that the Tol1 element had been excised from its insertion site (Tsutsumi M., Imai S., Kyono-Hamaguchi Y., Hamaguchi S., Koga A. and Hori H. (2006) Pigment Cell Res 19: 243-247. (Non-patent Document 3)). Since Tol1 had been excised, it is a DNA transposable element and that had not lost its transposition activity. However, its de novo insertion in a chromosome had not been observed. Furthermore, no transfer enzyme (transposase) has been found.

Transposable elements are used in genetic engineering and in molecular biology applications. For example, transposable elements are used to mutagenize genes, promoters, enhancers, etc., and are expected to be useful in gene therapies, and the like. The Tol2 element, which was discovered in medaka fish genomes, has already been used in such applications (Koga A., Hori H., and Sakaizumi M. (2002) Mar Biotechnol 4: 6-11. (Non-patent Document 4), Johnson Hamlet M. R., Yergeau D. A., Kuliyev E., Takeda M., Taira M., kawakami K., Mead P. E. (2006) *Genesis* 44: 438-445. (Non-patent Document 5), Choo B. G., Kondrichin I., Parinov S., Emelyanov A., Go W., Toh W. C. and Korzh V. (2006) BMC Dev Biol 6: 5. (Non-patent Document 6), Japanese Patent Application Laid-Open (JP-A) No. 2001-218588 (Patent Document 1)). In addition to the Tol2 element, the Sleeping Beauty element was artificially constructed from debris present in salmon genomes (Lvics Z., Hackett P. B., Plasterk R. H., Izsvak Z. (1997) Cell 91: 501-510. (Non-patent Document 7), National Publication of International Patent Application No. 2001-523450 (Patent Document 2)); the Frog Prince element was similarly constructed from a frog genome (Miskey C., Izsvak Z., Plasterk R. H., Ivics Z. (2003) Nucleic Acids res 31: 6873-6881. (Non-patent Document 8), National Publication of International Patent Application No. 2005-527216 (Patent Document 3)); and the piggyBac element was isolated from an insect genome (Wu S. C., Meir Y. J., Coates C. J., Handler A. M., Pelczar P., Moisyadi S. and Kaminski J. M. (2006) Proc Natl Acad Sci USA 103: 15008-15013. (Non-patent Document 9)); each of these elements has been used in gene introduction, etc. These elements are characterized by high transposition frequency. This characteristic is important when they are to be used in genetic engineering or molecular biology applications. Tol1 is estimated to have a high transposition ability given the large number of pigmented cells in mosaically-pigmented medaka fish.

Patent Document 1: JP-A No. 2001-218588
Patent Document 2: National Publication of International Patent Application No. 2001-523450
Patent Document 3: National Publication of International Patent Application No. 2005-527216 [Non-patent Document 1] Koga A., Sakaizumi M., Hori H. (2002) Zoolog Sci 19: 1-6.
[Non-patent Document 2] Koga A., Inagaki H., Bessho Y., Hori H. (1995) Mol Gen Genet 249: 400-405.
[Non-patent Document 3] Tsutsumi M., Imai S., Kyono-Hamaguchi Y., Hamaguchi S., Koga A., Hori H. (2006) Pigment Cell Res Res 19: 243-247.
[Non-patent Document 4] Koga A., Hori H., Sakaizumi M. (2002) Mar Biotechnol 4: 6-11.
[Non-patent Document 5] Johnson Hamlet M. R., Yergeau D. A., Kuliyev E., Takeda M., Taira M., Kawakami K., Mead P. E. (2006) Genesis 44: 438-445.

[Non-patent Document 6] Choo B. G., Kondrichin I., Parinov S., Emelyanov A., Go W., Toh W. C., Korzh V. (2006) BMC Dev Biol 6: 5.

[Non-patent Document 7] Ivics Z., Hackett P. B., Plasterk R. H., Izsvak Z. (1997) Cell 91: 501-510.

[Non-patent Document 8] Miskey C., Izsvak Z., Plasterk R. H., Ivics Z. (2003) Nucleic Acids Res 31: 6873-6881.

[Non-patent Document 9] Wu S. C., Meir Y. J., Coates C. J., Handler A. M., Pelczar P., Moisyadi S., Kaminski J. M. (2006) Proc Natl Acad Sci USA 103: 15008-15013.

DISCLOSURE OF THE INVENTION

Problems to be Solved by the Invention

The Tol1 element is expected to be a novel transposase element. However, no full-length copy of the Tol1 element has yet been identified.

To use a DNA transposable element in genetic engineering or molecular biologic applications, a transposase, which transfers the transposable element, is required together with the element in a vector.

An object of the present invention is thus to provide a Tol1 element transposase to use Tol1 element in genetic engineering, etc. Another object of the present invention is uses for the Tol1 element (such as in a DNA introduction system or method).

Means for Solving the Problems

The present inventors tried to identify a transposase gene of Tol1 element using the above-described mosaically-pigmented fish (medaka fish). Database searches were repeatedly performed; from which a sequence was constructed which was estimated to be a nucleotide sequence of a transposase gene. Subsequently, the inventors identified a 2.9 kb cDNA, obtained from mRNA of the mosaically-pigmented fish. This cDNA included the coding sequence for a 851 amino acid peptide. The peptide encoded by this cDNA was found to cause transposition of Tol1 element in both human and mouse cells. Further, the peptide possessed a high transposition frequency which was comparable to that of Tol2. Thus, as a transposon, Tol1 element may have the same use and value, as a transposon, as the Tol2 element. The Tol1 element may also serve as an alternative to the Tol2 element. That is, the Tol1 element may effectively act on cell lines and organisms in which insufficient transposition frequencies is provided by the Tol2 element.

Further studies revealed that Tol1 and Tol2 do not induce mutual transposition (that is, a Tol1 element transposase does not induce transposition of Tol2, and vice versa). Thus, it would be possible to successively introduce two different DNAs to a target cell and by using both the Tol1 element and the Tol2 element. Further, after introducing the two different DNAs, providing a transposase corresponding to one of the elements will allow only one of the DNAs to be specifically transferred. Accordingly, the fact that Tol1 element and Tol2 element do not induce mutual transposition enhances usefulness of Tol1 element.

Further studies revealed the existence of Tol1 elements 18 kb and 20 kb in length. Thus, the Tol1 element may be useful for introducing (transposing) a large-sized DNA fragment. Two kinds of experiments were performed focusing on this point. First, an internal region, that is apparently unnecessary for transposition, was removed from the Tol1 element (Tol1-tyr, 1855 base pairs, SEQ ID NO: 10), which had been discovered as a fragment inserted in a tyrosinase gene. Thus, it was revealed that Tol1 element was efficiently transposed when at least 157 bp of the left end (5' end region) and 106 bp of the right end (3' end region) are present. Second, as described above, transposition efficiencies were measured for inserted DNA fragments of various sizes using the Tol1 element with a deleted internal region. It was found that the larger the DNA fragment to be inserted (i.e. as the distance increased between the left end and the right end of Tol1 element), the lower transposition frequency. However, even when the distance between the left end and the right end of Tol1 element was 22.1 kb, i.e., the largest-sized DNA fragment successfully tested, the transposition frequency was still significantly higher than a frequency of random incorporation into chromosomes when not employing transposition. Indeed, 22.1 kb is the longest DNA transposable element so far reported. The above studies, which were conducted by the present inventors, demonstrated that Tol1 1 element has excellent loading ability and is exceptionally useful for introducing (transposing) large DNA fragments.

Further studies revealed that excision of Tol1 element occurred also in *Xenopus laevis*—an important model organism of genetics and vertebrate development. The further studies suggested that Tol1 element functioned as a transposable element also in cells of *Xenopus laevis*. Thus, the Tol1 element may be highly versatile.

It was also confirmed that Tol1 element functioned in insects. First, a donor plasmid containing a nonautonomous copy of Tol1 element was injected into a fertilized silkworm egg together with RNA encoding a transfer enzyme of Tol1 element. The fertilized egg was kept warm to promote development, and plasmid DNA was then recovered from the embryo. Subsequently, the plasmid was analyzed by PCR. It was found that there were individual plasmids in which portions of Tol1 element had been excised. Further, genomic DNA from the embryo was analyzed by inverse PCR, which revealed that Tol1 element had been incorporated into chromosomes. As described above, both excision and insertion are two stages of a transfer reaction; both had occurred in the silkworm. This result has the following three meanings: (1) a transfer reaction of Tol1 element does not require an element from a host organism, or if the element is required, it is present in both protostomes (e.g., frogs and fish) and deuterostomes (e.g., insects); (2) systems of gene introduction, gene trapping, mutagenesis, and the like, can be performed in silkworms using Tol1 element; and (3) similar transposition systems can be constructed and used in wide varieties of animals.

As described above, a Tol1 element transposase was successfully identified and Tol1 element had preferable properties as a transposable element for use in genetic engineering. The present invention is based on such achievements and provides the following transposase, DNA introduction system, and the like.

[1] A Tol1 element transposase containing any of proteins selected from the group consisting of the following (a) to (c):
(a) a protein having an amino acid sequence encoded by the nucleotide sequence of SEQ ID NO: 1;
(b) a protein having the amino acid sequence of SEQ ID NO: 2; and
(c) a protein having an amino acid sequence homologous to the amino acid sequence of SEQ ID NO: 2, and having an enzymatic activity for transferring Tol1 element.

[2] A polynucleotide encoding a Tol1 element transposase containing any of nucleotide sequences selected from the group consisting of the following (a) to (c):

(a) a nucleotide sequence encoding the amino acid sequence of SEQ ID NO: 2;

(b) the nucleotide sequence of SEQ ID NO: 1, SEQ ID NO: 3, or SEQ ID NO: 4; and (c) a nucleotide sequence homologous to the nucleotide sequence (b) and encoding a protein having an enzymatic activity for transferring Tol1 element.

[3] An expression construct containing the polynucleotide according to [2].

[4] The expression construct according to [3], further containing a promoter operably linked to the polynucleotide.

[5] The expression construct according to [3] or [4], further containing a poly-A additional signal sequence or a poly-A sequence connected to the polynucleotide at its downstream side.

[6] A DNA introduction system including:

(a) a donor plasmid having such a structure that a desired DNA is inserted in a transposase gene-defective Tol1 element; and (b) a helper plasmid containing the transposase according to [1] or the polynucleotide according to [2].

[7] The DNA introduction system according to [6], wherein the Tol1 element has the inverted repeat sequence of SEQ ID NO: 5 in its 5' end region and the inverted repeat sequence of SEQ ID NO: 6 in its 3' end region.

[8] The DNA introduction system according to [6], wherein the Tol1 element contains DNA of the following (a) or (b):

(a) DNA having the nucleotide sequence of any of SEQ ID NOs: 10 to 12; or (b) DNA having a nucleotide sequence homologous to the nucleotide sequence of any of SEQ ID NOs: 10 to 12, wherein a transposase having the amino acid sequence of SEQ ID NO: 1 binds to its end.

[9] The DNA introduction system according to [6], wherein the Tol1 element contains 5' end side DNA and 3' end side DNA obtained by deleting at least from the 158th base to the 1749th base counting from the 5' end of the nucleotide sequence of SEQ ID NO: 10.

[10] The DNA introduction system according to [6], wherein the Tol1 element contains DNA having the nucleotide sequence of SEQ ID NO: 21 and DNA having the nucleotide sequence of SEQ ID NO: 22.

[11] The DNA introduction system according to any of [8] to [10], wherein a target site duplicated sequence is connected to the 5' end and the 3' end of the Tol1 element.

[12] The DNA introduction system according to [11], wherein the target site duplicated sequence contains the sequence of any of SEQ ID NOs: 13 to 15.

[13] The DNA introduction system according to any of [6] to [12], wherein the desired DNA is a gene.

[14] The DNA introduction system according to any of [6] to [13], wherein the donor plasmid is a vector obtained by inserting a desired DNA in a transposase gene-defective Tol1 element, and the helper plasmid is a vector containing the polynucleotide according to [2].

[15] The DNA introduction system according to [14], wherein the vector is a helper plasmid which contains a promoter operably linked to the polynucleotide.

[16] The DNA introduction system according to [14] or [15], wherein the vector is the helper plasmid which contains a poly-A additional signal sequence or a poly-A sequence connected to the polynucleotide at its downstream side.

[17] A DNA introduction method including a step of introducing the DNA introduction system according to any of [6] to [16] to a target cell which is a vertebrate cell.

[18] The DNA introduction method according to [17], wherein the target cell is a non-human vertebrate cell.

[19] The DNA introduction method according to [17] or [18], which includes a first step of introducing a first desired DNA to a target cell and further including a second step of introducing a second desired DNA to the target cell, with the second step using Tol2 element.

[20] A method of transferring a specific DNA into a genome, including a step of supplying a transposase corresponding to Tol1 element or Tol2 element to a cell obtained according to the method of [19].

[21] A method of transferring a specific DNA into a genome, including a step of introducing the transposase according to [1] or the polynucleotide according to [2] into a cell having a transposase gene-defective Tol1 element.

[22] The method according to [21], wherein another polynucleotide sequence is inserted in the Tol1 element.

[23] A cell obtained by the system according to any of [6] to [16], the method according to any of [17] to [19], or the method according to any of [20] to [22].

[24] A DNA introducing kit, including a donor plasmid made of an expression construct containing a transposase gene-defective Tol1 element and an insertion site and a helper plasmid including an expression construct containing the transposase according to [1] or the polynucleotide according to [2].

[25] The DNA introducing kit according to [24], wherein the Tol1 element has an insertion site between its 5' end region DNA and its 3' end region DNA, which element is obtained by deleting DNA from at least the 158th base to the 1749th base counting from the 5' end in the nucleotide sequence of SEQ ID NO: 10.

[26] The DNA introducing kit according to [24], wherein the Tol1 element has an insertion site between DNA having the nucleotide sequence of SEQ ID NO: 21 and DNA having the nucleotide sequence of SEQ ID NO: 22.

[27] The DNA introducing kit according to any of [24] to [26], wherein the insertion site includes a plurality of different kinds of restriction enzyme recognition sites.

[28] The DNA introducing kit according to any of [24] to [27], wherein the donor plasmid is a vector containing a transposase gene-defective Tol1 element and an insertion site, and the helper plasmid is a vector containing the polynucleotide according to [2].

[29] The DNA introducing kit according to [28], wherein the vector is the helper plasmid which contains a promoter operably linked to the polynucleotide.

[30] The DNA introducing kit according to [28] or [29], wherein the vector being the helper plasmid further contains a poly-A additional signal sequence or a poly-A sequence connected to the polynucleotide at its downstream side.

[31] A reconstructed transposon having a structure inserted with the polynucleotide according to [2] in a transposase gene-defective Tol1 element.

[32] The transposon according to [31], containing a promoter operably linked to the polynucleotide.

[33] The transposon according to [31] or [32], containing a poly-A additional signal sequence or a poly-A sequence connected to the polynucleotide at its downstream side.

[34] A DNA introduction system, containing the transposon according to any of [31] to [33].

BRIEF DESCRIPTION OF THE DRAWINGS

FIG. 4 shows alignment using the Clustal-X program of a Tol1 element transposase and parts of other transposases of the hAT family (SEQ ID NOS 23-53, respectively, in order of appearance). It is known that an element of the hAT family has some regions where amino acid sequences are preserved. The regions are expressed by A to F (Cited document 27). D and F out of A to F are located in a comparatively short region and are likely associated with dimerization of a protein. Elements having high homology to Tol1 were selected from the elements in the hAT family (Gen Bank Accession No. PF05699, at the World Wide Web (www) ncbi.nlm.nih.gov/Genbank/index.html). Results are shown in FIG. 4. Names encoded in UniProtKB were used as names of respective elements. Five letters indicating source species are added to the names. Positions of amino acids are indicated. A Clustal-X default method was used to color the amino acids.

FIG. 8 shows nucleotide sequences of insertion points of inserted Tol1 copies (SEQ ID NOS 54-71, respectively, in order of appearance). Genomic DNA was extracted from G418-resistant cells obtained by transfecting a donor plasmid and a helper plasmid and cut with EcoRI or PstI. The two restriction enzymes did not cut the donor plasmid. After genomic DNA was electrophoresed in a 1.0% agarose gel, DNA fragments with sizes from 3.7 to 9.0 kb were recovered from the gel, and ends thereof were ligated using T4 DNA ligase under a low DNA concentration (500 ng/2.0 ml) conditions. Inverse PCR was performed on the ligated DNA. The primer used recognized an end region of Tol1-tyr (the bases 162 to 133 (SEQ ID NO: 20) of the nucleotide sequence (SEQ ID NO: 10) of GenBank Accession No. D42062). When PCR products were electrophoresed, 10 or more bands were generated per reaction. The PCR product was inserted into a plasmid to form a clone and a nucleotide sequence thereof was examined using the same primer as used in the inverse PCR. nucleotide sequences around insertion points of these genomic DNA clones are shown. For reference, a sequence of a region corresponding to the donor plasmid is shown. 8 bp of TSD was observed in all insertion points.

FIG. 11 shows the nucleotide sequence (DDBJ/EMBL/GenBank Accession No. AB264112, SEQ ID NO: 3) of cDNA (whole length 2,900 bp) of a Tol1 transposase and its deduced amino acid sequence (whole length 851 aa, SEQ ID NO: 2).

FIG. 12 shows a continuation of FIG. 11.

FIG. 13 shows a continuation of FIG. 12.

FIG. 15a shows a procedure for producing a short donor plasmid. pDon1855 is a plasmid containing the whole Tol1-tyr element and 8 bp of target site duplication (nucleotide sequence is CCTTTAGC (SEQ ID NO: 13)), using pUC19 as a vector. PCR was performed using pDon1855 as a template to produce a short donor fragment. Outwardly-orientated primers were designed that recognized each Tol1 end region, the primers comprising a SalI recognition site in their 5' ends. A PCR product was cut with SalI, and the both ends were ligated with the T4 DNA ligase into a circularized plasmid. A neomycin-resistant gene was inserted into a SalI site of the circularized plasmid. The neomycin-resistant gene was amplified from the pCMV-Tag1 plasmid (1675 to 3474 bases of DDBJ/EMBL/GenBank Accession No. AF025668) with a primer including a SalI recognition site. Black triangles shown in the drawing indicate end inverted repeat sequences, white triangles indicate target site duplications, and gray triangles indicate PCR primers. FIG. 15b shows helper plasmids. pHel1851aa was a complete helper plasmid. pHel1851aa was produced by inserting the sequence encoding a Tol1 transfer enzyme (851 amino acids (SEQ ID NO: 2), 31 to 2817 bases of DDBJ/EMBL/GenBank Accession No. AB264112) between the CMV promoter of the pCI plasmid (Promega Corp., Madison, Wis., USA) and a poly-A additional signal. pHel316aa is a defective helper plasmid. pHel316aa was prepared by introducing a mutation into pHel851aa by PCR. Bases 996 to 1001 of AB264112 is ATGAAA, which corresponds to amino acids, methionine and lysine, in a transfer enzyme. Using PCR, ATGAAA was mutated to TAGTAA. This mutation generated two termination codons near the middle of the ORF of the transfer enzyme.

FIG. 17 shows donor plasmids having Tol1 elements of various lengths. pDon263Mcs (bottom panel) is an empty plasmid having a multicloning site. pDon263Mcs was prepared by removing each restriction enzyme recognition site present in pUC19, other than its HindIII recognition site. Six restriction enzyme recognition sites were then provided in a bonding portion of the Tol1 left and right arms, as shown in the drawing. The above-described modifications were made by PCR using a 5'-end modified primer. pDon263McsNeo (middle panel) was obtained by inserting a neomycin-resistant gene into a KpnI site and a PstI site of pDon263Mcs. Rectangles (upper panel) indicate DNA fragments ligated to form long Tol1 elements. These DNA fragments were produced by PCR amplification of various parts of bacteriophage λ (DDBJ/EMBL/GenBank Accession No. J02459). Numbers below the rectangles represent nucleotide positions of the amplified fragments. A PCR primer used for amplification included an EcoRI or HindIII recognition site in its 5'-end. The PCR product was cut with EcoRI or HindIII and then inserted into a respective site of pDon263McsNeo.

FIG. 19 shows nucleotide sequences around insertion points (SEQ ID NOS 72-77, respectively, in order of appearance). Genomic DNA was extracted from a line derived from two colonies (N1 and N2) that had become neomycin-resistant and could be digested with HindIII. Since Tol1 element of a donor plasmid does not contain a HindIII recognition site, the Tol1 element itself should not be digested. The digested DNA was electrophoresed in a 0.8% agarose gel, and DNA fragments corresponding to 10 to 30 kb were recovered and ends were then ligated with T4 DNA ligase in a low concentration state (100 ng/500 □l). Inverse PCR was performed using the ligated DNA as template. The primers corresponded to the arms of Tol1 (130 to 101st bases and 1758 to 1787th bases of D42062). PCR conditions were as follows: [94° C., 2 minutes], 36×[94° C., 20 seconds; 64° C., 20 seconds; 72° C., 5 minutes], and [72° C., 5 minutes]. The PCR products were ligated into a plasmid, and the nucleotide sequence was amplified using the same primers as used in the inverse PCR. Nucleotide sequences near insertion points are shown. Nucleotide sequences of corresponding portions of the donor plasmid are aligned. An 8 bp target site duplication was formed in an insertion point of a host. The boxed portions correspond to PCR primer recognition sites used in later analyses of Tol1 elements (detail of which are described below in FIG. 20).

FIG. 20a shows amplification of Tol1 element. DNAs used as templates for PCR are pDon263McsNeoE20 (pDon) and two transformant lines (N1 or N2). The boxed portions in FIG. 19 correspond to PCR primer recognition sites used in these analyses. (P0 represents a sequence corresponding to plasmid pDon, P1 represents a sequence corresponding to cell line N1, and P2 represents a sequence corresponding to cell line N2). PCR was performed with the combination described above each electrophoresis lane. PCR conditions were as follows: [94° C., 2 minutes], 30×[98° C., 10 seconds; 68° C., 20 seconds], and [68° C., 10 minutes]. PCR products were electrophoresed in a 0.8% agarose gel with 2 μl of each 20 μl PCR product loaded per lane. A PCR product was generated only for a correct combination of a template and a primer. FIG. 20b shows comparison of restriction enzyme digestion patterns. After ethanol precipitating the PCR products, precipitated PCR products were solubilized in sufficient distilled water to provide approximately the same final DNA concentration for each PCR product. The solubilized PCR products were cut with BamHI and KpnI, and electrophoresed in a 1.0% agarose gel. The whole region of the nucleotide sequence of pDon263McsNeoE20 is known. When pDon263McsNeoE20 is digested with BamHI and KpnI, five fragments from 1.5 kb to 11.7 kb are generated. A PCR product based on DNA from a transformant cell line had the same digestion pattern as the donor plasmid.

FIG. 26 illustrates plasmids used as templates for RNA synthesis. The pTem851aa plasmid was prepared by inserting a sequence encoding a Tol1 transfer enzyme (nt 31 to 2817 of DDBJ/EMBL/GenBank Accession No. AB031079) into the pSP64 Poly (A) Vector (Promega corp.). "Pro" indicates a SP6 promoter and "An" indicates a poly (A) sequence. When RNA is synthesized using pTem851aa as a template, RNA (mRNA851aa) of about 2,900 nucleotides is transcribed. This RNA encodes a full-length transfer enzyme. The six bases (ATGAAA) encodes amino acids methionine and lysine. The pTem316aa plasmid was prepared by introducing a mutation, by PCR, which replaced the ATGAAA with two termination codons (TAGTAA). RNA (mRNA316aa) of about 2,900 nucleotides is formed; however the translated peptide ends at the two termination codons.

The upper image shows PCR products which confirm that the donor plasmid was recovered. PCR conditions were as follows: [94° C. for 120 seconds], 25×[94° C. for 20 seconds; 64° C. for 20 seconds; 72° C. for 150 seconds], and [72° C. for 150 seconds]. The lower image shows PCR products for detecting excision. PCR conditions were as follows: [94° C. for 120 seconds], 40×[94° C. for 20 seconds; 64° C. for 20 seconds; 72° C. for 20 seconds], and [72° C. for 20 seconds].

Figure 29:
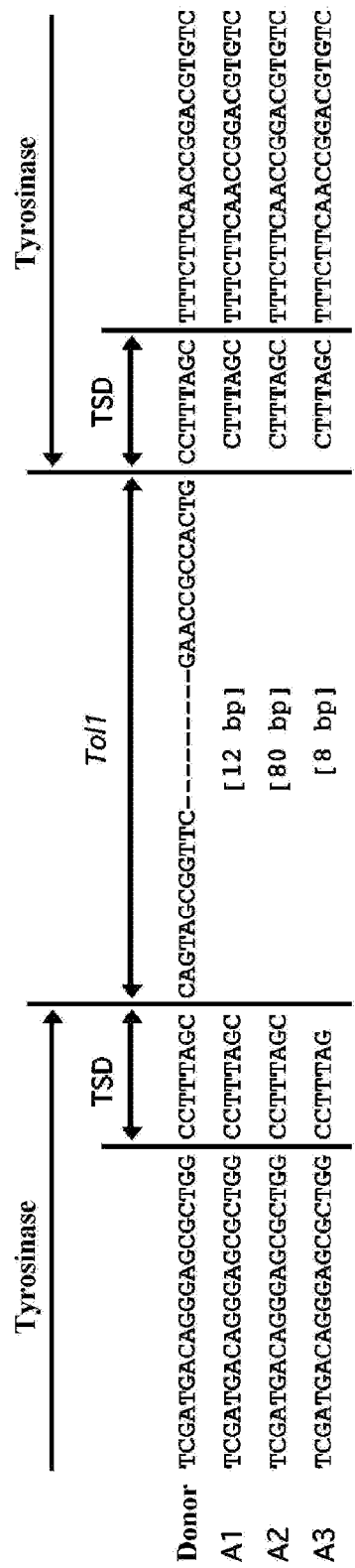

FIG. 29 shows nucleotide sequences of PCR products in excision detection (SEQ ID NOS 91, 101 and 92-94, respectively, in order of appearance). The "Donor" indicates a nucleotide sequence of both ends and portions subsequent thereto of Tol1 element on the donor plasmid. "Tol1" indicates Tol1 element, "Tyrosinase" indicates a portion derived from a tyrosinase gene of medaka fish, and "TSD" indicates target site duplication. "A1," "A2," and "A3" indicate PCR products for each of the three samples. Tol1 element regions were deleted in all three samples, and other sequences were contained in the regions. Lengths thereof are shown in the drawing and respective nucleotide sequences are shown in the bottom.

FIG. 30 shows nucleotide sequences of clones detected as having insertions (SEQ ID NOS 95-100, respectively, in order of appearance). The "donor" indicates a nucleotide sequence of both ends and portions subsequent thereto of Tol1 element of the donor plasmid. "Clone 1" and "clone 2" indicate nucleotide sequences of corresponding portions of two clones obtained by an inverse PCR. A part of Tol1 element is expressed by outline characters on a black background.

FIG. 30 shows nucleotide sequences of clones detected as having insertions. The "donor" indicates a nucleotide sequence of both ends and portions subsequent thereto of Tol1 element of the donor plasmid. "Clone 1" and "clone 2" indicate nucleotide sequences of corresponding portions of two clones obtained by an inverse PCR. A part of Tol1 element is expressed by outline characters on a black background.

BEST MODE FOR CARRYING OUT THE INVENTION

For the sake of simplicity, definitions and meanings of some terms used in the present specification are described below.

Inclusive expressions such as terms "contain" or "comprise" are used as expressions also including meanings such as "consist" or "is/are."

A "nucleotide sequence encoding an amino acid sequence" in the present invention refers to a polynucleotide capable of encoding a protein. Therefore, a nucleotide sequence can have a coding region that corresponds to an amino acid sequence and also a sequence portion that does not correspond to the amino acid sequence. Further, degeneracy of a codon is also considered. Thus, in an "amino acid sequence encoded by a nucleotide sequence," degeneracy of a codon is also considered.

The term "polynucleotide" refers to a polynucleotide in any form such as DNA and PNA (peptide nucleic acid), and RNA. The polynucleotide in the present invention is preferably DNA or mRNA.

The term "isolated" in the present invention is used interchangeably with "purified." An "Isolated" transposase, which is derived from natural materials, will be substantially free of the natural materials other than the transposase. Such an isolated transposase is substantially free of impurities (i.e., natural materials other than the tranposase). For example, for a transposase isolated from natural materials, the content of impurities is less than about 20% by weight, preferably less than about 10%, more preferably less than about 5%, and further more preferably less than about 1%. An "isolated" transposase, which is prepared by genetic engineering, will be substantially free of other components derived from a host cell, culture medium, and the like. For example, for an isolated transposase prepared by genetic engineering, the content of impurities will be less than about 20% by weight, preferably less than about 10%, more preferably less than about 5%, and further more preferably less than about 1%. A "transposase" in the present specification can simply mean a "transposase in an isolated state" unless the context indicates that a different meaning is intended. The term "enzyme" can be used in place of the term "transposase".

An "Isolated" polynucleotide, which is derived from natural materials, is separated from other nucleic acids coexisting in the natural materials. However, other nucleic acid components such as a flanking sequence in a natural state (for example, a sequence of a promoter region, and a terminator sequence) may be present. For example, "isolated" genomic DNA, substantially lacks other DNA components naturally coexisting with the genomic DNA. An "isolated" DNA prepared by genetic engineering (such as cDNA), will be substantially free of cell components, culture solutions, and the like. An "isolated" DNA, which is prepared by chemical synthesis, will be substantially free of precursors (i.e., raw materials) such as dNTP, chemical substances used in a synthesis process, and the like. A "polynucleotide" in the present specification can simply mean a polynucleotide in an isolated state unless the context indicates that a different meaning is intended.

The term "DNA introduction" in the present specification means to introduce DNA into a target cell. Accordingly, genetic modifications (such as mutagenesis and gene targeting) are also included in the concept of DNA introduction.

(Tol1 Element Transposase)

A first aspect of the present invention provides a Tol1 element transposase, which is based on Applicants' discovery of a Tol1 element transposase. A "Tol1 element transposase" refers to an enzyme capable of transferring Tol1 element, a transposon as found in medaka fish. Hereinafter, the term "transposase", unless otherwise specified, refers to the "Tol1 element transposase".

In one embodiment, the transposase of the present invention has an amino acid sequence encoded by the nucleotide sequence of SEQ ID NO: 1. As shown in examples described later, the nucleotide sequence (including a termination codon) is an ORF (open reading frame) encoding a Tol1 element transposase. SEQ ID NO: 2 (851 amino acids) is a deduced amino acid sequence encoded by the ORF. Another embodiment of the present invention is a protein having the amino acid sequence of SEQ ID NO: 2 (FIGS. 11 to 13). Note that a cDNA corresponding to the amino acid sequence (including poly-A, FIGS. 11 to 13, SEQ ID NO: 3) is registered in DDBJ/EMBL/GenBank as Accession No. AB264112 (not published as of Dec. 13, 2006).

A transposase of the present invention has high specificity to a nucleotide sequence of substrate DNA. It does not have substantial enzymatic activity for transferring Tol2 element, which is a transposon also found in medaka fish.

In general, when a part of an amino acid sequence of a protein is modified, the resulting protein may have equivalent activity as an unmodified protein. That is, modification of an amino acid sequence may not have a substantial effect on a protein's activity; the protein's activity may remain after modification. Thus, another aspect of the present invention provides a protein having an amino acid sequence homologous to the amino acid sequence of SEQ ID NO: 2 and having an enzymatic activity for transferring Tol1 element (hereinafter referred to as a "homologous protein"). The "homologous amino acid sequence" herein refers to an amino acid sequence different from of SEQ ID NO: 2, however, the "homologous protein" substantially retains the enzymatic activity for transferring Tol1 element as the amino acid sequence of SEQ ID NO: 2.

The "partial difference of an amino acid sequence" means a change in an amino acid sequence, e.g., by deletion or substitution, of one to several amino acids in an amino acid sequence, or addition or insertion of one to several amino acids, or combinations thereof. The difference of an amino acid sequence herein is acceptable as long as enzymatic activity for transferring Tol1 element is retained (some fluctuation in activity is acceptable). As long as this requirement is met, a location at which an amino acid sequence is different is not particularly limited, and the difference may be generated in a plurality of locations. "Plurality" herein is, for example, less than about 30% of the amino acids, preferably it is less than about 20%, more preferably it is less than about 10%, further more preferably it is less than about 5%, and most preferably it is less than about 1%. That is, a homologous protein has an identity of, for example, about 70% or more, preferably about 80% or more, more preferably about 90% or more, further more preferably about 95% or more, and most preferably about 99% or more relative to the amino acid sequence of SEQ ID NO: 2.

It is preferable that a homologous protein has amino acid substitutions in an amino acid residue that is not essential to an enzymatic activity for transferring Tol1 element. A "preservative amino acid substitution" herein refers to substitution of an amino acid residue with an amino acid residue having a side chain with similar properties. Amino acid residues are classified into several families by their side chains, such as basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). Preservative amino acid substitution is preferably a substitution of amino acid residues in the same family.

A percent identity of two amino acid sequences or two nucleotide sequences (hereinafter, "two sequences") can be determined by the following procedure, for example. First, two sequences are aligned so that they can be optimally compared (for example, a gap may be introduced in a first sequence to optimize alignment with a second sequence). When a molecule (amino acid residue or nucleotide) at a specific position in the first sequence is the same as a molecule at a corresponding position thereto in the second sequence, the molecules are considered identical. A percent identity of two sequences is a function of the number of identical positions between the two sequences (i.e., percent identity=number of identical positions/total number of positions×100). The number and sizes of gaps required for alignment are also taken into consideration.

Mathematical algorithms can be used to compare two sequences and determine their percent identity. Specific examples of the mathematical algorithm applicable to comparison of sequences include an algorithm described in Karlin and Altschul (1990) *Proc. Natl. Acad. Sci. USA* 87: 2264-68 and modified in Karlin and Altschul (1993) Proc. Natl. Acad. Sci. USA 90: 5873-77, but are not limited thereto. Such an algorithm is incorporated into the NBLAST program and XBLAST program (version 2.0) described in Altschul et al. (1990) *J. Mol. Biol.* 215:403-10. To obtain an amino acid sequence homologous to a specific amino acid sequence, for example, a BLAST polypeptide search may be carried out by the XBLAST program at a score of 50 and a wordlength of 3. To obtain a nucleotide sequence homologous to a specific nucleotide sequence, for example, BLAST nucleotide search may be carried out by the NBLAST program at a score of 100 and a wordlength of 12. To obtain a gap alignment for comparison, Gapped BLAST described in Altschul et al. (1997) *Amino Acids Research* 25(17): 3389-3402 is used. When BLAST and Gapped BLAST are employed, a default parameter of a corresponding program (such as XBLAST and NBLAST) can be used. See the World Wide Web (www) ncbi.nlm.nih.gov for details. Examples of another mathematical algorithm applicable to comparison of sequences include the algorithm described in Myers and Miller (1988) Comput Appl Biosci. 4:11-17. Such an algorithm is incorporated in the ALIGN program available from, for example, the GENESTREAM network server (IGH Montpellier, France) or the ISREC server. When the ALIGN program is used for comparison of amino acid sequences, for example, the PAM120 residue mass table is used, a gap length penalty can be set to 12 and a gap penalty can be set to 4.

An identity of two amino acid sequences can be determined with the GAP program of the GCG software package using Blossom 62 matrix or PAM250 matrix, and by setting a gap load to 12, 10, 8, 6, or 4 and a gap length load to 2, 3, or 4. Further, a homology of two nucleic acid sequences can be determined with the GAP program of the GCG software package (available from the World Wide Web (www) gcg.com) by setting a gap load to 50 and a gap length load to 3.

The transposase of the present invention can be prepared by genetic engineering. For example, a suitable host cell (such as *Bacillus* coli) is transformed with a polynucleotide encoding the transposase of the present invention thereby creating a transformant. A protein expressed in the transformant which synthesizes the transposase is recovered. The recovered protein is purified in a manner depending on its further applications. Various modifications of a recombinant transposase are possible. For example, DNA encoding the transposase and another suitable DNA can be inserted into the same vector. Thereby, a recombinant protein is produced from the vector, which comprises the transposase connected to any peptide or protein encoded by the other suitable DNA. Further, the transposase can be modified by addition of a sugar chain and/or lipid, or modified to generate processing of N ends or C ends. Due to the above-described modifications, extraction of a recombinant protein, simplification of purification, addition of biological functions, and the like are possible.

The methods for preparing the transposase of the present invention is not limited to genetic engineering. For example, if natural materials exist, the transposase can also be prepared from the natural materials by a standard techniques (e.g., fractionation, extraction, purification, etc.). The transposase of the present invention is generally prepared in an isolated state.

(Polynucleotide Encoding Tol1 Element Transposase)

A second aspect of the present invention provides a polynucleotide encoding the transposase. In one embodiment, the polynucleotide is made of a nucleotide sequence encoding the amino acid sequence of SEQ ID NO: 2. Specific examples of the nucleotide sequences are shown in SEQ ID NO: 1, SEQ ID NO: 3, and SEQ ID NO: 4. The nucleotide sequence of SEQ ID NO: 1 is an ORF encoding a Tol1 element transposase. Further, the nucleotide sequence of SEQ ID NO: 3 corresponds to a full-length cDNA encoding a Tol1 element transposase. The nucleotide sequence of SEQ ID NO: 4 corresponds to a genomic DNA sequence (4355 base pairs, absent a target site duplicated sequence (TSD)) which encodes the mRNA corresponding to the full-length cDNA.

If part of a polynucleotide encoding a protein is modified, the resulting protein may have equivalent enzymatic activity as the protein encoded by an unmodified polynucleotide. That is, modification of a nucleotide sequence may not have a substantial effect on the encoded modified protein's enzymatic activity, and the unmodified protein's activity may be retained in the modified protein. Thus, another embodiment of the present invention provides a polynucleotide made of a nucleotide sequence homologous to the nucleotide sequence of any of SEQ ID NO: 1, SEQ ID NO: 3, or SEQ ID NO: 4, and encoding a protein having an enzymatic activity for transferring Tol1 element (hereinafter a "homologous polynucleotide"). The "homologous nucleotide sequence" herein refers to a nucleotide sequence different from the nucleotide sequence of any of SEQ ID NO: 1, SEQ ID NO: 3, and SEQ ID NO: 4, in which the difference, however gives no substantial effect on a function of the protein encoded by the homologous nucleotide sequence (function meaning enzymatic activity for transferring Tol1 element).

Specific examples of a homologous polynucleotide include a polynucleotide that hybridizes (under stringent conditions) to a polynucleotide made of a nucleotide sequence complementary to the nucleotide sequences of any of SEQ ID NO: 1, SEQ ID NO: 3, and SEQ ID NO: 4 when under stringent conditions. The "stringent conditions" herein refers to conditions where a so-called specific hybrid is formed, but a nonspecific hybrid is not formed. Such stringent conditions are known to a skilled person, and are described elsewhere, for example, Molecular Cloning (Third Edition, Cold Spring Harbor Laboratory Press, New York) and Current protocols in molecular biology (edited by Frederick M. Ausubel et al., 1987). The stringent conditions include, for example, such conditions that incubation is carried out at about 42° C. to about 50° C. using a hybridization solution (50% formamide, 10×SSC (0.15 M NaCl, 15 mM sodium citrate, pH 7.0), 5×Denhardt solution, 1% SDS, 10% dextran sulfate, 10 µg/ml of modified salmon sperm DNA, 50 mM phosphate buffer (pH 7.5)), and then washing is carried out at about 65° C. to about 70° C. with 0.1×SSC and 0.1% SDS. Preferable stringent conditions include, for example, such conditions that 50% formamide, 5×SSC (0.15 M NaCl, 15 mM sodium citrate, pH 7.0), 1×Denhardt solution, 1% SDS, 10% dextran sulfate, 10 µg/ml of modified salmon sperm DNA, 50 mM phosphate buffer (pH 7.5) is used as a hybridization solution.

Other specific examples of a homologous polynucleotide include a polynucleotide made of a nucleotide sequence containing a substitution, deletion, insertion, addition, or inversion at one or a plurality of positions when compared to the nucleotide sequence of any of SEQ ID NO: 1, SEQ ID NO: 3, and SEQ ID NO: 4, and encoding a protein having an enzymatic activity for transferring Tol1 element. Substitution and deletion of bases may occur in a plurality of positions. "Plurality" herein indicates, for example, 2 to 40 bases, preferably 2 to 20 bases, and more preferably 2 to 10 bases. The number of bases capable of being changed depends the specific positions of the bases and the type of amino acid encoded by the polynucleotide. Such a homologous polynucleotide as described above can be obtained by modifying a polynucleotide having the nucleotide sequence of any of SEQ ID NO: 1, SEQ ID NO: 3, and SEQ ID NO: 4 by substitution, deletion, insertion, addition and/or inversion; such modifications can be via a restriction enzyme digestion, digestion with exonuclease, treatment with DNA ligase, or the like; via a site-specific mutagenesis (Molecular Cloning, Third Edition, Chapter 13, Cold Spring Harbor Laboratory Press, New York); and random mutagenesis (Molecular Cloning, Third Edition, Chapter 13, Cold Spring Harbor Laboratory Press, New York) A homologous polynucleotide can also be obtained by other methods such as exposure to ultraviolet radiation.

Other examples of a homologous polynucleotide include a polynucleotide in which such difference in bases, as described above, are recognized due to a polymorphism typified by SNP (monobasic polymorphism).

An isolated polynucleotide of the present invention can be prepared using a standard genetic engineering technique, molecular biology technique, biochemical technique, or the like, thereby preparing a sequence as disclosed in the present specification or attached sequence listings. Specifically, the polynucleotide of the present invention can be isolated from a medaka fish (*Oryzias laptipes*) genomic DNA library or cDNA library or a cell extract of medaka fish. In each, isolation can be performed using an oligo-nucleotide probe/primer capable of specifically hybridizing to the polynucleotide of the present invention. The oligo-nucleotide probe/primer can be synthesized using a commercially-available automated DNA synthesizer. Preparation of such libraries are taught in Molecular Cloning, (Third edition, Cold Spring Harbor Laboratory Press, New York).

For example, a polynucleotide having the nucleotide sequence of SEQ ID NO: 3 can be isolated from a medaka fish cDNA library using a probe, which hybridizes to the whole or a part of the nucleotide sequence or a sequence complementary thereto. Also, the polynucleotide can be amplified and isolated using a nucleic acid amplification reaction (for example, PCR) using a synthesized oligo-nucleotide primer designed to specifically hybridize to a part of the nucleotide sequence.

(Expression Construct Containing Tol1 Element Transposase)

A further aspect of the present invention relates to an expression construct containing the polynucleotide of the present invention. A promoter is preferably incorporated in the expression construct of the present invention. However, when a polynucleotide contained in the expression construct already has a promoter region, a second promoter can be omitted.

The promoter is operably linked to the polynucleotide of the present invention. In an expression construct comprising a polynucleotide that is operably-linked to a promoter, the promoter enables expression of the polynucleotide in a target cell. Herein, "a promoter that is operably linked to a specific polynucleotide sequence" has the same meaning as "a specific polynucleotide sequence under control of a promoter," and generally, a specific polynucleotide sequence is linked to the 3'-end side of the promoter directly or via another sequence.

CMV-IE (cytomegalovirus initial gene-derived promoter), SV40ori, retrovirus LTP, SRα, EF1α, β-actin, and like promoters can be used. Mammal-tissue-specific promoters such as an acetylcholine receptor promoter, an enolase promoter, an L7 promoter, a nestin promoter, an albumin promoter, an alpha-fetoprotein promoter, a keratin promoter, and an insulin promoter may be used.

In the expression construct of the present invention, a poly-A additional signal sequence, a poly-A sequence, an enhancer sequence, a selective marker sequence, and the like can also be included. Stability of mRNA generated from the expression construct is improved by use of a poly-A additional signal sequence or a poly-A sequence. The poly-A additional signal sequence or the poly-A sequence is connected downstream to the polynucleotide. Improvement of expression efficiency occurs with use of an enhancer sequence. Further, when an expression construct containing a selective marker sequence is used, presence or absence (and a degree thereof) of the expression construct can be confirmed using the selective marker.

Preparing an expression construct by including a promoter, the polynucleotide sequence of the present invention, an enhancer sequence (if necessary), and a selective marker sequence (if necessary) can be performed by standard recombinant DNA techniques, e.g., using a restriction enzyme and a DNA ligase (See, e.g., Molecular Cloning, Third Edition, 1.84, Cold Spring Harbor Laboratory Press, New York can be referred to).

The expression construct of the present invention can introduce the polynucleotide sequence of the present invention into a target cell. Although the type of expression construct used is not particularly limited, the expression construct preferably is an expression vector. The "expression vector" herein refers to a nucleic acid molecule capable of introducing a contained polynucleotide into a desired cell (target cell) and of expressing the polynucleotide in the cell. Examples of such include a viral vector and a non-viral vector. A gene introduction method using a viral vector occurs via infection of a cell with a virus, and a high gene introduction efficiency can be obtained. An adenovirus vector, an adeno-associated virus vector, a retrovirus vector, a lentivirus vector, a herpesvirus vector, a Sendai virus vector, and the like, have been developed for use in the present invention. For an adeno-associated virus vector, a retrovirus vector, and a lentivirus vector, foreign genes included into a vector are incorporated into a host chromosome, and stable, long-term expression can be expected. Since retrovirus vectors require cell division for incorporation of a foreign gene into a host chromosome, a retrovirus vector is not appropriate for gene introduction into a non-dividing cell. On the other hand, lentivirus vectors and adeno-associated virus vectors cause incorporation of foreign genes into host chromosomes after infection and in non-dividing cells; therefore, these vectors are effective for expressing foreign genes stably and for a long time in non-dividing cells, such as nerve cells and liver cells.

Each viral vector can be prepared by following standard methods or using a commercially-available kit. For example, preparation of an adenovirus vector can be carried out by a COS-TPC method or a full-length DNA introduction method. The COS-TPC method produces a recombinant adenovirus by co-transfecting a recombinant cosmid containing a desired cDNA or an expression cassette and a parent virus DNA-terminal protein complex (DNA-TPC) into 293 cells; then homologous recombination in the 293 cells integrates foreign genes into the 293 cell's chromosome (Miyake, S., Makimura, M., Kanegae, Y., Harada, S., Takamori, K., Tokuda, C., and Saito, I. (1996) Proc. Natl. Acad. Sci. USA, 93, 1320.). Full-length DNA introduction method produces a single recombinant adenovirus using restriction digestion of a recombinant cosmid comprising a desired gene; thereafter transfecting the product to 293 cells (Miho Terashima, Saki Kondo, Yumi Kanegae, and Izumi Saito (2003) Experimental Medicine 21 (7) 931). The COS-TPC method can be performed with the Adenovirus Expression Vector Kit (Dual Version) (TAKARA BIO INC.) and Adenovirus genome DNA-TPC (TAKARA BIO INC.). Further, the full-length DNA introduction method can be performed with Adenovirus Expression Vector Kit (Dual Version) (TAKARA BIO INC.).

A retrovirus vector can also be prepared by the following procedure. First, viral genes (e.g., gag, pol, and env genes) other than packaging signal sequences between LTR (Long Terminal Repeat) present on the both ends of a virus genome are removed. Then a desired gene is inserted therein. The constructed viral DNA is introduced in a packaging cell constitutionally expressing gag, pol, and env genes. Here, only a vector RNA having a packaging signal sequence is incorporated in a virus particle and a retrovirus vector is produced.

As a vector obtained by application or improvement in an adeno vector, a vector in which specificity is improved by modification of a fiber protein (specific infection vector), and a gutted vector from which improvement in an expression efficiency of a desired gene can be expected (helper-dependent vector), and the like, have been developed. The expression vector of the present invention can be constructed as such a viral vector.

As a non-viral vector, a liposome, a positively charged liposome (Felgner, P. L., Gadek, T. R., Holm, M. et al., Proc. Natl. Acad. Sci., 84:7413-7417, 1987), HVJ (Hamagglutinating virus of Japan)-liposome (Dzau, V. J., Mann, M., Morishita, R. et al., Proc. Natl. Acad. Sci., 93:11421-11425, 1996, Kaneda, Y., Saeki, Y. & Morishita, R., Molecular Med. Today, 5:298-303, 1999), and the like have been developed. The expression vector of the present invention can be constructed as such a non-viral vector.

(DNA Introduction System Utilizing Tol1 Element)

Another aspect of the present invention relates to a DNA introduction system using Tol1 element. The DNA introduction system of the present invention can be used for introducing specific DNA into a target cell. In other words, specific DNA can be introduced into genomic DNA of a target cell using the DNA introduction system of the present invention. The DNA introduction system of the present invention is used for genetic manipulation, such as gene introduction and gene modification.

The DNA introduction system of the present invention includes a donor plasmid and a helper plasmid. The donor plasmid and the helper plasmid preferably exist as distinct plasmids. That is, it is preferable that the donor plasmid and the helper plasmid are physically separate.

However, the donor plasmid and the helper plasmid may coexist in a single plasmid.

The donor plasmid delivers a desired DNA to a target cell, with the desired DNA inserted in a transposase gene-defective Tol1 element.

The "target cell" means a cell to which the DNA introduction system of the present invention is applied, that is, a cell to be genetically manipulated using the DNA introduction system of the present invention. The "target cell" herein indicates a vertebrate cell, as examples cells of mammals (e.g., human, monkey, cattle, horse, rabbit, mouse, rat, guinea pig, and hamster), birds (e.g., chicken and quail), fish (e.g., medaka and zebrafish), and amphibians (e.g., frog). Examples of target cells include: a myocardial cell, a smooth muscle cell, an adipose cell, a fibrocyte, a bone cell, a chondrocyte, an osteoclast, a parenchymal cell, an epidermal keratinocyte (keratinocyte), epithelial cells (e.g., skin epidermal cell, corneal epithelial cell, conjunctival epithelial cell, oral mucosal epithelium, follicle epithelial cell, oral mucosal epithelial cell, airway mucosal epithelial cell, and intestinal mucosal epithelial cell), endothelial cells (e.g., corneal endothelial cell and vascular endothelial cell), a nerve cell, a glial cell, a splenic cell, a pancreatic β cell, a mesangium cell, a Langerhans cell, a liver cell, or precursor cells thereof, or mesenchymal stem cells (MSC), embryonic stem cells (ES cells), embryonic germ cells (EG cells), adult stem cells, fertilized eggs, and the like. Cells can have abnormalities, including cancer cells, or established cell lines such as HeLa cells, CHO cells, Vero cells, HEK293 cells, HepG2 cells, COS-7 cells, NIH3T3 cells, Sf9 cells, and the like.

The DNA introduction system of the present invention can be used on an isolated target cell or to a target cell within an organism. Therefore, the present invention can be carried out in vitro, in vivo, or ex vivo. "Isolated" used herein refers to a state of being taken out from the original environment thereof (for example, from an organism) Accordingly, an isolated target cell exists in a culturing vessel or another container, and the cell can be artificially manipulated in vitro. Specifically, a cell separated from a living body and cultured ex vivo (including an established cell line) can be an isolated target cell. As long as a target cell is "isolated" according to the above-described meaning, the target cell is an isolated cell even if within an organism.

The "isolated target cell" can be isolated from a biological organism. Isolated target cells can also be obtained from RIKEN BioResource Center (independent administrative institution), the National Institute of Technology and Evaluation Institute (independent administrative institution), ATCC (American Type Culture Collection), DSMZ (German Collection of Microorganisms and Cell Cultures), and the like.

In one embodiment of the present invention, the DNA introduction system of the invention is applied to vertebrate cells outside a human. That is, the DNA introduction system is carried out on a target cell isolated from a human or a non-human vertebrate.

Tol1 element used in the donor plasmid is a transposase gene-defective Tol1 element. "transposase gene-defective" means containing no functional transposase gene, and also includes situations when some of the transposase gene remains as long as the transposase gene cannot be expressed as a functioning enzyme; thus, it is not limited to when the transposase gene is completely deleted. In other words, a part of the transposase gene's sequence is changed such that the unchanged part of the gene has lost its activity. Such a state is included in the meaning of "transposase gene-defective."

Tol1 element is a DNA-type element existing in about 100 to 200 copies in a genome of medaka fish (Koga A., Sakaizumi M., and Hori H. (2002) Zoolog Sci 19: 1-6. (Cited document 10)). It was discovered as a fragment inserted in a tyrosinase gene (Koga A., Inagaki H., Bessho Y., and Hori H. (1995) Mol Gen Genet 249: 400-405. (Cited document 11)). The sequence (SEQ ID NO: 10) of this fragment (Tol1-tyr, 1855 base pairs, lacking a target site duplicated sequence (TSD)) is registered in GenBank as Accession No. D42062. The inverted repeat sequence, characteristic of Tol1 element, was identified from an analysis of Tol1-tyr (Koga A., Sakaizumi M., and Hori H. (2002) Zoolog Sci 19: 1-6. (Cited document 10)). A preferable embodiment of the present invention uses a Tol1 element having the inverted repeat sequence of SEQ ID NO: 5 in its 5' end region and the inverted repeat sequence of SEQ ID NO: 6 in its 3' end region. That is, in a Tol1 element in this embodiment, the sequence 5'-cagtagcggttcta-3' (SEQ ID NO: 5) is present in the 5' end region of its sense strand and the sequence 5'-tagaaccgccactg-3' (SEQ ID NO: 6) is present in the 3' end region of its sense strand. In addition, all Tol1 elements reported so far, including Tol1-tyr, have defective transposase genes, and are envisioned as being a Tol1 element in the present invention. As specific examples of Tol1 element that can be used in the present invention, nucleotide sequences thereof are shown in SEQ ID NOs: 10 to 12. Note that the nucleotide sequence of SEQ ID NO: 11 is a cloned sequence (969 base pairs) obtained by removing an internal region of 886 base pairs from Tol1-tyr; it is transposable similar to Tol1-tyr. Further, the nucleotide sequence of SEQ ID NO: 12 is a cloned sequence (297 base pairs) obtained by removing an internal region of 1576 base pairs from Tol1-tyr and adding recognition sites for six restriction enzymes. These added restriction enzyme recognition sites allow insertion of other DNA fragments; the nucleotide sequence of SEQ ID NO: 12 is transposable similar to Tol1-tyr.

A modified element of any of these examples can also be used. The "modified element" herein indicates a polynucleotide molecule made of a nucleotide sequence homologous to the nucleotide sequence of any of SEQ ID NOs: 10 to 12; it functions as a transposon similar to the unmodified polynucleotide molecule. A transposase having the amino acid sequence of SEQ ID NO: 2 can bond to an end of the modified element. The term "homologous," is defined below in the section of the "polynucleotide encoding a Tol1 element transposase".

As shown in examples described below, the present inventors found that transposition efficiency was not lost when an internal region of 1592 base pairs (from its 158th base to 1749th base counting from the 5'-end) were deleted from Tol1-tyr. Based on this finding, one embodiment of the present invention uses Tol1 element made of 5'-end region DNA and 3'-end region DNA, which is obtained by deleting at least bases from 158th base to 1749th base (1592 base pairs) counting from the 5'-end in the nucleotide sequence of Tol1-tyr (the nucleotide sequence of SEQ ID NO: 10). In other words, the embodiment uses a donor plasmid having a structure in which a desired DNA is inserted between DNA of the 5' end region of the nucleotide sequence of SEQ ID NO: 10 (157 base pairs at maximum length) and DNA of the 3' end region of the nucleotide sequence of SEQ ID NO: 10 (106 base pairs at maximum length). Maximizing the amount of a loadable foreign DNA is obtained by deleting as much as possible of the internal region that is unnecessary for transposition activity. It was suggested that, when 1592 base pairs in the internal region of Tol1-tyr is deleted, as described above, greater than 20 kb of foreign DNA can be introduced (examples of this are described below). A specific example of the 5'-end region DNA is DNA having the nucleotide sequence of SEQ ID NO: 21 (157 base pairs), and a specific example of the 3'-end region DNA is DNA having the nucleotide sequence of SEQ ID NO: 22 (106 base pairs).

Tol1 element can be easily prepared by PCR, and the like, with a Tol1 element-specific primer (see examples described below) using medaka fish genomic DNA as template. Regarding details of preparation methods, refer to examples described below, or Koga A., Sakaizumi M., and Hori H. (2002) Zoolog Sci 19: 1-6, Tsutsumi M., Imai S., Kyono-Hamaguchi Y., Hamaguchi S., Koga A., and Hori H. (2006) Pigment Cell Res 19: 243-247, and the like.

"A desired DNA" contained in a donor plasmid refers to DNA introduced into genomic DNA of a target cell by the DNA introduction system of the present invention. The DNA introduction system of the present invention can be useful for gene introduction for the purposes of functional analysis of genes, improvement and restoration (treatment) of specific functions, addition of new traits, differentiation induction, production of useful proteins (such as interferon, insulin, erythropoietin, and antibodies), formation of transgenic animals, and the like. When the DNA introduction system of the present invention is used, specific genes are the "desired DNA." Examples of the genes herein can include genetic disease-associated genes such as an adenosine deaminase (ADA) gene, a factor IX gene, a granulocyte-macrophage colony-stimulating factor (GM-CSF) gene, a p53 cancer suppressing gene, a simple herpes virus thymidine kinase (HSV-tk) gene, a vascular endothelial growth factor (VEGF) gene, and a hepatocellular growth factor (HGF), genes encoding hormones such as insulin and erythropoietin, genes encoding growth factors such as interferon, an insulin-like growth factor, an epidermal growth factor (EGF), a fibrocyte growth factor (FGF), and interleukins, genes encoding antibodies (for therapy, diagnosis, detection, etc.), marker genes such as a green fluorescent protein (GFP) gene, a β-galactosidase (lacZ) gene, a chloramphenicol-resistant (CAT) gene, and a luciferase (LUC) gene, and genes having unknown functions. In addition to genes existing in nature, genes obtained through artificial manipulation (artificial genes) can also be used. Further, genes may be normally expressed in the same cell type or in a different cell type as a target cell. Desired DNA encoding two or more genes may be introduced.

When genetic modification is intended, any DNA capable of destroying or inactivating a function in a target cell, for example, a modified gene of the target gene, is used as the "desired DNA."

An insertion position of the "desired DNA" is not particularly limited as long as the function of a transposon of Tol1 element (transposition function) remains unaffected. That is, the "desired DNA" may be inserted in a position other than in either both end that are acting sites of a transposase. For example, endogenous restriction enzyme recognition sites (e.g., SalI) existing in the region other than both ends may be used as an insertion site in Tol1 element. Alternatively, an insertion site may be artificially formed without using an endogenous restriction enzyme recognition site.

In one preferable embodiment of the present invention, a target site duplicated sequence is connected to the 5'-end and the 3'-end of Tol1 element. The "target site duplicated sequence," that is, TSD (target site duplication), indicates a tandem repeat sequence formed in transposition. When a transposon is inserted, since double stranded DNA is broken at different positions, the sequence between them is duplicated, resulting in formation of a TSD. In the case of Tol1 element, TDS with 8 bp in one side is formed. For example, a TSD having the sequence of any of SEQ ID NOs: 13 to 15 can be used in the present invention. In addition, the sequences of SEQ ID NOs: 13, 14, and 15 correspond to TSD of Tol1-tyr, TSD of Tol1-L1, and TSD of Tol1-L2, respectively.

To achieve high introduction efficiency, a vector in which desired DNA, Tol1 element, etc., is incorporated therein as an expression cassette is included in a donor plasmid. The kind of vector used is not particularly limited. Regarding kinds, production methods, and the like of the vector, the above description (section of the expression construct of the present invention) can be referred to.

The helper plasmid delivers a transposase into a target cell, and includes the transposase of the invention (i.e., Tol1 element transposase) or the polynucleotide of the invention (i.e., polynucleotide encoding the Tol1 element transposase). When the DNA introduction system of the present invention is introduced into the target cell, a transposase supplied by the helper plasmid acts on Tol1 element supplied by the donor plasmid. As a result, the desired DNA inserted in the Tol1 element is incorporated in the genomic DNA of the target cell.

To achieve a high introduction efficiency, the helper plasmid is preferably also constructed as a vector similar to the donor plasmid. That is, it is preferable to use a vector in which an expression cassette containing a polynucleotide encoding a Tol1 element transposase is incorporated in the helper plasmid.

Introduction of the donor plasmid and the helper plasmid into a target cell can be carried out by a calcium phosphate co-precipitation method, lipofection (Felgner, P. L. et al., Proc. Natl. Acad. Sci. U.S.A. 84, 7413-7417 (1984)), an HVJ liposome method, a DEAE dextran method, electroporation (Potter, H. et al., Proc. Natl. Acad. Sci. U.S.A. 81, 7161-7165 (1984)), microinjection (Graessmann, M. & Graessmann, A., Proc. Natl. Acad. Sci. U.S.A. 73, 366-370 (1976)), a gene gun method, an ultrasonic gene introduction method, etc., in consideration of kinds of the target cell, forms of the donor plasmid and the helper plasmid, and the like. When a viral vector is used as an expression construct, introduction into the target cell is performed by infection.

The donor plasmid and the helper plasmid are not necessarily introduced into a target cell simultaneously. However, it could be preferable that the both plasmids are simultaneously co-introduced into the target cell from the viewpoints of operationality and mutual actions of the both plasmids.

The present invention provides further uses of the DNA introduction system of the invention. One use is a DNA introduction method. In the DNA introduction method of the present invention, a step of introducing the DNA introduction system of the invention is carried out on a vertebrate target cell. Further, based on the finding that Tol1 element and Tol2 element do not influence each other's transposition, provided is a DNA introduction method characterized by a step of introducing a first desired DNA into a target cell using Tol1 element and including a further step of introducing a second desired DNA into the target cell using Tol2 element. A DNA introduction method using Tol2 element can be carried as described in Koga A., Hori H., and Sakaizumi M. (2002) Mar Biotechnol 4: 6-11. (Cited document 13), Johnson Hamlet M. R., Yergeau D. A., Kuliyev E., Takeda M., Taira M., Kawakami K., and Mead P. E. (2006) Genesis 44: 438-445. (Cited document 14), Choo B. G., Kondrichin I., Parinov S., Emelyanov A., Go W., Toh W. C., and Korzh V. (2006) BMC Dev Biol 6: 5 (Cited document 15), and the like. In addition, Cited document 13 reports gene introduction using Tol2 element, Cited document 14 reports mutagenesis using Tol2, and Cited document 15 reports trapping of genes and promoters or enhancers using Tol2 element.

The DNA introduction system of the present invention can be used in transgenic fish, transgenic mice, knockout mice, etc., for the purpose of producing genetically modified animals. For example, the DNA introduction system of the present invention can be introduced into a cytoplasm, a vitellus, or a nucleus of a fertilized egg of zebra fish, medaka fish, etc., by a method such as microinjection to generate transgenic fish.

By using the DNA introduction system of the present invention, a specific gene-introduced fertilized oocyte or embryonic stem cell can be produced, and a transgenic non-human mammal can be generated from such a cell. The transgenic non-human mammal can be produced by microinjection in which DNA is directly injected into a pronucleus of a fertilized egg, a method using a retrovirus vector, a method using an ES cell, or the like. A microinjection method will be described below as one example of a production method of a transgenic non-human mammal.

In microinjection, a fertilized egg is first collected from an oviduct of a female mouse whose copulation was confirmed. The fertilized egg is then cultured and the DNA introduction system of the present invention introduces a desired DNA into the pronucleus. After DNA introduction, the egg is transplanted into an oviduct of a pseudopregnant mouse; the mouse is allowed to gestate long enough to obtain a neonatal mouse (P0). To confirm that the desired DNA is correctly incorporated into chromosomes of the neonatal mouse, DNA is extracted from the tail or the like of the neonatal mouse. The extracted DNA is then subjected to PCR using a primer specific to the desired DNA, a dot hybridization method using a probe specific to the desired DNA, or the like. Although a species for "the transgenic non-human mammal" is not particularly limited, rodents such as mice and rats are preferred.
(Method of Transferring Specific DNA Site on Genomic DNA)

Another aspect of the present invention provides a method of transferring a specific DNA to a site on genomic DNA of a target cell by using the transposase of the present invention or a polynucleotide encoding the transposase. In one embodiment of this aspect, the transposase or the polynucleotide is introduced into a cell (target cell) having Tol1 element in which a polynucleotide encoding a transposase includes a deletion. The introduced transposase (or a transposase expressed from the introduced polynucleotide) acts on Tol1 element contained in the target cell to allow transposition. In addition to target cells that obtain Tol1 element artificially, a cell naturally (i.e., as an intrinsic element) having Tol1 element can be used as the "target cell" herein. That is, the method of the present invention is not limited to cells for which an exogenous Tol1 element has been introduced.

For a Tol1 element having insertion of another polynucleotide sequence, the consequences of the other polynucleotide sequence's transfer can be examined, and information about functions of the other polynucleotide sequence can be obtained. Thus, the present invention can be used for analysis of various polynucleotides' functions. For a Tol1 element lacking insertion of another polynucleotide sequence, functions of the Tol1 element itself and influences due to its insertion can be examined. Thus, the method of the present invention is also useful in studies of Tol1 element itself.

A transposase corresponding to either Tol1 element or Tol2 element enables selective transposition of a first desired DNA or a second desired DNA that are introduced into cells, with each desired DNA using one of Tol1 element or Tol2 element. That is, it is possible to control two desired DNAs independently. The present invention thus provides a method of transferring a specific DNA site on genomic DNA, which includes a step of providing a transposase corresponding to Tol1 element or Tol2 element to a target cell. The transposase may be expressed in a target cell in which polynucleotide encoding the transposase has been introduced into the target cell. Regarding introduction of a Tol2 element transposase, Koga A., Hori H., and Sakaizumi M. (2002) Mar Biotechnol 4: 6-11. (Cited document 13), Johnson Hamlet M. R., Yergeau D. A., Kuliyev E., Takeda M., Taira M., Kawakami K., and Mead P. E. (2006) Genesis 44: 438-445. (Cited document 14), Choo B. G., Kondrichin I., Parinov S., Emelyanov A., Go W., Toh W. C., and Korzh V. (2006) BMC Dev Biol 6: 5 (Cited document 15), and the like can be referred to. The amino acid sequence of the Tol2 element transposase is SEQ ID NO: 7. The cDNA sequence (which lacks a poly A) encoding the transposase and the genomic DNA sequence (which lacks a TSD) are SEQ ID NOs: 8 and 9, respectively.
(Genetically Manipulated Cells)

When the DNA introduction system or the DNA introduction method of the present invention is carried out, a genetically manipulated cell is generated. Therefore, the present invention also provides a genetically manipulated cell thus obtained. The cell of the invention can possess new characteristics and functions from the genetic manipulation. Such a cell can be used in production of specific substances, treatments of specific diseases, and the like, depending on the introduced DNA. In addition, the cell can also be used to examine the functions of the introduced DNA.
(DNA Introducing Kit)

The present invention further provides a DNA introducing kit used in the DNA introduction system and the DNA introduction method of the present invention. The DNA introducing kit has a donor plasmid as a transporter of desired DNA and a helper plasmid as a transposase source and source for essential constituent factors. Specifically, the donor plasmid includes an expression construct having a transposase gene-defective Tol1 element and having an insertion site. The helper plasmid includes an expression construct containing the transposase or a polynucleotide encoding the transposase. The "insertion site" herein means a site where a desired DNA is inserted. A restriction enzyme recognition site inherent in Tol1 element can be used as the "insertion site." For example, Tol1 element depicted in the nucleotide sequence of SEQ ID NO: 10 (Tol1-tyr, 1855 base pairs, not containing TSD) has a SalI recognition site, which can be used as an insertion site. A nucleotide sequence can be insertion into a restriction enzyme recognition site by genetic engineering. The nucleotide sequence for a recombination reaction refers to an attR sequence used in, for example, Gateway™ (Invitrogen Co., Carlsbad, Calif.) technology.

A plurality of restriction enzyme recognition sites may be used as insertion sites. A donor plasmid having a multi-cloning site (MCS) may be used. Although the restriction enzyme recognition sites included in a MCS are not particularly limited, it is preferable to include commonly-used restriction enzyme recognition sites such as HindIII, BamHI, and EcoRI. This is because a kit with high versatility is constructed including these sites. A donor plasmid (pDon253Mcs) shown in examples described below has a MCS including of BamHI, EcoRI, EcoRV, KpnI, PstI, XbaI, etc recognition sites.

As described above, transposition efficiency is not reduced when an internal region of 1592 base pairs (from its 158th base to 1749th base counting from the 5'-end) of Tol1-tyr are removed. Based on this, one embodiment of the present invention uses Tol1 element having a structure in which insertion sites are formed between the 5'-end region DNA and the 3'-end region DNA, obtained by removing at least from its 158th base to the 1749th base counting from the 5'-end in the nucleotide sequence of Tol1-tyr (nucleotide sequence of SEQ ID NO: 10). In other words, the embodiment uses a donor plasmid in which a desired DNA is inserted between DNA in the 5' end region (157 base pairs at maximum length) of the nucleotide sequence of SEQ ID NO: 10 and DNA in the 3' end region (106 base pairs at maximum length) of the nucleotide sequence of SEQ ID NO: 10. A specific example of the 5'-end region DNA is DNA having the nucleotide sequence of SEQ ID NO: 21 (157 base pairs), and a specific example of the 3'-end region DNA is DNA having the nucleotide sequence of SEQ ID NO: 22 (106 base pairs).

A preferable embodiment is a kit. The kit includes a first vector, which is used as a donor plasmid, containing Tol1 element in which a polynucleotide encoding a transposase is defective and having an insertion site. The kit also includes a second vector, which is used as a helper plasmid, containing a polynucleotide encoding a transposase. Such a kit has high convenience, and a high DNA introduction efficiency can be expected. The helper plasmid in this case further contains a promoter operably linked to a polynucleotide encoding a transposase and/or a poly-A additional signal sequence or a poly-A sequence connected to the polynucleotide in the downstream side.

(Reconstructed Transposon)

A further aspect of the present invention provides a reconstructed transposon. The reconstructed transposon of the present invention includes a polynucleotide encoding a transposase which is inserted in a transposase gene-defective Tol1 element. Preferably, a promoter operably linked to the polynucleotide encoding a transposase is also inserted in Tol1 element. When the inserted "polynucleotide encoding a transposase" contains a promoter region providing sufficient transcription activity, insertion of another promoter is unnecessary. It is preferable that a poly-A additional signal sequence or a poly-A sequence is also inserted to enhance stability of a transcription product (i.e., mRNA). In one preferable embodiment of the reconstructed transposon of the present invention, a poly-A additional signal sequence or a poly-A sequence is connected to a polynucleotide encoding a transposase in its downstream side.

Insertion of a polynucleotide encoding a transposase, and the like, may be carried out using conventional methods (see Molecular Cloning (Third Edition, Cold Spring Harbor Laboratory Press, New York), Current protocols in molecular biology (edited by Frederick M. Ausubel et al., 1987)); Molecular Cloning provides definitions for terms used herein, such as "operably linked," and "promoter,"

A specific example of a reconstructed transposon is one having a sequence in which the nucleotide sequence of SEQ ID NO: 3 or SEQ ID NO: 4 is inserted in the nucleotide sequence of any of SEQ ID NOs: 10 to 12.

The reconstructed transposon contains a transposase that can be expressed in a target cell and can function as an autonomous transposable element. Therefore, the reconstructed transposon can be used as a tool for introducing DNA independently. The present invention thus also provides a DNA introduction system using a reconstructed transposon. "Independently" means that it is unnecessary to also use a separately provided transposase; however it does not exclude use of components and elements (such as vector backbones and related reagents) as required for exerting the functions of the reconstructed transposon.

Matters not particularly mentioned in the present specification (such as conditions and operational methods) may be selected following conventional methods, and for example, as taught in Molecular Cloning (Third Edition, Cold Spring Harbor Laboratory Press, New York), Current protocols in molecular biology (edited by Frederick M. Ausubel et al., 1987).

Example 1

1. Materials and Methods
(1) Fish

Over 30 years ago, a completely albino individual medaka fish was found in a commercially bred group of fish (Cited document 27). A primary line was established from this individual, which was kept in an experimental laboratory. In this albino mutant line, 1.9 kb of Tol1 element is inserted in the first exon of a tyrosinase gene (Cited document 11). In 2001, an individual fish showing mosaic pigmentation appeared in a subline maintained at Niigata University. Pigmentation did not occur in the primary line maintained in Nagoya University. The primary line was called i¹-Tomita and the mosaically-pigmented subline was called i¹-Niigata (Cited document 12). These designations are also referred to as subline A and subline B, respectively. The sublines have not previously been bred with other lines.

(2) Database

The following public databases were used: Genomic project of medaka fish (at the World Wide Web (www) shigen.lab.nig.ac.jp/medaka/genome/): for constructing a nucleotide sequence that is likely the Tol1 element; MOTIF (at the World Wide Web (www) motif.genome.jp/): for searching a motif; Pfam (at the World Wide Web (www) sanger.ac.uk/Software/Pfam/): for collecting sequences of transfer enzymes of the hAT family; and Clustal-X (at the World Wide Web (www) bips.u-strasbg.fr/fr/Documentation/ClustalX/): for checking amino acid sequences.

(3) Reagents and Kits

The following molecular biology reagents and kits were used in accordance with manufactures' instructions: PCR enzyme ExTaq™ (Takara Bio Inc., Otsu, Japan) for PCR amplification of DNA; fosmid vector pCC1FOS™ (EPICENTRE Biotechnologies, Madison, USA) for production of genomic library; AlkPhos Direct™ Labelling and Hybridization System (GE Healthcare, Chalfont St. Giles, UK) for labeling and hybridization analysis of probes; RNeasy® kit (QIA GEN GmbH, Hilden, Germany) for RNA extraction; FirstChoice® RLM-RACE kit (Ambion, Austin, USA) for RACE analysis; PolyFect® Transfection Reagent (QIAGEN GmbH) for incorporation of DNA into cells; and G418 (Invitrogen Corp., Carlsbad, USA) for selection of G418-resistant cells. Experimental conditions are described in the experimental results and description of the drawings sections.

(4) Analysis of Transposition in Mammalian Cultured Cells

Human HeLa cells and mouse NIH/3T3 cells were used. The cells were maintained in an incubator containing 5.0% of $CO_2$ at 37° C. and were cultured in DMEM culture medium containing 10% bovine serum and an antibiotic.

$1 \times 10^5$ cells were seeded per 35 mm-dish and each culture was incubated for 24 hours. A mixture of plasmid DNAs was adjusted to 1000 ng per dish and allowed to be incorporated into the cells using a PolyFect® reagent. The culture was incubated for an additional 24 hours, the cells were then washed twice with PBS, and fresh culture medium (which lacked plasmid DNA or an incorporation reagent) was added to the culture. After 24 hours, cells were separated from the bottom of the dishes with a trypsin treatment and suspended in 2.0 ml of the culture medium. 100 µl each of the suspension was transferred to dishes of different sizes (35 mm, 60 mm, 90 mm). G418 was added to the culture medium to a final concentration of 500 µg/ml. After 12 days of G418 selection, the cells were fixed in 20% formalin and stained with Giemsa stain. A dish having approximately 100 colonies was selected and the number of colonies was counted. From that number, the colony number per $10^5$ cells initially seeded was estimated. The above-described analyses were carried out by simultaneously preparing three groups of measurement systems.

2. Experimental Results
(1) Breeding of Fish

Figure 1:
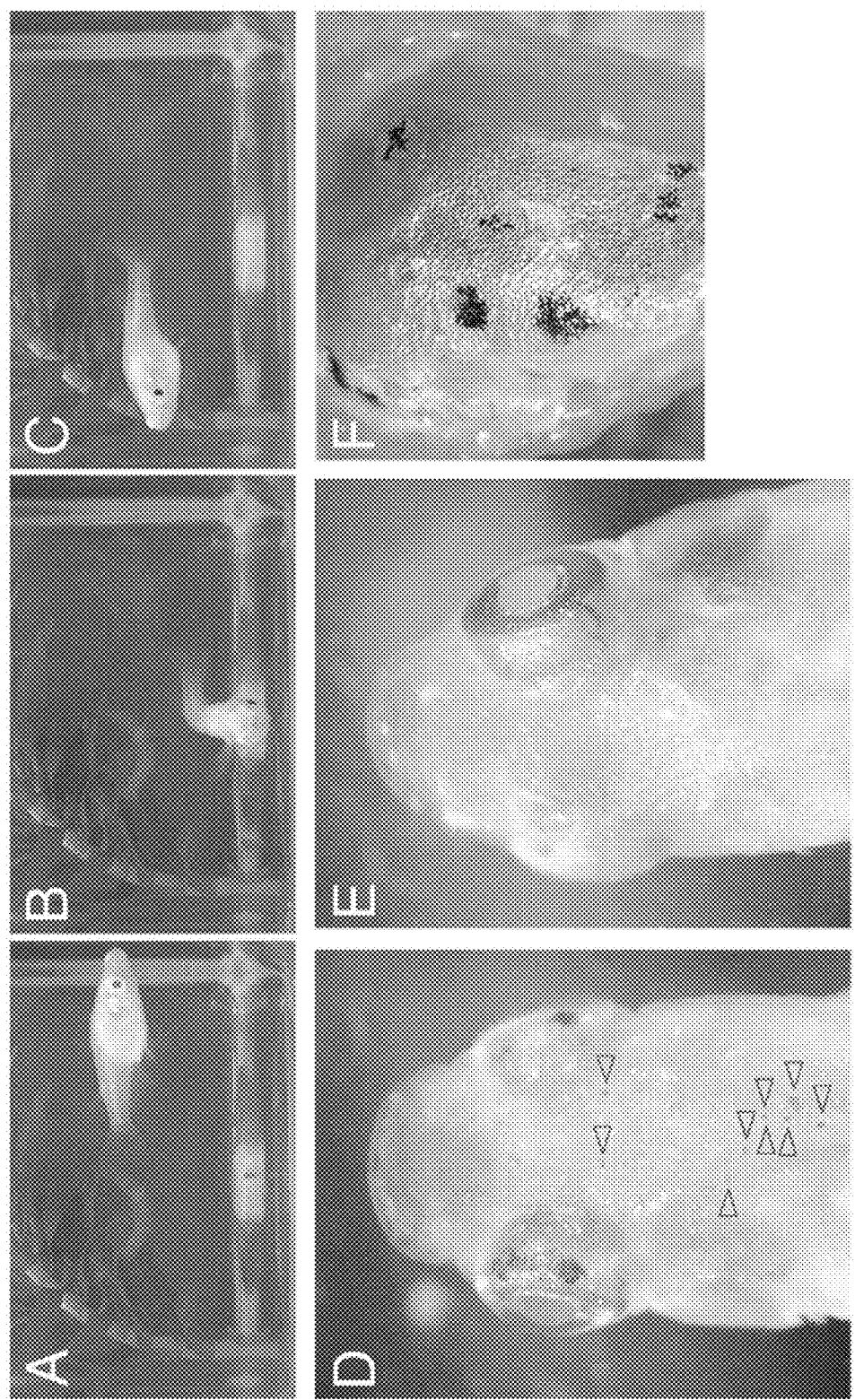
FIG. 1 shows a mosaically-pigmented fish. Panels A to C show the same fish. The fish having one black eye and one red eye was photographed from its right side (panel A), its front (panel B), and its left side (panel C). The fish in Panel D is pigmented throughout its eyes and has a large number of pigmented dots on its back skin. The dots on its back are indicated with triangles. Panel E shows a first having spoke-form pigmentation in an eye. Panel F shows a peritoneum. A peritoneum is densely pigmented in wild-type fish and pigmentation absent from albino fish.

In the moasically-pigmented subline that was discovered in 2001, the penetrance of pigmentation was 20% (i.e., the ratio of pigmented individuals among all individuals). To produce a subline having higher penetrance, a male and a female fish having strong pigmentation were bred; this was repeated for an additional four generations. As a result, the penetrance of the ultimate subline was 90% or more; in addition, pigmented spots were larger than in the original breeding pair (FIG. 1).

(2) Construction of Sequence Likely to be Full-Length Tol1 Element from Data Analysis A copy of Tol1 element (Tol1-tyr), which was isolated as an insertion into a tyrosinase gene, is 1.9 kb (SEQ ID NO: 10, containing no TSD) in length. Inverted repeat sequences are present in the 5'-end region and the 3'-end region of Tol1-tyr.

The sequence in the inverted repeat sequence in the 5' end region of a sense strand (direction from 5'-end to 3'-end) is of SEQ ID NO: 5 and the inverted repeat sequence in the 3' end region of a sense strand (direction from 5'-end to 3'-end) is of SEQ ID NO: 6. A nonautonomous copy is often formed due to deletion of the inside in a DNA type element (Cited document 19). Database searches were conducted to identify a longer copy based on Tol1-tyr. In each search, overlapping sequences were identified; these overlapping sequences, when combined, were considered part of full-length Tol1. Based on the combined overlapping sequences, further searches were performed. The further searches discovered that 4.3 kb was absent from Tol1-tyr. Then, this 4.3 kb sequence was anew checked with the database. For each base position of 4.3 kb, the nucleotide having the highest frequency was included in a consensus sequence. As a result, a 4.3 kb consensus sequence having 2.3 kb of an open reading frame (ORF) was obtained. This sequence is named as Tol1-L0.

(3) Identification of Autonomous Tol1 Element

Figure 2:
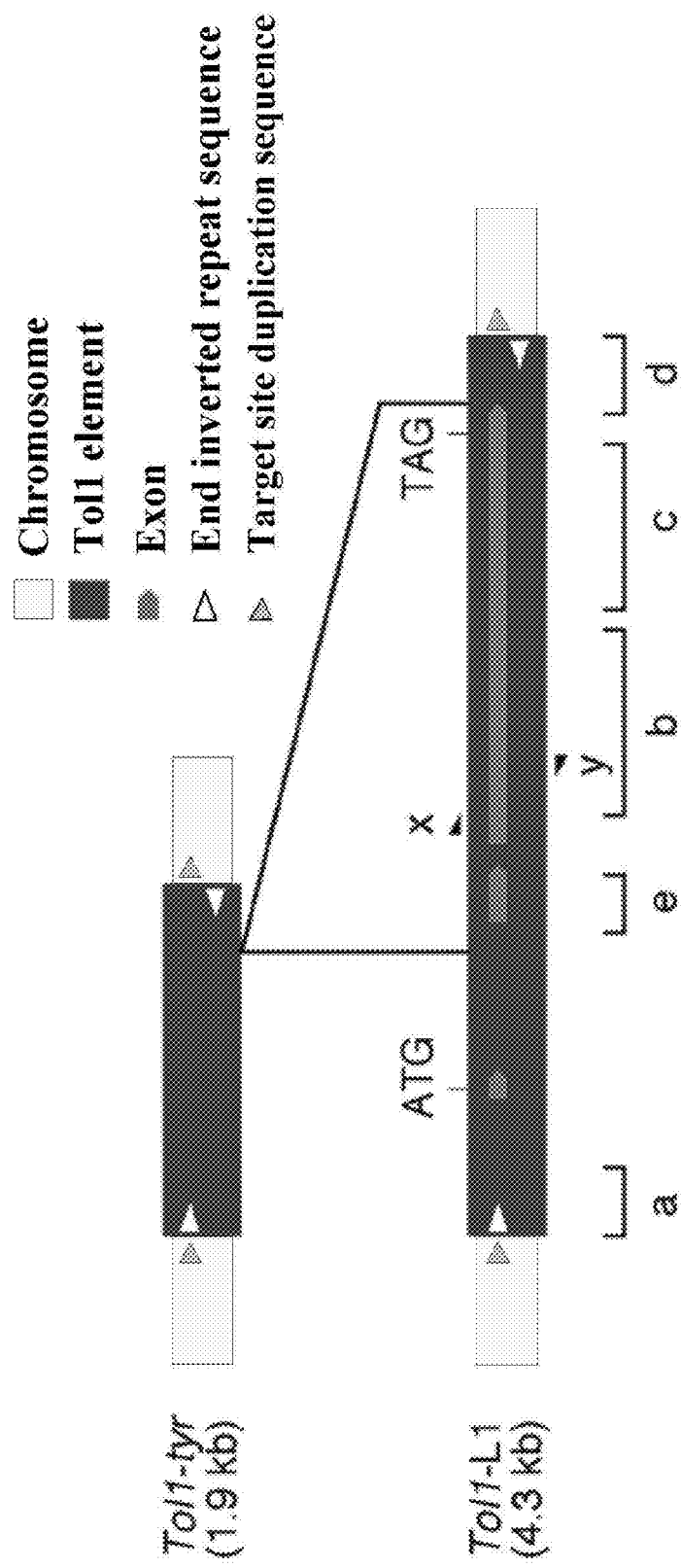
FIG. 2 shows structures of Tol1 nonautonomous and autonomous copies. Tol1-tyr is the first discovered Tol1 nonautonomous copy, and was inserted in a tyrosinase gene of fish A. Tol1-L1 is the first complete autonomous copy successfully identified, and contains a functional transposase gene. Genomic DNA of fish B was sheared, thereby producing fragments with 36 to 48 kb which were obtained and inserted into fosmid vector pCC1FOS to form a genomic library. This genomic library was screened to obtain Tol1-L1. An internal transposase gene (exon) is noted by a bar. An initiation codon (ATG) and a termination codon (TAG) of this gene are also shown. The underlined parts noted by "a" to "e" were used as targets for hybridization probes. "x" and "y" indicate positions of a 3' RACE primer and a 5' RACE primer, respectively. Sequences of these primers (primer x: SEQ ID NO: 16, primer y: SEQ ID NO: 17) correspond to positions of bases 152 to 181 and 457 to 332, respectively of the nucleotide sequence (SEQ ID NO: 3), which is registered in DDBJ/EMBL/GenBank as Accession No. AB264112.

PCR amplification of an internal 1.2 kb region of the sequence of Tol1-L0 (part of FIG. 2b) was performed on genomic DNA of a mosaically-pigmented subline (named fish B). A fragment obtained by PCR amplification was used as a probe in colony hybridization of a genomic library from subline B; the colony hybridization identified two clones. The clones were named Tol1-L1 and Tol1-L2. The two clones each included 4.3 kb of sequence and they exhibited an identical restriction enzyme map for five restriction enzymes (data not shown). Since the nucleotide sequences appeared the same, further work was performed using only Tol1-L1. As a result, the nucleotide sequence (SEQ ID NO: 4) and structure of Tol1-L1 were determined (FIG. 2). Information from a further analysis, as described below, and comparison between structures of Tol1-L1 and Tol1-tyr are shown in FIG. 2.

(4) Identification of Full-Length cDNA Likely Encoding Tol1 Transposase

Figure 3:
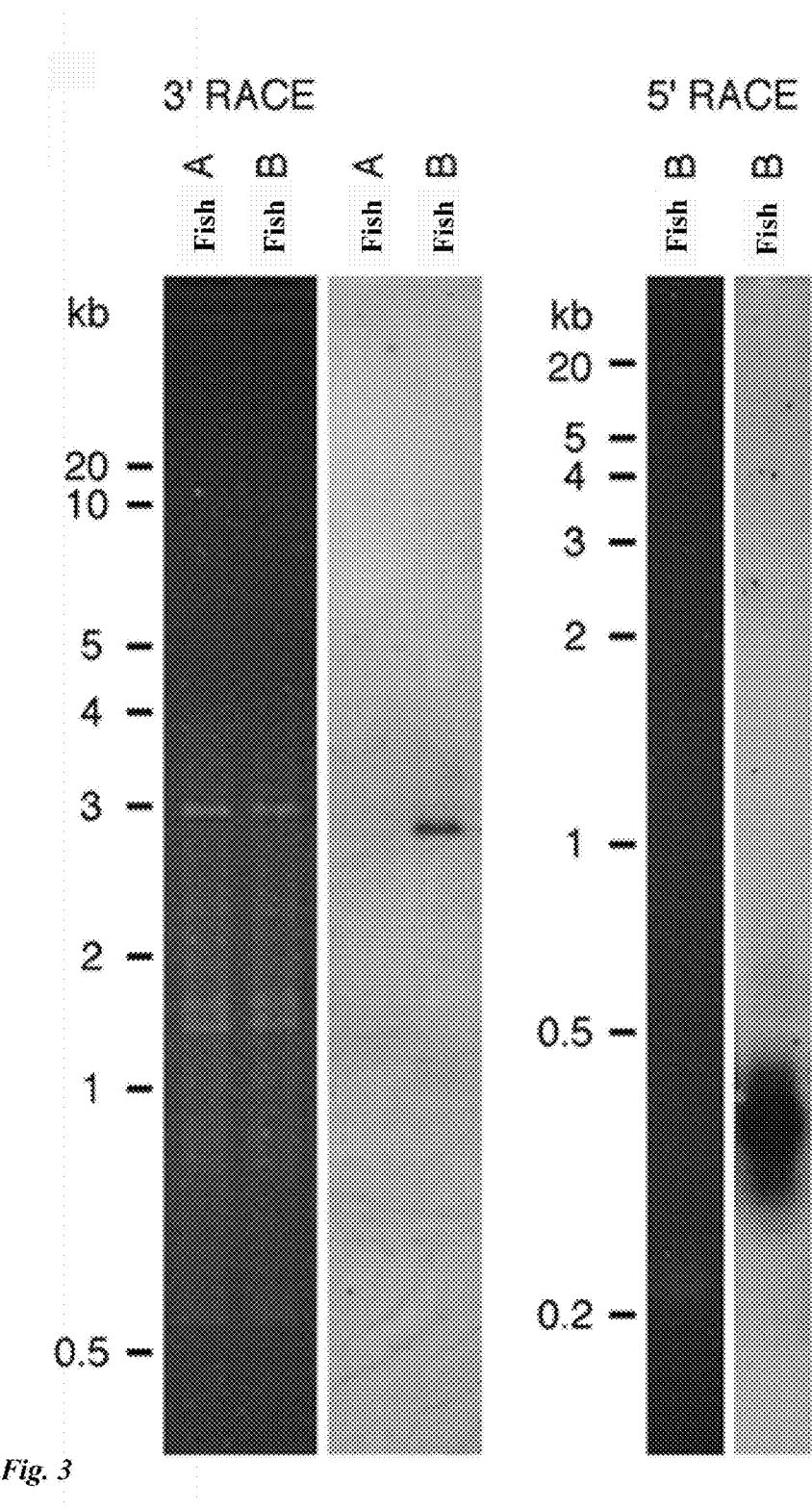
FIG. 3 shows results of RACE. RNA was extracted from embryos 7 days after fertilization by fish A or fish B and synthesis of single stranded cDNA was performed using an oligo-dT primer. Then, 3' RACE of this cDNA single strand was performed using primer "x" and a 3' adaptor primer contained in a RACE kit. A DNA fragment was electrophoresed in a 1.0% agarose gel and transferred to a nylon membrane and then hybridized with probe "b". The left panel shows the gel immediately after the electrophoresis and the right panel shows the gel after hybridization. Only one hybridization band was observed for cDNA from fish B. Subsequently, a portion of the gel corresponding to the hybridization band was excised and the DNA fragment contained therein was recovered. The recovered DNA fragment was ligated into a plasmid vector and a clone to which the probe bound was isolated by colony hybridization. 5' RACE was performed only on RNA from fish B. Primer "y" and a 5' adaptor primer contained in the RACE kit were used. Steps following PCR were the same as described above for 3' RACE except probe "e" was used in hybridizations. One hybridization band was observed; the corresponding DNA fragment was isolated as described above.

3' RACE (rapid amplification of cDNA ends) was performed to identify a transcription product of the Tol1 transposase gene. This was done using RNA extracted from an albino line without pigmentation (subline A) and a mosaically-pigmented subline (subline B). By Southern Blot, one signal was observed in subline B and no signal was observed in subline A (FIG. 3). The result indicates that a Tol1 transcription product from an ORF is present in subline B but not in subline A; if an ORF is present in subline A, the amount thereof must be very small. Then, 5' RACE of subline B was performed and one signal appeared (FIG. 3). Clones of the RACE products were obtained and their nucleotide sequences were examined; from this the cDNA sequence (SEQ ID NO: 3), with a 2.9 kb ORF (SEQ ID NO: 1), was obtained (FIGS. 11 to 13). This sequence was registered in DDBJ/EMBL/GenBank as Accession No. is AB264112. By comparing the sequence of full-length cDNA and the Tol1-L1 sequence (SEQ ID NO: 4), it was revealed that a Tol1 transposase gene is composed of three exons (FIG. 2).

Figure 4:
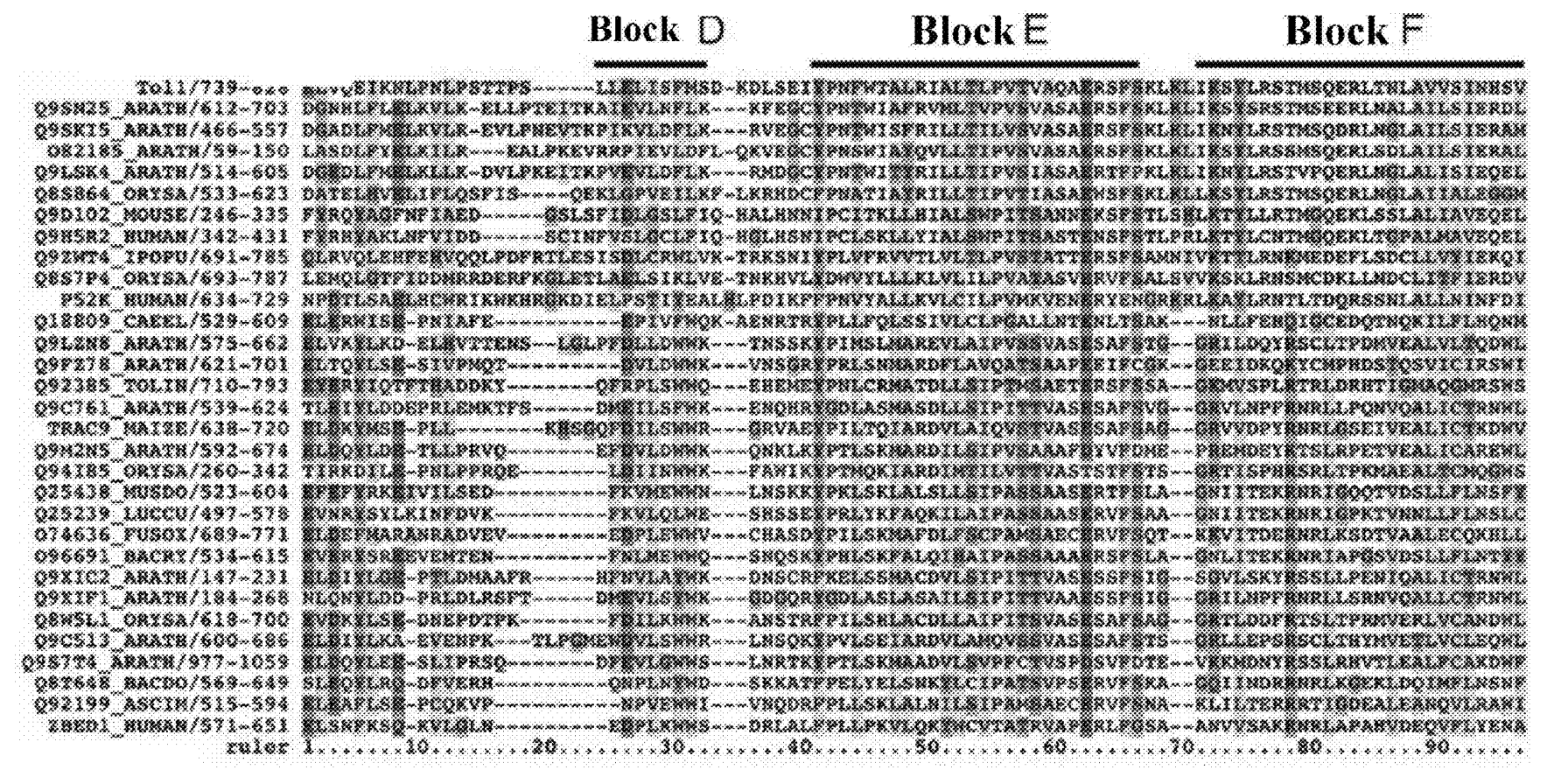

A BLAST search, using the amino acid sequence deduced from Tol1 ORF (SEQ ID NO: 2, FIGS. 11 to 13), revealed a list mainly composed of transposable elements in the hAT family. hAT family elements from rice or *Arabidopsis* had the highest similarity amongst sequences in the database (data not shown). Further, when the amino acid sequence was reviewed for the presence of common motifs, a dimerization domain (PF05699) of the hAT family was found in the Pfam database. Further, the Tol1 ORF was found to have those amino acids commonly present in Tol1 and hAT elements of other species (FIG. 4). Similarity of the amino acid sequence to Tol2 was lower than similarity to elements included in FIG. 4 (data not shown).

(5) Structure of Medaka Fish Genomic Tol1

Figure 5:
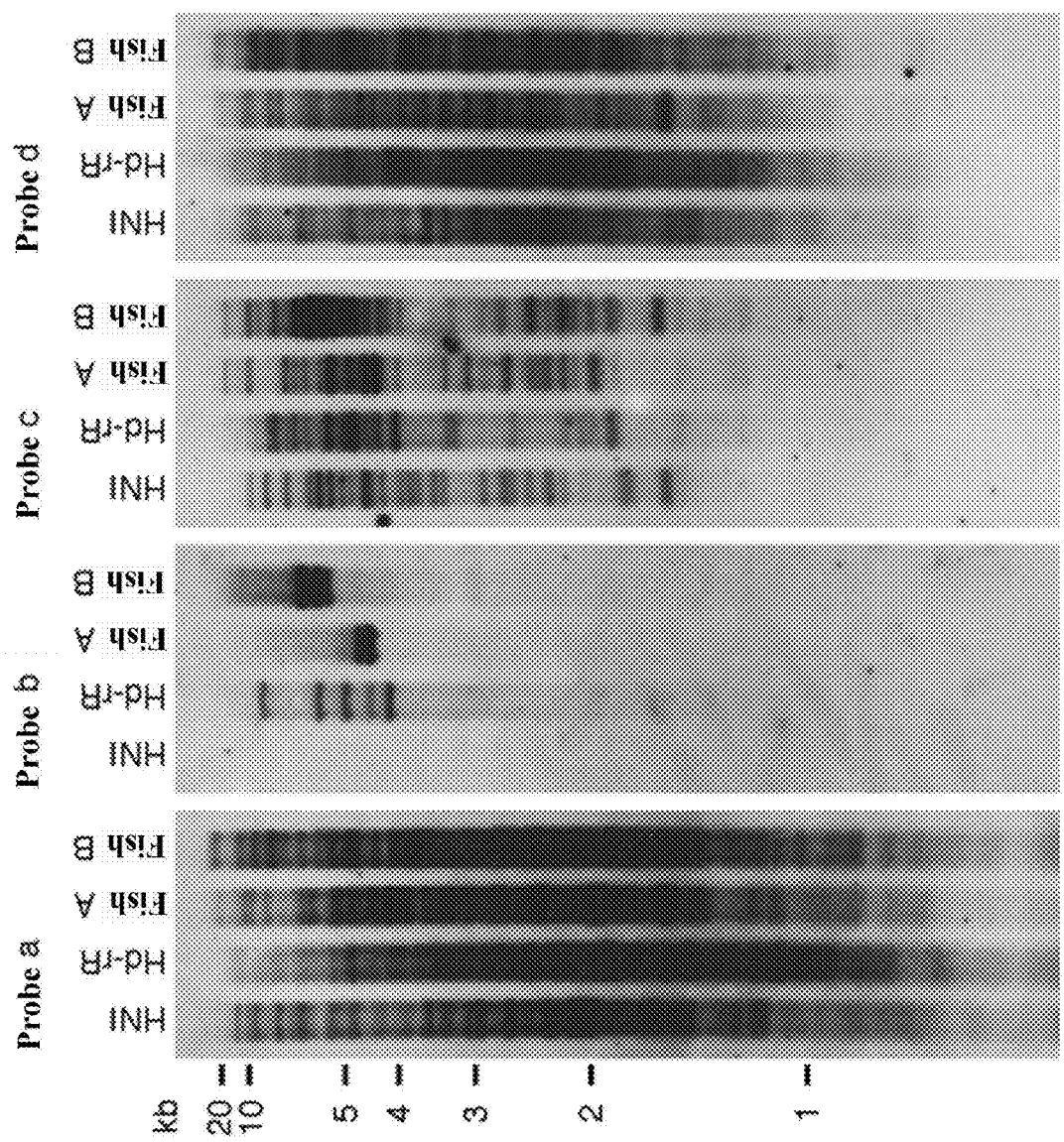
FIG. 5 shows Southern blots including copies of Tol1 in medaka fish genomes. Genomic DNA was extracted from each one of fish A, fish B, HNI, or Hd-rR. HNI and Hd-rR are commonly-used inbred medaka fish lines. 8.0 µg of genomic DNA was prepared for each fish, completely digested with restriction enzyme PvuII, electrophoresed in a 1.0% agarose gel and transferred to a nylon membrane, which was then hybridized with probes "a" to "d" (see FIG. 2 for positions). Positions of molecular weight markers are shown. These results indicate that internal deletion is present in most copies of Tol1 present in medaka fish genomes.

The previously-performed database search suggested that, in medaka fish genomes, there is greater variability in the Tol1 internal region when compared to the Tol1 end regions. Southern blot analysis using various medaka fish lines confirmed this. Probes that corresponded to various parts of full-length Tol1-L1 were used. When a probe that hybridized to an end region was used, 100 bands or more appeared; on the other hand, when a probe for an internal region was used, the number of bands was 0 to 5 (FIG. 5). Such a phenomenon is commonly observed also in Activator element of corn (Cited document 19), p element of *Drosophila* (Cited document 20), and other DNA type elements. It is generally accepted that internal deletion can generate a nonautonomous element from an autonomous element (Cited documents 19 and 20). This may also be applicable to Tol1.

(6) Demonstration of Tol1 Transposition in Mammalian Cells

Figure 6:
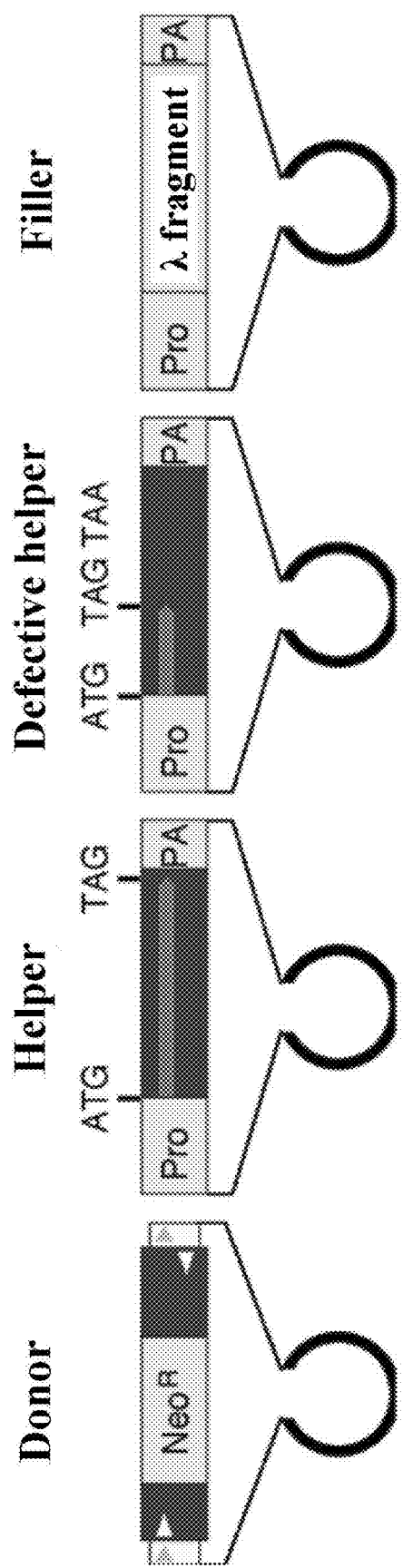
FIG. 6 shows plasmids used for measurement of transposition frequency. Tol1-tyr (GenBank Accession No. D42062, SEQ ID NO: 10) was amplified from genomic DNA of fish A with 8 bp of adjacent TSD (CCTTTAGC (SEQ ID NO: 13)) and inserted into plasmid pUC19 to form a clone. Subsequently, a fragment of plasmid pCMV-Tag1 (bases 1675 to 3474 of the nucleotide sequence of GenBank Accession No. AF025668, SEQ ID NO: 18) was amplified by PCR and inserted into a SalI recognition site (bases 706 to 711 of the nucleotide sequence of GenBank Accession No. D42062) in Tol1-tyr. A neomycin-resistant gene is included in this fragment of pCMV-Tag1. The resulting plasmid was used as a donor plasmid. A helper plasmid was prepared by inserting bases 31 to 2817 (SEQ ID NO: 19) of Tol1 cDNA (nucleotide sequence of GenBank Accession No. AB264112, SEQ ID NO: 3) into a multicloning site of plasmid pCI. This multicloning site was present between a CMV promoter and a poly-A additional signal. A defective helper plasmid was prepared by introducing a mutation by PCR. Bases 996 to 1001 of the helper plasmid are ATGAAA, which corresponds to amino acids, methionine and lysine. Using PCR, ATGAAA was mutated to TAGTAA. This mutation resulted in sequential generation of two termination codons near the middle of a transposase's ORF. A filler plasmid was prepared by inserting 2.8 kb of a λDNA fragment into plasmid pCI instead of transposase cDNA.
Figure 7:
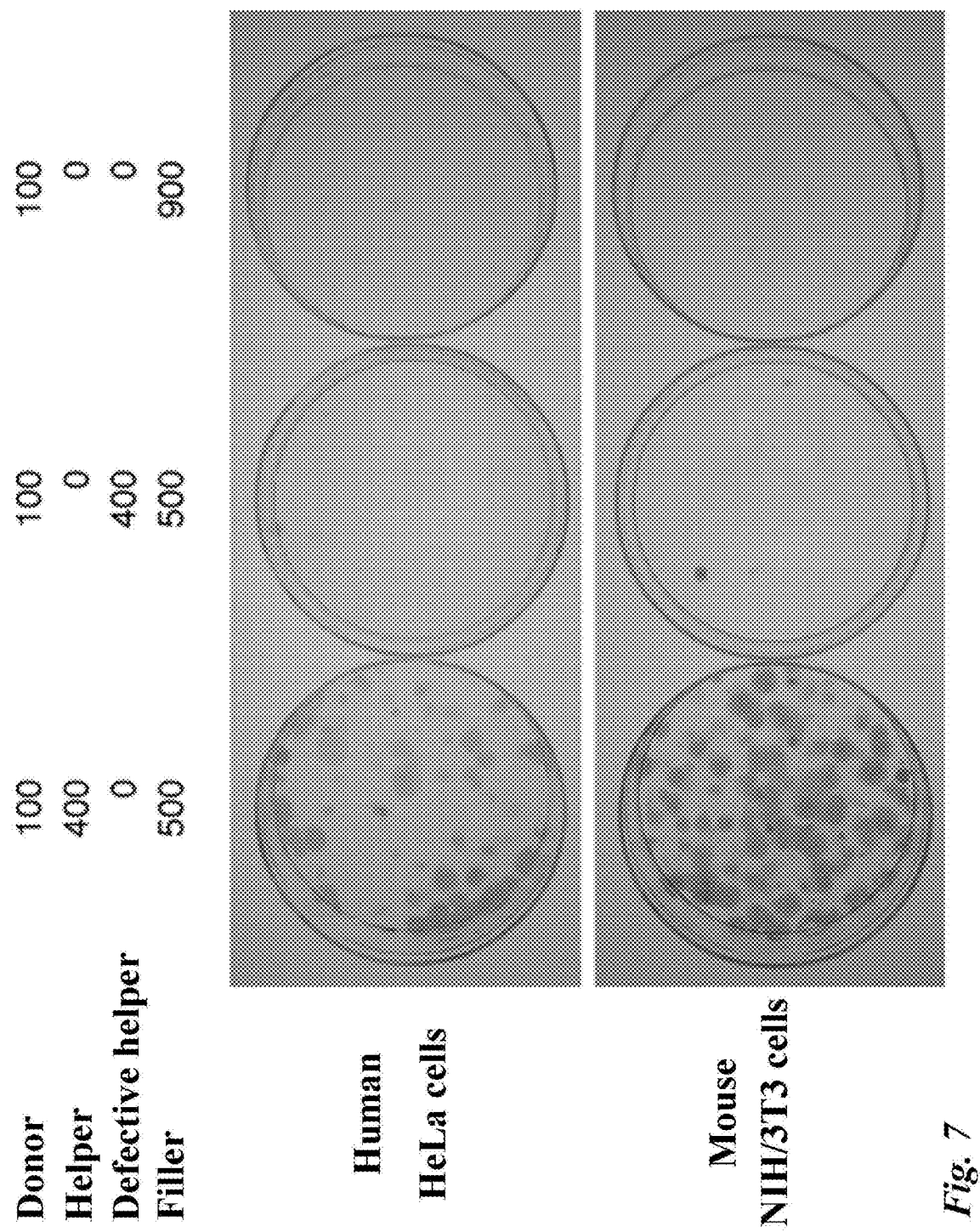
FIG. 7 shows transposition of Tol1 in mammalian cells. A donor plasmid and a helper plasmid, a donor plasmid and a defective helper plasmid, or only a donor plasmid was transfected into HeLa cells or into NIH/3T3 cells. Filler plasmids were transfected as necessary. Selection for transfectants in G418 was then carried out. Pictures of 60 mm-dishes dyed with Giemsa stain solution are shown. A large number of G418-resistant colonies were generated only when a donor plasmid and a helper plasmid were transfected.

To determine whether Tol1 ORF encodes a transposase and whether it can mediate a transfer reaction of DNA intervening a Tol1 element, a donor plasmid (hereinafter also referred to as a "donor") and a helper plasmid (hereinafter also referred to as a "helper") were prepared. The donor plasmid had 1.9 kb of Tol1-tyr with a neomycin-resistant gene incorporated within Tol1-tyr. The helper plasmid had Tol1 ORF. A CMV promoter was connected upstream to the ORF, and in the same manner, a poly-A additional signal was connected to the downstream side for stabilization (FIG. 6). A defective helper plasmid, which served as a negative control, was prepared. The defective helper plasmid was prepared by replacing two codons of the internal ORF with stop codons. Further, a filler plasmid having an irrelevant DNA fragment but of the same length as Tol1 ORF was prepared. The filler plasmid was used so that the same amount of exogenous DNA was introduced in each experiment. These plasmids were combined and introduced into human HeLa cells or mouse NIH/3T3 cells. Cells that had acquired G418 resistance were selected. A large number of G418-resistant colonies were generated in cells introduced with a donor plasmid and a helper plasmid, compared to cells introduced with a donor plasmid and a defective helper plasmid or a donor plasmid and a filler plasmid (FIG. 7). To confirm that G418 resistance resulted from transposition (incorporation) of Tol1 into a target cell's genome, a DNA fragment containing Tol1 was cloned from a G418-resistant cell introduced with a donor plasmid and a helper plasmid. Then, the nucleotide sequences of a Tol1 end region and a flanking portion were examined. When eight clones were examined, their aligned sequences were significantly different (FIG. 8). Each of the eight clones had two 8 bp target site duplications (TSD). This indicates that incorporation of a Tol1 portion of the donor plasmid into a chromosome results from the transfer reaction. These data demonstrated that Tol1 ORF encodes a functional Tol1 transposase.

(7) Comparison Between Transposition Frequencies of Tol1 and Tol2

Figure 9:
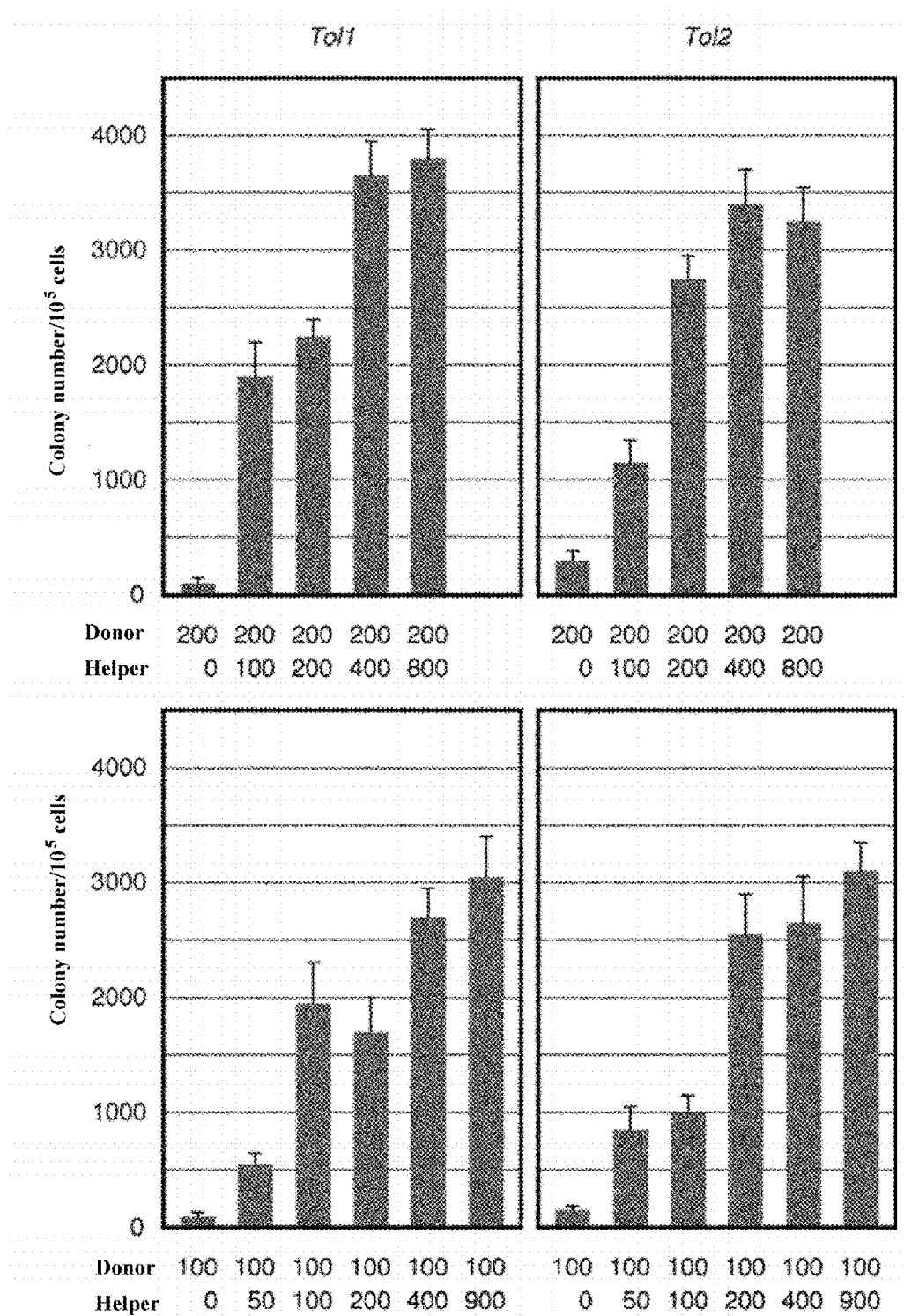
FIG. 9 shows transposition frequencies of Tol1 and Tol2 in HeLa cells. Various amounts of a donor plasmid and a helper plasmid were combined, and transposition frequencies were measured for Tol1 (left panel) or for Tol2 (right panel). A donor plasmid of Tol2 was prepared based on a donor plasmid of Tol1. Specifically, the Tol1 left arm of the Tol1 donor plasmid was replaced with bases 1 to 755 of the Tol2 nucleotide sequence (GenBank Accession No. D84375, at the World Wide Web (www) ncbi.nlm.nih.gov/Genbank/index.html, SEQ ID NO: 9), and the right arm of the donor plasmid of Tol1 was replaced with bases 4147 to 4682 of the Tol2 nucleotide sequence. pHel03, as described in Cited document 33, was used as the helper plasmid of Tol2. The total amount of plasmid DNA was 1,000 ng in each experiment. Amounts of donor plasmid or helper plasmid are shown below the graphs. When the total amount of donor plasmid and helper plasmid was less than 1,000 ng, supplementary amounts of filler plasmid was added (the amount of filler plasmid used is omitted from the figure). Average values (±standard error) of the numbers of colonies found for three independent measurements are shown.

Transposition frequencies of Tol1 and Tol2 were examined using HeLa cells. A donor plasmid and a helper plasmid, for each of Tol1 and Tol2, were prepared and co-introduced into the HeLa cells. Ratios of a donor plasmid and a helper plasmid were set within the range of 1:0.5 to 1:9 (when the amount of donor is 100 ng) and within the range of 1:0.5 to 1:4 (when the amount of donor is 200 ng). Within these ranges, transposition frequencies for either element showed positive correlation to the amount of helper plasmid (FIG. 9). The "net colony number" was found by subtracting the "colony number with no helper" from an "observation value of the colony number." The maximum "net colony number" of Tol1 was 3780−120=3660 (donor 200 ng, helper 800 ng) and that of Tol2 was 3,393−287=3,106 (donor 200 ng, helper 400 ng). The ratio of maximum values (Tol1 maximum value/Tol2 maximum value) was 1.18. Thus, the maximum transposition frequencies of Tol1 and Tol2 were equivalent.

(8) Noninterference Regarding Transposition Induction of Tol1 and Tol2

Both Tol1 and Tol2 are hAT family elements and are present in genomes of the same fish species. Thus, it was examined whether a Tol1 transposase induces Tol2 transposition and whether a Tol2 transposase induces Tol1 transposition. In this experiment, a 1:4 ratio of a donor plasmid and a helper plasmid was introduced into HeLa cells. It was shown in past experiments that this ratio causes high frequency transposition.

Figure 10:
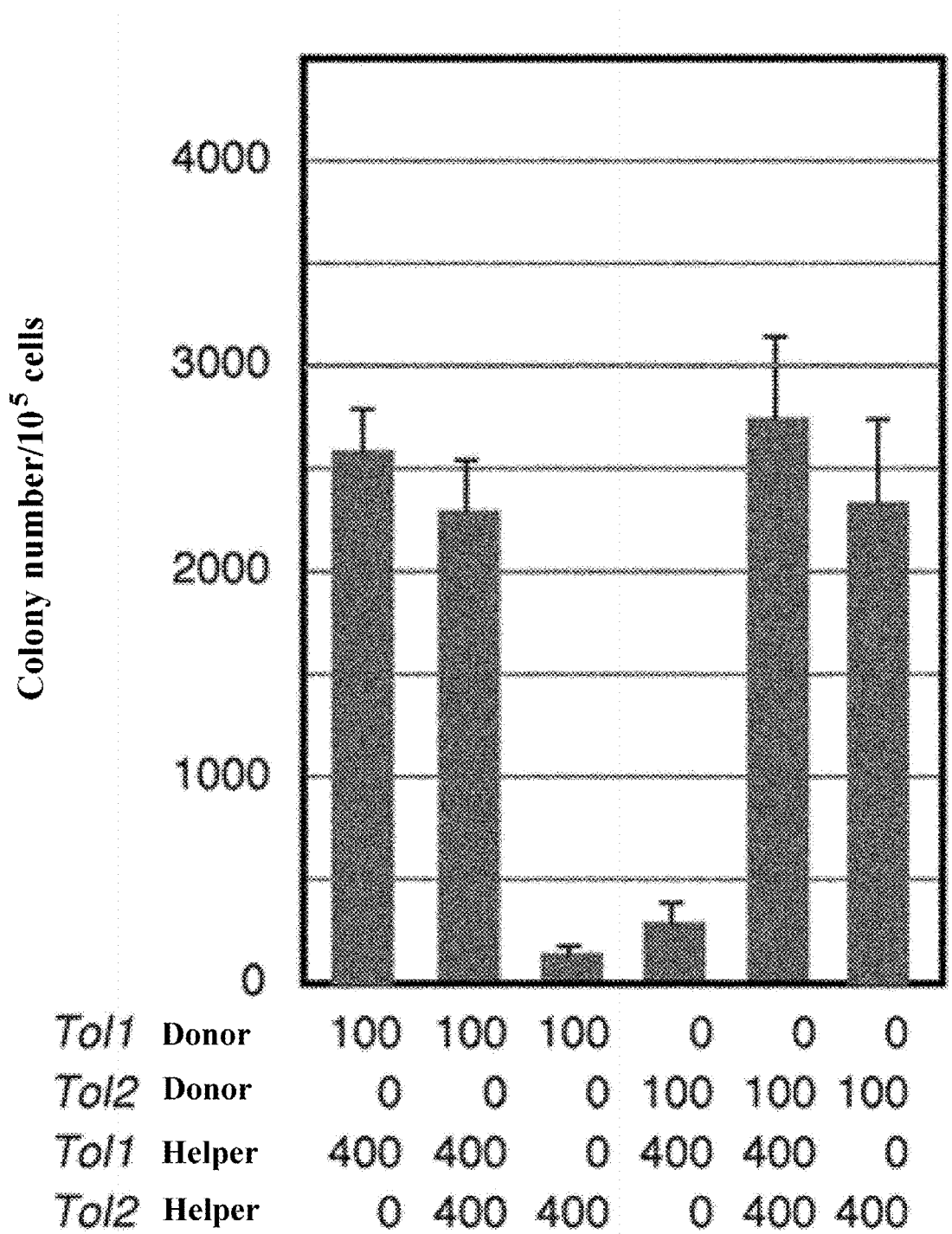
FIG. 10 shows mutual effects between Tol1 and Tol2 in HeLa cells. Plasmid DNAs were combined and transposition frequencies were measured. Six combinations were tested as described below the graph. In each experiment, the total amount of plasmid DNA was 1,000 ng. The amount of the filler plasmid used is omitted from the figure. Tol1 transposase and Tol2 transposase are capable of transferring only their own corresponding elements.
Figure 14:
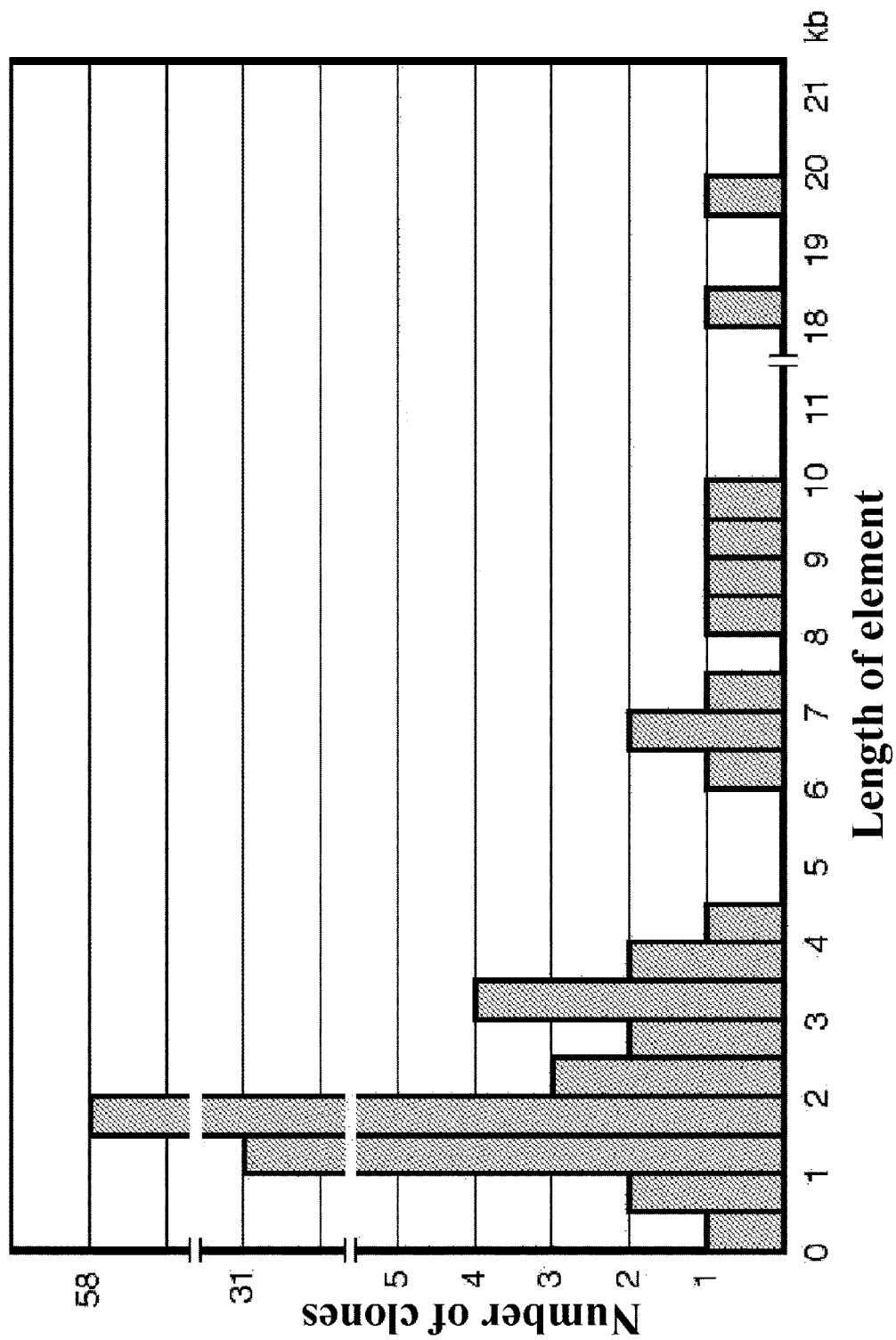
FIG. 14 shows variations in the length of naturally-occurring Tol1 elements. PCR was used to amplify an internal Tol1 portion from 130 clones whose genomic DNA hybridized with both Tol1 end regions. The primers used were 30 bp of Tol1's left end (1st to 30th bases) and 30 bp of its right end (1855th to 1826th bases). A bacteria colony was used as template. PCR conditions were as follows: [94° C., 2 minutes], 30×[94° C., 20 seconds; 64° C., 20 seconds; 72° C., 2 minutes], and [72° C., 5 minutes]. The PCR products were electrophoresed in a 1% agarose gel and lengths of the products were recorded. For clones in which amplification had not occurred using the above PCR conditions, PCR was performed with a longer elongation step (8 minutes instead of 2 minutes). Then, the PCR products were electrophoresed in a 0.8% agarose gel and the length of the products were recorded. In a third PCR condition, a 20 minute elongation step was used and the reaction products were electrophoresed in a 0.6% agarose gel. The lengths of 114 Tol1 elements were determined; their distributions are illustrated in the figure.

The experimental result clearly showed that the Tol1 transposase does not induce Tol2 transposition and that the Tol2 transposase does not induce Tol1 transposition (FIG. 10). Thus, each of the two transposases functions only for its corresponding elements.

3. Discussion

Two types of transposition factors, which are known as transposable elements, are present in genomes of vertebrates; both of which have transposable activities. The transcription factors are Tzf element of zebrafish and Tol2 element of medaka fish. Although transposition of a Tol1 element not directly demonstrated at the time Tol1's discovery, apparently the insertion of a Tol1 element was responsible for mutation of the albino line (subline A) of medaka fish (Cited document 21). Since almost all known copies include internal disruptions or deletions, it was expected that other copies are present in genomes. Here, the present inventors identified an intact Tol1 element from a database search and found that it can cause transposition at a high frequency. Furthermore, the present inventors characterized a subline (subline B) that has a unique mosaic pigmentation.

Tol1 and Tol2 both belong to the hAT family. However, there are large differences in their molecular structure and their distribution among species. Many Tol1s have internal deletion of various sizes; repeat sequences having homology in Tol1 are widely distributed in members of the *Oryzias* genus (Cited document 10). Unlike Tol1s, Tol2s have uniform sequences and structures and are observed only in medaka fish species (*O. latipes*) and its related species (*O. curvinotus*) (Cited document 23). The inventors speculate that Tol1 has been present in the *Oryzias* genus for a long time; on the other hand, Tol2 recently emerged in the genome of a line related to medaka fish (Cited document 23). It is likely that the two elements coexist in modern-day medaka fish by chance, and a sufficient time have passed; therefore, separate transfer reaction lines are now established.

Mosaic pigmentation observed in Tol1-tyr is similar to the unstable body color mutation that was recently discovered by the present inventors in another gene (Cited document 9). In a line showing unstable body color, it was found that Tol2 excision from a tyrosinase gene occurs at high frequency and Tol2 insertions occur in various sites of a genome. Transposition burst, the bursting of active transposition by a transposable element, is frequently observed in non-vertebrate model organisms. The discovery of transposition burst by Tol2 medaka fish was the first example of transposition burst in vertebrates. Presently, examination of insertion of Tol1 is difficult. This is because there are more copies of Tol1 in medaka fish genomes than copies of Tol2 and it is expected that such examination beyond the capabilities of the currently-used analysis methods. If transposition burst also occurs in Tol1, it is possible that a DNA-type element greatly influenced genomic evolution of vertebrates. Determining the degree of this influence on evolution is required.

Tol1 was believed to have lost its functions until a mosaically-pigmented medaka fish was discovered. This is because, although over 100 Tol1 copies had been examined, none resembling a gene had been found (Cited document 10). From human and other genome sequencing projects, it has been found that a considerable number of DNA transposable elements exists in vertebrate genomes. However, most of these elements have lost their transposition activities (Cited document 4). Prior to the present invention, the inventors questioned whether there existed a DNA transposable elements capable of reactivation. Thus, it is significant that the above-described Southern Blot analysis revealed that a potential autonomous copy exists in subline A.

In a comparison experiment of transposition frequencies of Tol1 and Tol2, amounts of introduced donor plasmid and helper plasmid were varied. There, the total weight of plasmid introduced did not vary. However, each plasmid introduced had a different molecular mass; thus, the molar ratios of introduced Tol1 or Tol2 plasmids, that is, the number of molecules, was not the same between conditions. More specifically, the length a transposable element in the donor plasmid and the length of a cDNA in the helper plasmid differed between the two elements. For the donor plasmid, the lengths of the whole element, including the neomycin-resistant gene, were 3.7 kb in Tol1 and 3.1 kb in Tol2. The lengths of the encoding regions in the helper plasmid were 2.8 kb in Tol1 and 2.0 kb in Tol2 (see descriptions of FIGS. 5 and 9). Although there were such differences, comparative transposition efficiencies of Tol1 and Tol2 could be determined from the experimental results. Importantly, the maximum transposition frequency for Tol1 was equal to the maximum transposition frequency for Tol2. Tol2 is an element recently used in genetic modification systems in vertebrates, such as gene introduction (Cited document 13), mutagenesis (Cited document 14), and trapping of genes and promoters or enhancers (Cited document 15). Accordingly, it is likely that Tol1 has similar capabilities. It is extremely important that the two types of elements do not influence each other's transposition. Existence of two DNA introduction systems capable of independent control is particularly beneficial when co-introduction of two desired DNAs into one cell line or organism is necessary. It is also envisaged that a first introduced DNA is transferred by supplying a transposase of an element corresponding to the first DNA and not supply a transpose of an element corresponding to a second DNA.

While both of Tol1 and Tol2 are elements in the hAT family, Sleeping Beauty and Frog Prince, which were derived from fish and frog genomes, belong to the mariner/Tc1 family. piggyBac, which was derived from an insect genome, belongs to another family. A significant difference among these transposable element families lies in the size of an element. Most of the mariner/Tc1 family elements are 1 to 2 kb long, and piggyBac are 2.5 kb long. On the other hand, a typical full-length element in the hAT family is 4 to 6 kb long. Since, in many elements, there is a negative correlation between element length and transposition frequency (Cited document 24), having a large element belonging to the hAT family would be useful for transferring a large DNA fragment. In fact, the present inventors reported that Tol2, which is up to 9.0 kb long, can be transferred (Cited document 13). In addition to an element's length, there is another difference among the transposable element groups, namely, "restriction accompanied by excessive expression." When a transposase exists in an excessive amount, transposition frequencies decrease in Sleeping Beauty (Cited document 24), mariner of *Drosophila* (Cited document 25), and piggyBac (Cited document 25). However, such a phenomenon did not appear to occur in Tol1 or Tol2. Others studying Tol2 reported similar results (Cited document 26). It is potentially very useful that two hAT family elements, which independently function and have high transposition frequencies, can be used for genetic manipulation in vertebrates.

CITED DOCUMENTS

1. Dombroski B. A., Mathias S. L., Nanthakumar E., Scott A. F., Kazazian H. H., Jr (1991) Science 254: 1805-1808.
2. Burden A. F., Manley N. C., Clark A. D., Gartler S. M., Laird C. D., Hansen R. S. (2005) J Biol Chem 280: 14413-14419.
3. Li X., Scaringe W. A., Hill K. A., Roberts S., Mengos A., Careri D., Pinto M. T., Kasper C. K., Sommer S. S. (2001) Hum Mutat 17: 511-519.
4. International Human Genome Sequencing Consortium (2001) Nature 409: 860-921.
5. Lam W. L., Lee T. S., Gilbert W. (1996) Pr°C Natl Acad Sci USA 93: 10870-10875.
6. Koga A., Suzuki M., Inagaki H., Bessho Y., Hori H. (1996) Nature 383: 30.
7. Bryan G., Garza D., Hartl D. L. (1990) Genetics 125: 103-114.
8. Brookfield J. F. (2004) Curr Biol 14: R344-345.
9. Koga A., Iida A., Hori H., Shimada A., Shima A. (2006) Mol Biol Evol 23: 1414-1419.
10. Koga A., Sakaizumi M., Hori H. (2002) Zoolog Sci 19: 1-6.
11. Koga A., Inagaki H., Bessho Y., Hori H. (1995) Mol Gen Genet 249: 400-405.
12. Tsutsumi M., Imai S., Kyono-Hamaguchi Y., Hamaguchi S., Koga A., Hori H. (2006) Pigment Cell Res 19: 243-247.
13. Koga A., Hori H., Sakaizumi M. (2002) Mar Biotechnol 4: 6-11.
14. Johnson Hamlet M. R., Yergeau D. A., Kuliyev E., Takeda M., Taira M., Kawakami K., Mead P. E. (2006) Genesis 44: 438-445.
15. Choo B. G., Kondrichin I., Parinov S., Emelyanov A., Go W., Toh W. C., Korzh V. (2006) BMC Dev Biol 6: 5.
16. Ivics Z., Hackett P. B., Plasterk R. H., Izsvak Z. (1997) Cell 91: 501-510.
17. Miskey C., Izsvak Z., Plasterk R. H., Ivics Z. (2003) Nucleic Acids Res 31: 6873-6881.
18. Wu S. C., Meir Y. J., Coates C. J., Handler A. M., Pelczar P., Moisyadi S., Kaminski J. M. (2006) Proc Natl Acad Sci USA 103: 15008-15013.
19. Rubin E., Levy A. A. (1997) Mol Cell Biol 17: 6294-6302.
20. O'Hare K., Rubin G. M. (1983) Cell 34: 25-35.
21. Koga A., Hori H. (1997) Pigment Cell Res 10:377-831.
22. Koga A., Hori H. (1999) Genet Res 73: 7-14.
23. Koga A., Shimada A., Shima A., Sakaizumi M., Tachida H., Hori H. (2000) Genetics 155: 273-281.
24. Geurts A. M., Yang Y., Clark K. J., Liu G., Cui Z., Dupuy A. J., Bell J. B., Largaespada D. A., Hackett P. B. (2003) Mol Ther 8: 108-117.
25. Hartl D. L., Lozovskaya E. R., Nurminsky D. I., Lohe A. R. (1997) Trends Genet. 13: 197-201.
26. Kawakami K., Noda T. (2004) Genetics 166: 895-899.
27. Tomita H. (1975) in Medaka (Killifish): Biology and Strains, ed Yamamoto T. (Yugakusha Publ., Tokyo), pp. 251-272.
28. Rubin E., Lithwick G., Levy A. A. (2001) Genetics 158: 949-957.

Example 2

Using an autonomous copy of Tol1 element (Tol-L1, length 4355 bp, DDBJ/EMBL/GenBank Accession No. AB288091, SEQ ID NO: 4) and a transposable enzyme gene (length 2900 bp, DDBJ/EMBL/GenBank Accession No. AB264112, SEQ ID NO: 3) (Example 1), a Tol1 element is now available as a genetic tool for use in mammals.

A common feature of transposable elements is a reduction in transposition frequency as the length of an element decreases. Thus, "loading ability" is important when selecting an element. The "loading ability" herein means the "maximum length of a DNA fragment that can be carried by an element." Tol1 element is expected to be highly useful in this regard. First, the Tol1 element belongs to the hAT family. The hAT family is a group of transposable elements represented by hobo element of *Drosophila*, Activator element of corn, and Tam3 element of snapdragon (Cited documents 2 and 16). A particular characteristic of this family is a longer whole (complete) length as compared to other common element families. Specifically, while the hAT family elements have lengths of 4 to 6 kb, most elements in the mariner/Tc1 family are 1 to 2 kb and piggyBAac element are 2.5 kb, which are comparatively short. Second, before the current study, a preliminary examination conducted by the present inventors suggested that Tol1 element exceeding 15 kb exists in medaka fish genomes. Based on these findings, the present inventors inferred that Tol1 element transfers even if the whole length exceeds 15 kb. Tol2 element is also a hAT family element (Cited document 7). However, copies of this element have no structural differences, and almost all copies are 4.7 kb long. Although the present inventors have made large-scale investigations on naturally existing Tol2 element, so far, an element longer than 4.7 kb has not been found (Cited documents 7 and 8).

Here, the inventors investigated the length of naturally-existing Tol1 element. It was found that copies of about 18 kb and about 20 kb in length exist. Consequently, the Inventors set out to develop a gene introduction vector are able to incorporate long DNA fragments into a chromosome. First, an internal region, which is unnecessary for a transfer reaction, was removed from a 1.9 kb element, thereby producing a short vector having a whole length of 0.3 kb. Then, another DNA fragment was inserted into this vector and this second vector served as a basis for preparing Tol1 elements having various lengths. Each Tol1 element was then incorporated into a cell by lipofection. Subsequently, G418 selective culturing was performed and the residual colony number was counted. This number was used to calculate a transposition frequency (see Example 1 for the experimental technique). However, since lipofection may have affected the efficiency of DNA incorporation, a control that excluded the influence of the incorporation efficiency was conducted. The control was to compare efficiency when the sizes of whole plasmids were the same, even when the lengths of Tol1 elements inserted therein differed. This revealed that even when Tol1 element was as long as 22.1 kb, the Tol1 element transferred efficiently. Indeed, this is the longest DNA transposable element reported in mammals.

1. Materials and Methods (1) Genomic Library

A genomic library of medaka fish was prepared in a previous study (Cited document 10). The library was used to obtain a clone of genomic DNA containing Tol1 element. The original genomic DNA of medaka fish for the library was extracted from an albino medaka fish that had partial melanin pigmentation on its skin and eyes. The vector was fosmid pCC1FOS™ (EPICENTRE Biotechnologies, Madison, Wis., USA), which can accommodate 33 to 48 kb of mechanically-sheared DNA.

(2) Plasmid

Two types of plasmids, i.e. a donor plasmid and a helper plasmid, were used. Tol1 element is excised from the donor plasmid and incorporated into a chromosome due to action of a transfer enzyme encoded by the helper plasmid.

Figure 15:
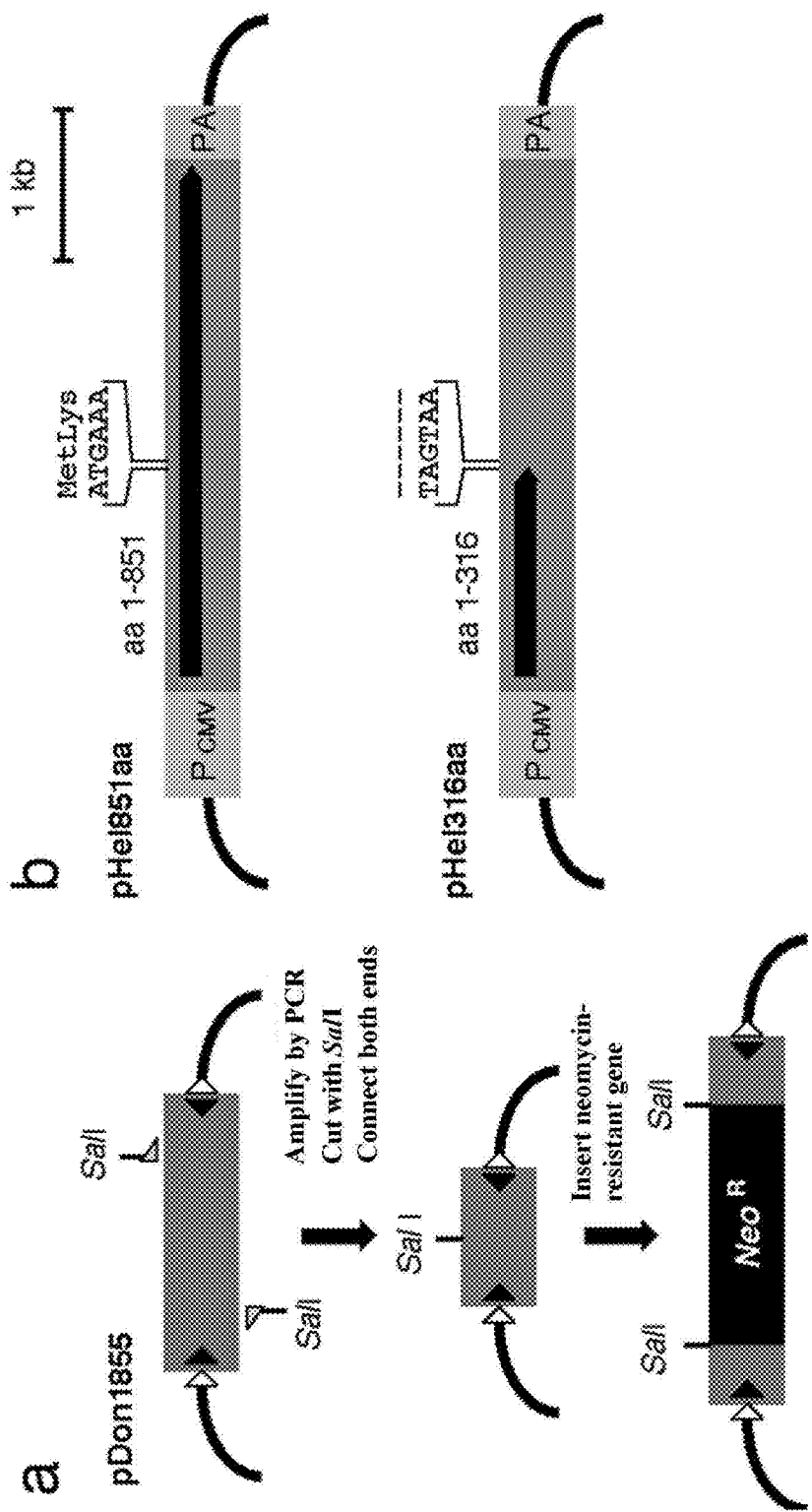
FIG. 15 shows a donor plasmid and a helper plasmid.

The structure of the donor plasmid used here is shown in FIGS. 15 and 17. The helper plasmid was the same as used in Example 1; its basic structure is shown in FIG. 15. A defective helper plasmid was also prepared. The defective helper acts as a control since it lacks an active transfer enzyme.

(3) Transposition Frequency Measurement System

Human HeLa cells and Mouse NIH/3T3 cells were cultured in a DMEM medium containing 10% FBS (fetal bovine serum). The culture temperature was 37° C. and the $CO_2$ concentration was 5.0%.

$2\times10^5$ cells were seeded per well in a 12-well plate (diameter 22 mm). After 24 hours, 100 ng of the donor plasmid and 900 ng of the helper plasmid were added to each well and were incorporated into the cells using a Lipofectamine™ LTX reagent (Invitrogen Corp., Carlsbad, Calif., USA). After 8 hours, the cells were washed twice with PBS and the medium was replaced with fresh media, which lacked plasmids. After 24 hours, the cells were separated from the dish with trypsin and suspended in 2.0 ml of fresh media. Mediums containing G418 at a concentration of 500 μg/ml was added to dishes of different sizes (35 mm, 60 mm, and 90 mm), and 400 μl of a cell suspension was added thereto. After 12 days of G418 selection, cells were fixed with 20% formalin and stained with Giemsa stain. A dish having about 100 colonies was selected from the dishes and the colony number was counted. The colony number per $10^5$ cells initially seeded was determined based on the counted number and dilution factor. The above-described procedure is the steps included in one trial. Such a trial was performed three times for each combination of donor plasmid and helper plasmid.

(4) Technique of Molecular Level Operation

This study is an extension of the study shown in Example 1. Adjustment of genomic DNA, PCR, cloning of PCR products, determination of nucleotide sequences, and colony hybridization were carried out by the same methods and procedures. However, for PCR, LA Taq™ DNA Polymerase (Takara Bio Inc.) was used here, since it efficiently amplifies long stretches of DNA, rather than of Ex Taq® (Takara Bio Inc., Otsu, Japan) as used previously. PCR conditions are described in the corresponding section.

2. Experimental Results (1) Mutation of Length Shown in Tol1 Copies 100 to 200 copies of Tol1 exist in a medaka fish genome; interestingly, the lengths of the copies are not uniform (Cited document 9). To determine length variations, a genomic library screen was performed with particular attention to the identification of long copies. Two hybridization screens were carried out and a chromosome fragment containing both end regions of Tol1 was recovered. In the first screen, a clone which hybridized to the left end region (1st to 500th bases of SEQ ID NO: 10) of Tol1-tyr was identified. $4\times10^4$ colonies (this number corresponds to twice the DNA content of a haploid genome) were screened using a probe labeled with alkaline phosphatase. In the primary screen, 161 positive signals were detected. A secondary screen was performed on the 161 colonies identified in the primary screen. Here, the right end region of Tol1-tyr (1356th to 1855th bases of SEQ ID NO: 10) was used as a probe. In the secondary screen, 130 of the 161 colonies had positive signals.

Figure 16:
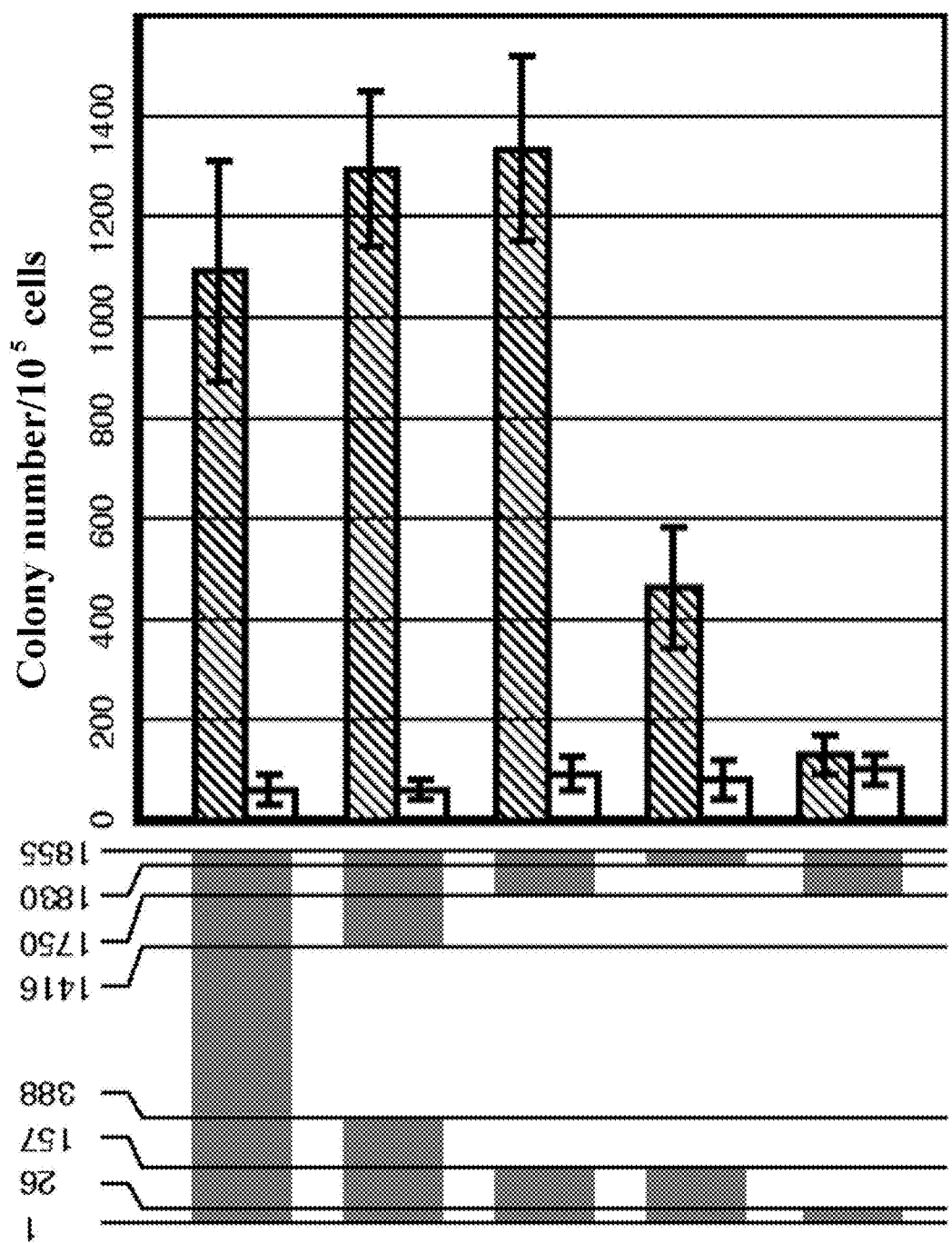
FIG. 16 shows transposition frequencies of Tol1 elements having internal deletions. Only Tol1 arms are illustrated (not to scale) on the left of the figure. Plasmids containing these internally-deleted Tol1 elements were used as donor plasmids and transfected into cells along with the complete helper plasmid pHel851aa (hatched rectangle) and the defective helper plasmid pHel316aa (white rectangle). Transposition frequencies were measured. Average colony numbers from three measurements are shown in the graph. Horizontal lines in the graph are standard errors of the mean.

The clones obtained by the screens were subjected to PCR using primers that recognized both end regions of Tol1. This amplified a Tol1 portion contained in each clone. Amplification was observed in 114 out of 130 clones. The distribution of element lengths was approximately mound-shape with a sharp peak at 1 to 2 kb (FIG. 16). It is particularly notable that clones 18 kb and 20 kb long were identified. As shown later, Tol1 element transfers independent of its internal nucleotide sequences, provided that the element has end regions. Therefore, it was expected that the two long Tol1 elements identified would have transferring ability.

(2) Transposable Activity of Short Clones of Tol1

It has been observed that, as long as a transfer enzyme is present, a DNA transposable element retains its transposable activity even though the element lacks a portion of its internal sequence (Cited document 15) The Tol1-tyr element, which is 1.9 kb long, transfers as long as a transfer enzyme is added, although Tol1-tyr lacks a portion of the internal sequence of Tol1-L1 element, which is 4.4 kb long (Cited document 10). Since many elements shorter than 1.9 kb also exist in a medaka fish genome (FIG. 16), it was considered likely that the 1.9 kb long element contains a portion of the element that is unnecessary for transposition.

Thus, many shorter clones were prepared and their transposable activities were examined. The method for measuring the number of colonies used in Example 1 was used here. To prepare shorter elements, a PCR primer was used that was orientated outward at an end region of Tol1-tyr. First, an arm of Tol1 and a plasmid having the arm were PCR amplified as one sequential fragment and both ends of the fragment were connected. Then, a neomycin-resistant gene was incorporated into the connected portion (FIG. 15). The resulting donor plasmid was allowed to be incorporated into cultured mouse cells together with a complete or defective helper plasmid (FIG. 15). One clone comprising a left arm with 157 bp and a right arm with 106 bp showed a transposition frequency equal to or greater than that of Tol1-tyr (FIG. 16). Either arm in this clone was further shortened; when an arm was 26 bp long, transposable activity was extremely decreased, and in some cases, transposable activity was lost (FIG. 16)

(3) Preparation of Short Vector Having Cloning Site

A new clone was prepared based on the previous experimental results. The new clone, pDon263Mcs, has 157 bp of the left arm and 106 bp of the right arm of Tol1 element. The new clone, between the arms, had a multiple cloning site (MCS) including the restriction enzyme recognition sites for six frequently-used restriction enzymes (i.e., BamHI, EcoRI, EcoRV, KpnI, PstI, and XbaI) (FIG. 17). The new clone also included a HindIII site outside of the Tol1 element. The HindIII site allows accurate measurement of a transposition frequency, as described below.

(4) Preparation of a Plasmid Having a Constant Whole Length and Having Tol1 Element with Different Sizes in the Inside Thereof A first DNA fragment having a length of "x" kb ("x"=0, 5, 10, 15, or 20) and a second DNA fragment having a length of "y" kb ("y"=20−"x") were prepared using PCR. The first DNA fragment was inserted into an EcoRI site of pDon263McsNeo (inside Tol1) and the second DNA fragment was inserted into the HindIII site (outside Tol1) (FIG. 17). Clones thus prepared were named pDon263McsNeoExHy. In Don263McsNeoExHy, a Tol1 arm was 0.3 kb long, a neomycin-resistant gene was 1.8 kb long, and vector backbone was 2.7 kb long. Accordingly, the distance from the left end to the right end of Tol1 in pDon263McsNeoExHy was ("x"+2.1) kb. The size of the plasmid on the whole was 24.8 kb regardless of the value of "x".

It is known that a plasmid's size influences its incorporation efficiency by lipofection. Thus, a second DNA fragment was inserted outside Tol1 in addition to first DNA fragment which was inserted inside Tol1. This standardized the size of each plasmid which negated an influence a plasmid's size would have on incorporation efficiency. Thereby, precise comparison of transposition frequencies among donor plasmids with different amounts of Tol1 and/or insert became possible.

(5) Comparison of Transposition Frequencies

Figure 18:
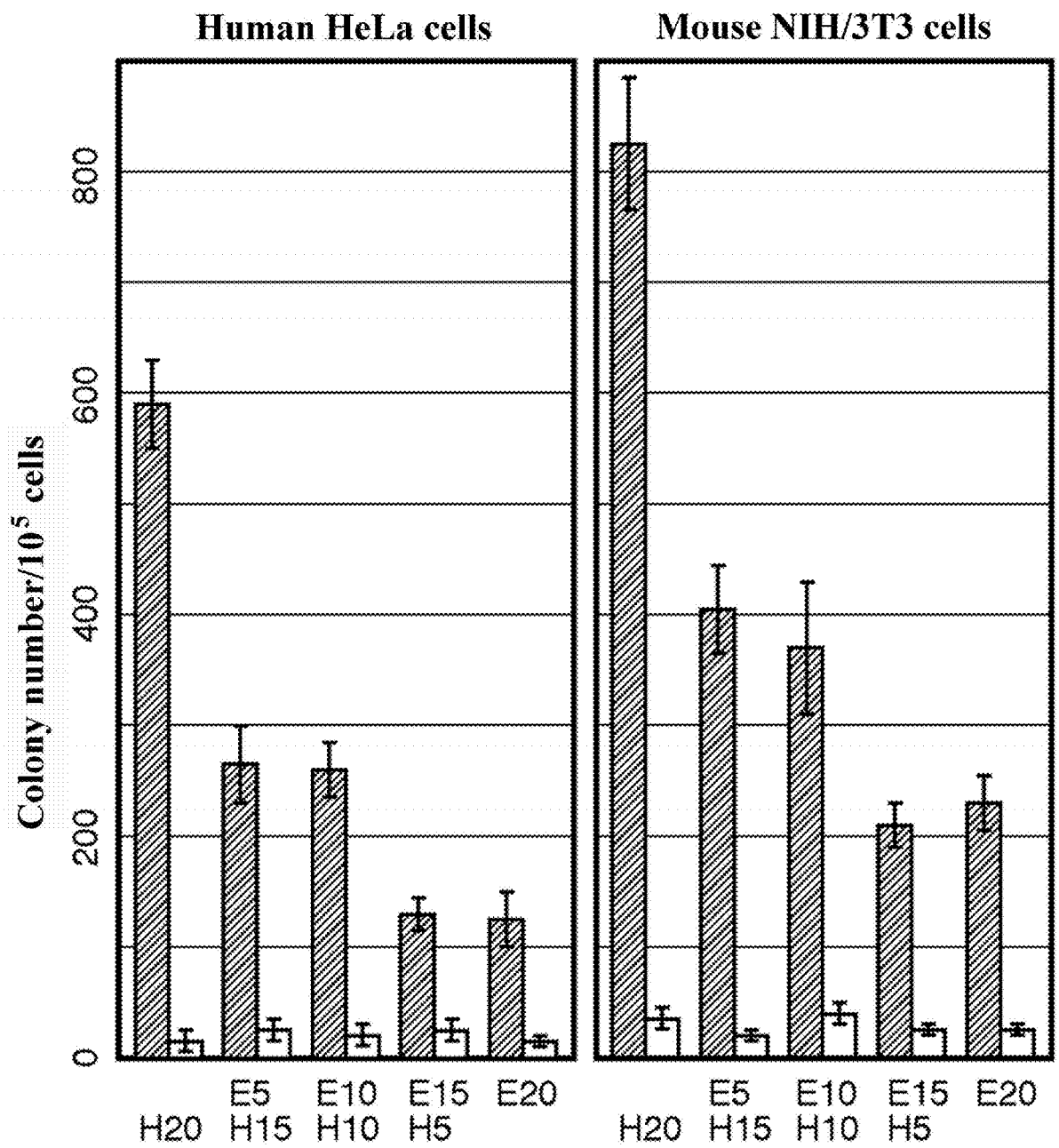
FIG. 18 shows transposition frequencies of long Tol1 elements. Transposition frequencies were measured for cells transfected with the complete helper plasmid pHel851aa (hatched rectangle) or with the defective helper plasmid pHel316aa (white rectangle). Donors are shown in the ExHy mode below the rectangles. Average colony numbers for three measurements are shown. Vertical lines indicate standard errors of the mean.

A transposition frequency for each of five types of donor plasmids was measured, combining the donor plasmids with a complete helper plasmid or a defective helper plasmid (FIG. 18). Both in human and in mouse cells, the size of an element was negatively correlated with transposition frequency. The ratio of transposition frequency of the longest element (pDon263McsNeoE20) and transposition frequency of the shortest element (pDon263McsNeoH20), when incorporated with a complete helper, was 0.21 in a human cell and 0.28 in a mouse cell. In a human cell, a transposition frequency of a donor plasmid with a complete helper plasmid, in the case of using the longest element, was 8 times higher than a transposition frequency of a donor plasmid with a defective helper; in a mouse cell, it was 10 times higher.

(6) Demonstration of Transposition

Next, a trial was performed to demonstrate that incorporation of Tol1 element into a chromosome was due to a transfer reaction. First, two colonies of mouse cells obtained in the trial with the longest element (pDon263McsNeoE20) were used to establish cell lines. These cell lines (N1 and N2, in which "N" means a neomycin-resistant transformant) were respectively amplified and their genomic DNA was extracted. The extracted DNA was used as a PCR template and an end region of Tol1 and a chromosome region adjacent to the end region were amplified. The amplification was carried out by inverse PCR. A nucleotide sequence of the PCR product was then examined. It was found that 8 bp of a target site duplication was generated in both cell lines (FIG. 19). Generation of target site duplication means that a reaction incorporating a donor DNA into a chromosome was a transfer reaction. A BLAST search of a mouse database, indicated that the nucleotide sequence was incorporated into chromosome 15 and chromosome 5.

Figure 20:
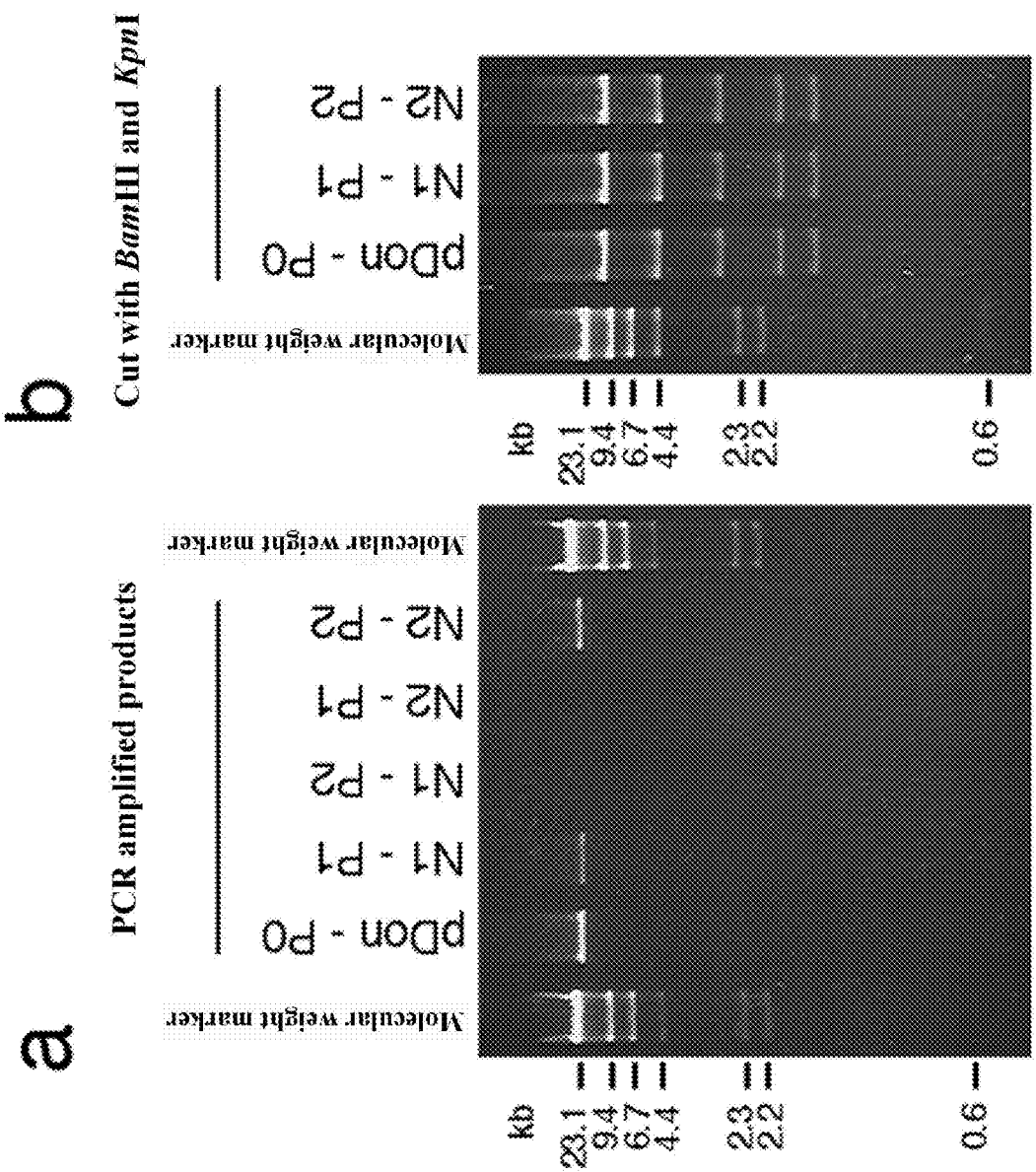
FIG. 20 shows an analysis of incorporated Tol1 element.

Thus, incorporation into chromosomes by transposition was confirmed. However, it was unclear whether the whole Tol1 element, including an internal DNA fragment, was incorporated in chromosomes without generating partial deletions or disruptions. Therefore, a primer recognizing a Tol1 end region and a chromosome region adjacent to the end region was prepared and PCR was performed. The cell line from which genomic DNA was extracted was diploid; thus, insertion of Tol1 likely occurred in only one of the two homologous chromosomes. The incorporated Tol1 element was amplified using a primer designed, as described above. A corresponding site in the other chromosome was never amplified. This is because the primer included sequence recognizing part of the nucleotide sequence of Tol1 element in the 3'-end, a sequence that was absent from the corresponding site in the other chromosome. PCR amplification was only observed for the correct combination of a cell line and a primer (FIG. 20). The length of an amplified product was as expected (i.e., 22.1 kb) and a restriction digest map, obtained by cutting the amplified product with restriction enzymes, was also as expected (FIG. 20). These results demonstrated that the whole region of Tol1 element, 22.1 kb, was incorporated into a chromosome by a transfer reaction without generating deletions or disruptions.

3. Consideration (1) Variations in the Length of Tol1 Element

In this study, variations in the length of Tol1 element was examined and it was found that copies about 18 kb and about 20 kb long exist in a medaka fish genome. This result indirectly supported the inventors' reasonings that Tol1 element transfers even if the length thereof exceeds 15 kb.

Two genomic library screens and three PCRs on each clone were performed. Other considered methods include (1) analysis of a nucleotide sequence database of medaka fish and (2) PCR of genomic DNA. Although the nucleotide sequence database of medaka fish has continuously improved, at the time of invention, precise incorporation of a long scattered repeat sequence, such as a transposable element, could not be obtained from the database. Continuous sequences such as a contig or scaffold sequence are assembled by a computer, and these sequences are often broken at the inside of long repeat sequences. Actually, autonomous Tol1 element of 4.4 kb, which was previously identified by the present inventors (Cited document 10), has not yet appeared in the database as a train of one sequence (version 46 published in August 2007).

PCR directly using genomic DNA could not be used. This is because the frequency of short copies, e.g., 1 to 2 kb, is far greater than the frequency of long copies in Tol1; importantly, short copies are predominantly amplified in PCR. Accordingly, much cloning and subsequent PCR analyses on each clone was the only feasible means for conducting this study.

(2) Removal of Unnecessary Internal Region

The present inventors constructed a basic Tol1 vector made with 157 bp of the left arm and with 106 bp of the right arm. The vector transferred at a high efficiency and equivalent to that of the original element (1855 bp). Thus, the present inventors succeeded in removing a 1592 bp internal region. This modification produced an increased space for loading a DNA fragment. Further, it is possible that the internal 1592 bp region includes signals that influence the loaded DNA or the host cell; thus, removing this region may obliterate such influence.

It is likely that the arms could be cut shorter. However, such an analysis was not performed since it is unlikely that a significant increase in loading capacity could be obtained for shorter arms, given that when arms are only 26 bp long, the transposition frequency is extremely decreased (FIG. 16) (the increased content becomes (157−26)+(106−26)=211 bp even at maximum). Also, if arms with certain lengths are preserved, the arms can be used in an analysis of an element incorporated by transposition. In many cases, an initial step in such an analysis is cloning an adjacent chromosome region. The main technique thereof is inverse PCR and it is necessary to use a part of the arms as primer regions in the inverse PCR. Further, two or more rounds of nested PCRs may be necessary, each round requiring a different part of the arms as primers targets. Consequently, the present inventors preserved a portion that can be used for a PCR primer. The arm lengths of the basic vector (157 bp and 106 bp) were determined based on such consideration.

(3) Influence of Element Size on Transposition Frequency

Transposition frequencies were measured when a complete helper plasmid and a defective helper plasmid was used. Formation of colonies was observed also when the defective helper plasmid was used. However, as shown in Example 1, when a defective helper plasmid was used, Tol1 element of a colony did not accompany target site duplication; therefore, the colony was generated by random insertion, not by transposition. This explanation is supported by the fact that the colony numbers using defective helper plasmids were approximately the same among five types of donors. Further, this result also indicates that the inventors had negated any influence of a plasmid size on a DNA incorporation efficiency when using lipofection.

It was revealed from an analysis of transformant cells that the whole region of Tol1 element was incorporated into a chromosome by a transposition reaction. The incorporation frequency was significantly high even for the longest Tol1 element (pDon263McsNeoE20), when compared to random incorporation frequency. The length of Tol1 element of this donor plasmid was 22.1 kb of which 0.3 kb was an arm of Tol1. Accordingly, the basic vector (pDon263Mcs) can deliver to a chromosome a DNA fragment with a length up to 21.8 kb. It was also an important finding that the delivered DNA fragment did not have internal deletions or disruptions.

(4) Comparison with Other Transposable Elements

It is known that Sleeping Beauty element loses transposition efficiency when the whole length exceeds 9.1 kb (Cited document 6). It has been found that piggyBac element functions as a gene introduction vector even when the whole length is 14.3 kb (Cited document 3). In the case of Tol2 element, the maximum length reported so far is 10.2 kb (Cited document 1). For the piggyBac element and Tol2 element, it is possible that transposable activities are retained even for lengths longer than previously reported. Currently, 22.1 kb, as now shown by the present inventors with Tol1, is the largest mammalian DNA transposable element. In addition, the basic vector prepared by the present inventors has an arm of Tol1 as short as 0.3 kb. From the above description, it is clear that Tol1 is a useful gene introduction vector that allows long DNAs to be incorporated in mammalian chromosomes.

CITED DOCUMENTS

1. Balciunas D., Wangensteen K. J., Wilber A., Bell J., Geurts A., Sivasubbu S., Wang X., Hackett P. B., Largaespada D. A., McIvor R. S., Ekker S. C. (2006) Harnessing a high cargo-capacity transposon for genetic applications in vertebrates. PLoS Genet. 2: e169
2. Calvi B. R., Hong T. J., Findley S. D., Gelbart W. M. (1991) Evidence for a common evolutionary origin of inverted repeat transposons in *Drosophila* and plants: hobo, Activator, and Tam3. Cell 66:465-471
3. Ding S., Wu X., L1 G., Han M., Zhuang Y., Xu T. (2005) Efficient transposition of the piggyBac (PB) transposon in mammalian cells and mice. Cell 122: 473-483
4. Fraser M. J., Ciszczon T., Elick T., Bauser C. (1996) Precise excision of TTAA-specific lepidopteran transposons piggyBac (IFP2) and tagalong (TFP3) from the baculovirus genome in cell lines from two species of Lepidoptera. Insect Mol Biol 5: 141-151
5. Ivics Z., Hackett P. B., Plasterk R. H., Izsvak Z. (1997) Molecular reconstruction of Sleeping Beauty, a Tc1-like transposon from fish, and its transposition in human cells. Cell 91: 501-510
6. Karsi A., Moav B., Hackett P., Liu Z. (2001) Effects of insert size on transposition efficiency of the Sleeping Beauty transposon in mouse cells. Mar Biotechnol 3: 241-245.
7. Koga A., Hori H. (1999) Homogeneity in the structure of the medaka fish transposable element Tol2. Genet Res 73: 7-14
8. Koga A., Iida A., Hori H., Shimada A., Shima A. (2006) Vertebrate DNA transposon as a natural mutator: the medaka fish Tol2 element contributes to genetic variation without recognizable traces. Mol Biol Evol 23: 1414-1419.
9. Koga A., Inagaki H., Bessho Y., Hori H. (1995) Insertion of a novel transposable element in the tyrosinase gene is responsible for an albino mutation in the medaka fish, *Oryzias latipes*. Mol Gen Genet 249: 400-405
10. Koga A., Shimada A., Kuroki T., Hori H., Kusumi J., Kyono-Hamaguchi Y., Hamaguchi S. (2007) The Tol1 transposable element of the medaka fish moves in human and mouse cells. J Hum Genet. 52: 628-635
11. Koga A., Shimada A., Shima A., Sakaizumi M., Tachida H., Hori H. (2000) Evidence for recent invasion of the medaka fish genome by the Tol2 transposable element. Genetics 55: 273-281
12. Koga A., Suzuki M., Inagaki H., Bessho Y., Hori H. (1996) Transposable element in fish. Nature 383: 30
13. Koga A., Suzuki M., Maruyama Y., Tsutsumi M., Hori H. (1999) Amino acid sequence of a putative transposase protein of the medaka fish transposable element Tol2 deduced from mRNA nucleotide sequences. FEBS Lett 461: 295-298
14. Miskey C., Izsvak Z., Plasterk R. H., Ivics Z. (2003) The Frog Prince: a reconstructed transposon from *Rana pipiens* with high transpositional activity in vertebrate cells. Nucleic Acids Res 31: 6873-6881
15. O'Hare K., Rubin G. M. (1983) Structures of P transposable elements and their sites of insertion and excision in the *Drosophila melanogaster* genome. Cell 34: 25-35
16. Rubin E., Lithwick G., Levy A. A. (2001). Structure and evolution of the hAT transposon superfamily. Genetics 158: 949-957
17. Zagoraiou L., Drabek D., Alexaki S., Guy J. A., Klinakis A. G., Langeveld A., Skavdis G., Mamalaki C., Grosveld F., Savakis C. (2001) In vivo transposition of Minos, a *Drosophila* mobile element, in mammalian tissues. Proc Natl Acad Sci USA 98: 11474-11478

Example 3

It was shown in Example 2 that Tol1 is able to carry a long DNA fragment in a chromosome and is an excellent genetic tool. Specifically, it was revealed that Tol1 effectively transposes even if the whole length is as long as 22.1 kb and that Tol1 functions as a vector when the total length of its left and right arms is only 263 kb. Further, it has been shown that Tol1 transposes in human cells and in mouse cells in addition to medaka fish (Example 1; Cited document 15). Therefore, is expected that Tol1 has transposable activity in a wide range of vertebrates.

A DNA transposable element transfers via "cut and paste." "Cut" indicates a process of excising an element from a DNA molecule, such as a chromosome, on which the element is currently carried. "Paste" means incorporation of the excised element into the same or another DNA molecule. Herein, detection of a "cut" is easy because sufficient information can be obtained by a PCR analysis focusing on a specific element. However, demonstration of incorporation, i.e., "paste" is not as easy since the element's incorporation location is unknown beforehand; thus, a marker gene and a complicated detection system are required.

An object of this study is to examine whether excision of Tol1 element occurs in *X. laevis*. For this object, an indicator plasmid (in which Tol1 element is embedded) and a helper plasmid (for supplying a transfer enzyme in a cell) were prepared. These plasmids were injected into a flog embryo at an early developmental stage and recovered from the embryo after cell division. Subsequently, the indicator plasmid was analyzed by PCR, cloned, and sequenced. The results showed excision of Tol1 element from the plasmid. Various sequences, known as traces, were also observed at a breaking point. The above results revealed that Tol1 element also shows transposase activity in this model animal, which suggested that Tol1 has excellent versatility as a tool for genomic manipulation.

The sequence of the trace was similar to those used in fish and mammals. However, a tendency that a specific nucleotide would appear at a breaking point was observed. Accordingly, it is possible that a DNA repair mechanisms specific to this frog (or to amphibians, in general) exists, and that the above-mentioned tendency reflects the repair mechanisms.

1. Materials and Methods (1) Plasmids

Two types of plasmids were used: an indicator plasmid and a helper plasmid. The former includes a nonautonomous Tol1 element and the latter includes a transposase enzyme gene controlled by a CMV promoter. In cells, the helper plasmid supplies a tranposase enzyme, which catalyzes transposition of the Tol1 element present in the indicator plasmid.

In addition to a complete helper plasmid, a defective helper plasmid was also prepared to control for functions of the tranposase enzyme. The defective helper plasmid was obtained by replacing two codons (encoding amino acids) in the middle of the tranposase enzyme with stop codons.

Figure 21:
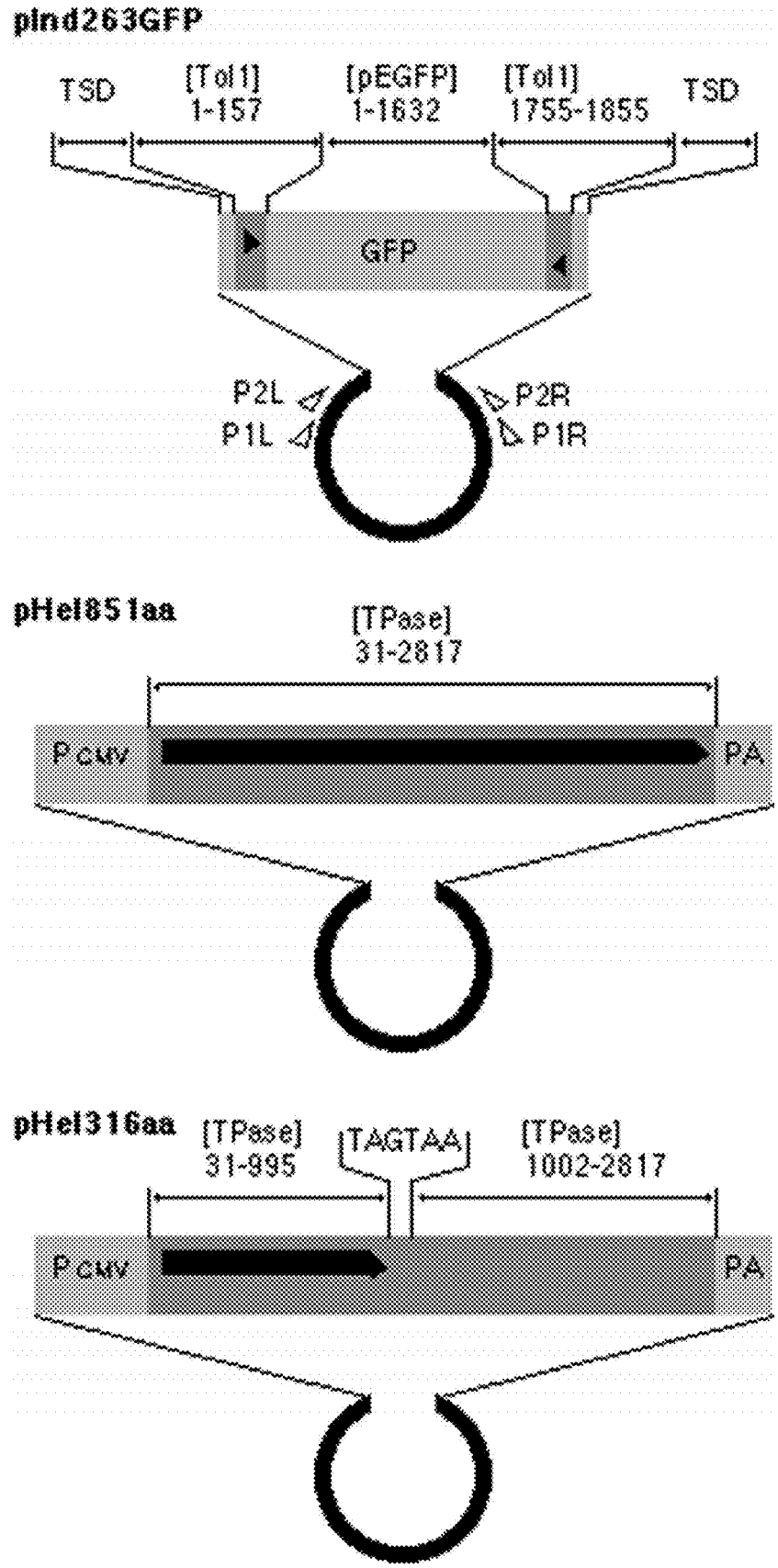
FIG. 21 shows structures of an indicator plasmid and a helper plasmid. plnd263GFP is an indicator plasmid that includes both ends of the first discovered Tol1 element (Tol1-tyr, 1855 bp, SEQ ID NO: 10) and a GFP gene inserted therebetween; plnd263GFP is formed by inserting the above into pUC19. pHel851aa is a complete helper plasmid and was prepared by inserting a sequence encoding a Tol1 transfer enzyme (851 amino acids, SEQ ID NO: 2) between a CMV promoter of a pCI plasmid (Promega, Madison, Wis., USA) and poly-A additional signal. pHel316aa is a defective helper plasmid that was prepared by introducing a mutation by PCR. Bases 996 to 1001 is ATGAAA, which corresponds to amino acids, methionine and lysine, in the transfer enzyme. Using PCR, the ATGAAA was mutated to TAGTAA so that two termination codons appeared near the middle of the transfer enzyme's ORF. In the drawing, abbreviations and nucleotide positions are included. The abbreviations are as follows: [Tol1] D84375 (Tol1-tyr element), [TPase] AB264112 (transfer enzyme gene), [pEGFP] U55763 (plasmid pEGFP-C1; Clontech Laboratories, Mountain View, Calif., USA). TSD shows target site duplication of the sequence CCTTTAGC (SEQ ID NO: 13). $P_{CMV}$ represents a CMV promoter and PA represents a poly-A additional signal. The heavy line having a triangular right edge is an ORF contained in the complete and defective helper plasmids. The black triangles indicate end inverted repeat sequences present in the Tol1-tyr element. The open white triangles indicate positions and directions of PCR primers used to detect excision.

Indicator plasmid plnd263GFP contains a 263 kb arm of Tol1 element with and a GFP gene. The complete helper plasmid pHel851aa encodes a tranposase enzyme of 851 amino acids. The defective helper plasmid pHel316aa encodes a inactive protein having only 316 amino acids. Their structures are shown in FIG. 21. The GFP gene in plnd263GFP comprises a CMV promoter, a coding sequence of eGFP, and a poly-A additional signal. This GFP gene serves as a marker gene to confirm that DNA injected into an embryo cell is incorporated into a chromosome.

(2) Injection of Frog Embryo and DNA 600 units and 300 units of chorionic gonadotropin (Aska Pharmaceutical, Tokyo, Japan) were injected into a female frog and a male frog, respectively. The frogs were naturally bred to obtain a fertilized egg. After removing the fertilized egg's jelly layer in 3% cysteine (pH 7.9) and washing the egg with 0.1× Steinberg's solution (Cited document 12), the egg was transferred to 3% Ficoll, 0.1× Steinberg's solution. When the fertilized egg had become a four cell embryo, it was injected with 5 nl of plasmid DNA dissolved in a volume of 88 mM NaCl, 15 mM Tris-HCl (pH 8.0) such that the concentration of the indicator plasmid would be 5 µg/ml and the concentration of the helper plasmid would be 50 µg/ml. After DNA injection, the embryo was cultured in 0.1× Steinberg's solution at 20° C. The ratio of the indicator plasmid to the helper plasmid was 1:10; this ratio is similar to that used in Example 1, which showed that the highest transposition frequency in mammalian cultured cells when the ratio was 1:9.

(3) PCR Analysis

DNA was recovered from an embryo having GFP luminescence when the embryos had reached the tailbud stage. To recover DNA, the embryo was placed in and crushed in a digestion solution 100 µl of [10 mM Tris-HCl, 10 mM EDTA (pH 8.0), 200 µg/ml proteinase K], and digested at 50° C. for 12 hours or more. 2 µl of the digestion product was used as a template, and PCR was performed to detect excision. The polymerase used was KOD Plus polymerase (Toyobo, Osaka, Japan). Primers were P1L (208th to 237th bases in GenBank file L09137) and P1R (770th to 741st bases), which correspond to parts of plasmid pUC19. A position where Tol1 element was incorporated was from the 400th to 441st bases, which was interposed between the primers. Concentrations of dNTPs, MgSO$_4$ and the primers were respectively set to 0.2 mM, 2 mM, and 0.5 µM. Conditions of PCR are described in the corresponding section.

(4) Cloning and Sequencing

The PCR product was diluted 1/500 in water, and a second PCR was performed using 1 µl of the diluted PCR product as template. The primers used were P2L (338th to 367th bases of L01937) and P2R (650th to 621st bases). This nested-type PCR facilitates cloning of a first PCR product. The second PCR product was cloned into an EcoRV site of pBluescript II KS(−) (Stratagene, La Jolla, Calif., USA), and was later sequenced using a T3 primer and a T7 primer; for this, an ABI PRISM® 310 Genetic Analyzer (Applied Biosystems, Foster City, Calif., USA) was used.

2. Experimental Results (1) Injection of Plasmid into Embryo and Recovery Thereof This experiment consists of two sets of A and B. In A, an indicator plasmid (plnd263GFP) and a complete helper plasmid (pHel851aa) were injected into an embryo of *X. laevis* from the two-cell to four-cell stages. Set B is a control experiment for determining activity of a transposase enzyme and a defective helper plasmid (pHel316aa), instead of a complete helper plasmid. In set B, an indicator plasmid was also injected. In set A, DNA was injected into 154 embryos, and in set B, DNA was injected into 168 embryos; 112 embryos and 136 embryos, respectively, survived to the tailbud stage. No obvious difference in survival rates was observed between sets A and B ($\chi^2$=3.07, DF=1, P>0.1).

Injected DNA molecules must migrate to a nucleus for excision to occur. This is because transcription occurs in a nucleus and for a transposase gene, which is carried on a helper plasmid, to be transcribed, the transposase must be in the nucleus. To verify this premise, a GFP gene, which is carried on a indicator plasmid was used. When GFP is expressed, it means that a the indicator plasmid had migrated into a nucleus. 57% (64/112) of the embryos of set A expressed GFP and 65% (88/136) of the embryos of set B expressed GFP. There was no apparent difference between these frequencies ($\chi^2$=1.48, DF=1, P>0.4). There was also no obvious difference in special patterns of GFP expression when the embryos were observed under a microscope. 12 embryos having stronger GFP expression (A1 to A12) were selected from the embryos of set A; 12 embryos (B1 to B12) were also selected from the embryos of set B. Plasmid DNA was individually recovered from these 24 embryos.

(2) PCR Analysis of Recovered Plasmids

Two PCR protocols were performed on the recovered DNA. The primers used were P1L and P1R (placed in a position where Tol1 element was interposed between plnd263GFP).

Figure 22:
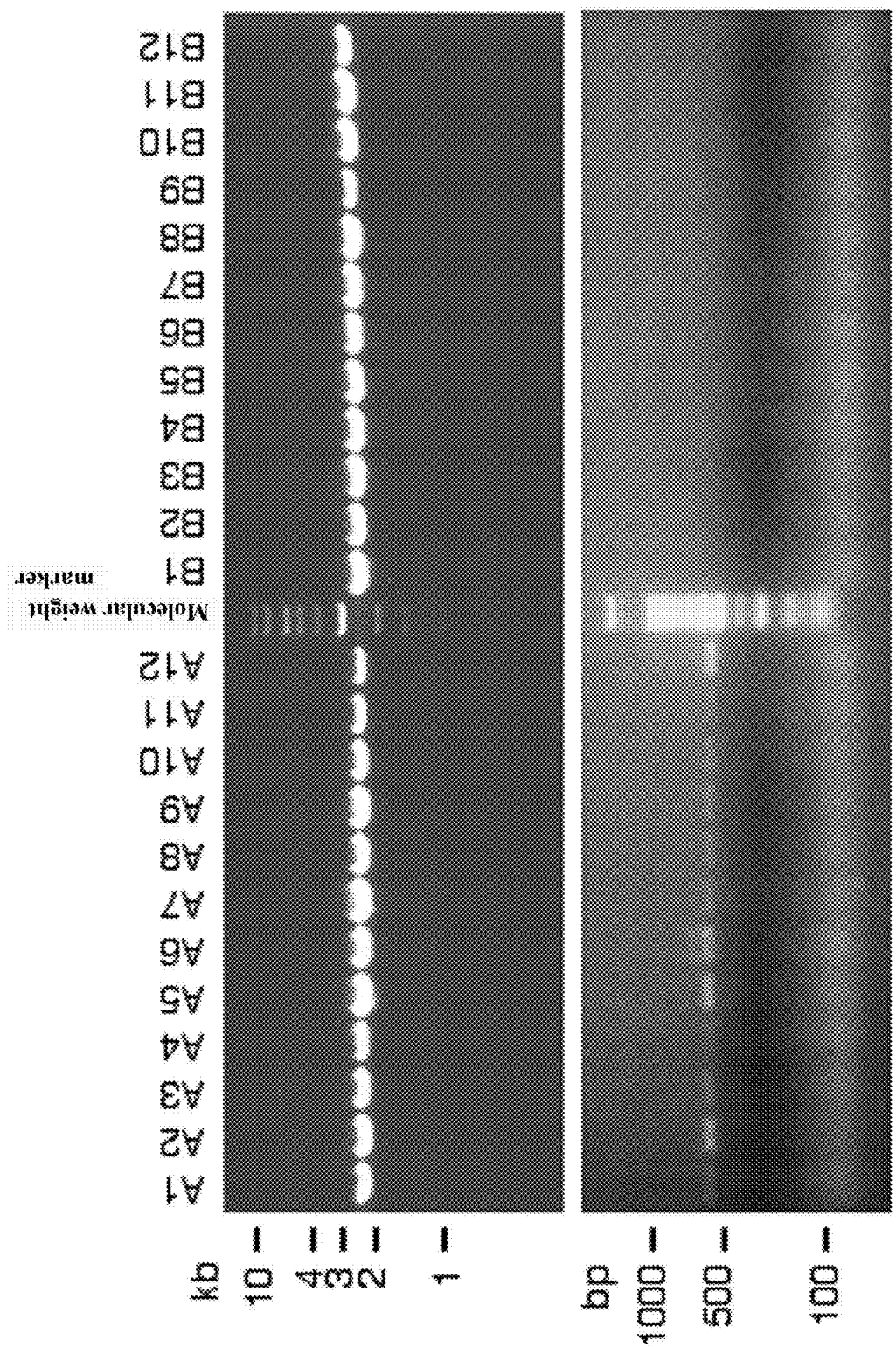
FIG. 22 shows detection by PCR of excision in an *X. laevis* embryo. A1 to A12 are 12 embryos from set A. B1 to B12 are 12 embryos from set B. The upper image shows electrophoresis bands of PCR products for PCR that amplified the whole region of Tol1 element. PCR conditions were as follows: [94° C., 120 seconds], 33×[94° C., 20 seconds; 64° C., 20 seconds; 68° C., 150 seconds], and [68° C., 60 seconds]. PCR products were electrophoresed in a 1.0% agarose gel with 5 μl of each 20 μl PCR product was loaded per lane. 2.4 kb bands were observed in all samples of A and B. The lower image shows results of PCRs that efficiently amplified a product of excision. PCR conditions were the same as in the upper image except the elongation step was shortened to 40 seconds. In addition, the agarose concentration in the electrophoresis was 2.0%. An approximately 535 bp band was observed in samples A1 to A12. No such band was observed in samples B1 to B12.

The first PCR protocol was to confirm that a indicator plasmid was recovered. The distance between the two primers on plnd263GFP was 2.4 kb, and a product having this length was confirmed in all samples (FIG. 22, upper column). Even though there were different amounts of the products among samples, there was no clear difference in product amounts, overall, between set A and set B. These results confirmed that the indicator plasmid was recovered. If Tol1 element excision from plnd263GFP occurred precisely, a 535 bp PCR product should have been amplified; however, no product of this size was found in any sample.

The second PCR protocol had a shortened elongation step (40 seconds rather than 150 seconds as used in the first PCR protocol) (FIG. 22, lower column). A 40 second elongation step is not sufficient for amplifying the whole region of Tol1 element, and thus, it was expected that a product resulting from excision could be PCR amplified. A PCR product having a size close to 535 bp was observed in all samples of set A (A1 to A12). In contrast, in no sample from set B, was such a PCR product observed. Thus, dropout of Tol1 element from plnd263GFP occurred in embryos of set A but not in embryos of B.

(3) Analysis of PCR Products' Nucleotide Sequences

Figure 23:
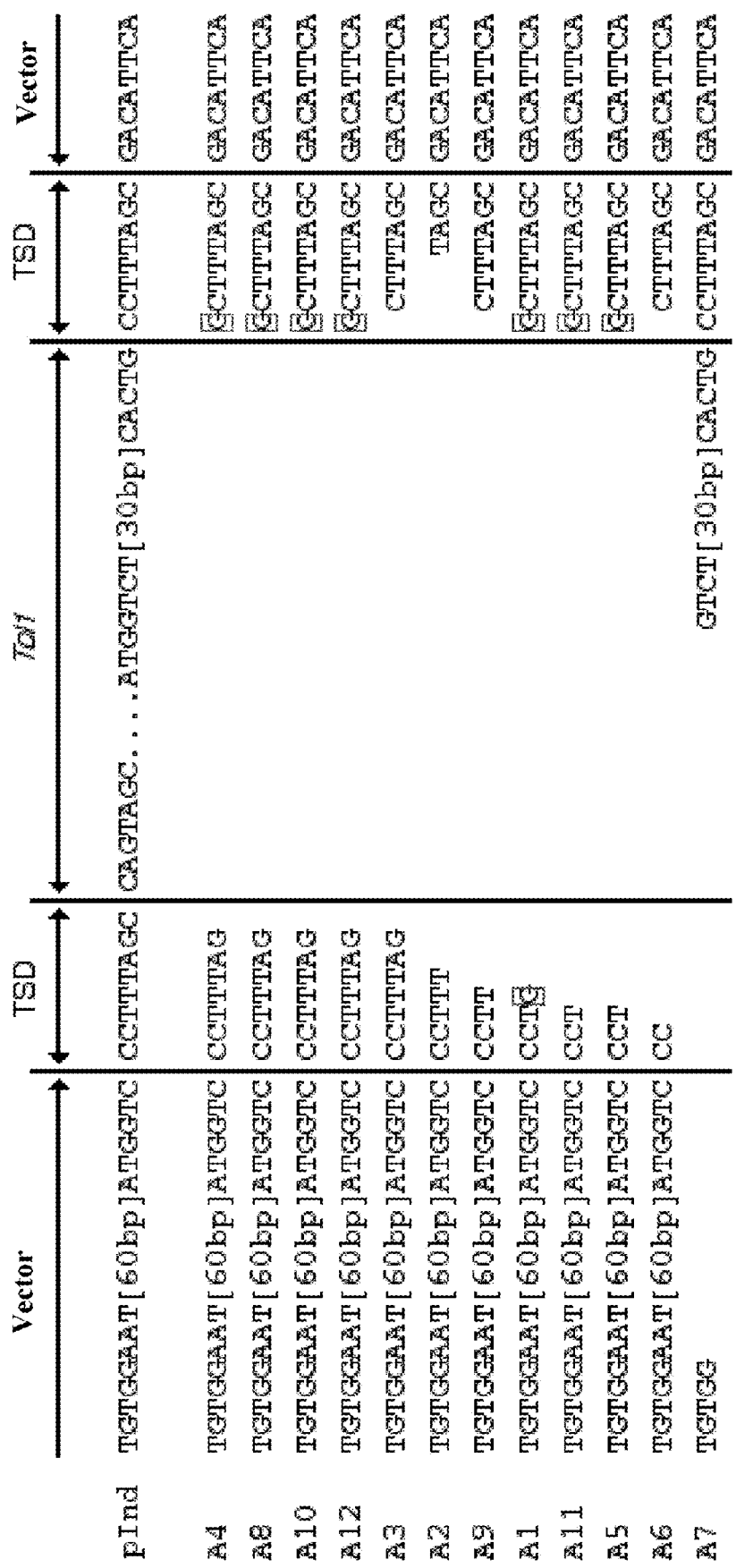
FIG. 23 shows nucleotide sequences around a breaking point of excision (SEQ ID NOS 78-81, 80-81, 80-81, 80-81, 80, 82-85, 82, 86, 81, 87, 81, 87, 81 and 88-90, respectively, in order of appearance). "plnd" in the uppermost row is the sequence of plnd263GFP which is shown for reference. "TSD" indicates target site duplication. The full TSD is present in the plnd263GFP plasmid. Nucleotides enclosed within boxes are not present in plnd263GFP. Bracketed text, for example "[60 bp]", represent sequences that are too long to be included in the figure. The sequences of corresponding portions are as follows: [60 bp], the 504th to 445th bases of L09137 (pUC19), and [30 bp], the 1821st to 1850th bases of D84375 (Tol-tyr).

Nucleotide sequences of the PCR products obtained from 12 embryos of set A were analyzed to examine positions and shapes of break points generated in plnd263GFP. For this analysis, PCR products were again amplified by a nested-type PCR. The primers used were P2L and P2R. Subsequently, PCR products were cloned into plasmids. At this time, only one colony (clone) among the generated colonies was randomly selected for each embryo. Accordingly, the 12 samples in these experiments were all generated by separate excisions. FIG. 23 shows the aligned nucleotide sequences obtained from the 12 samples. In the 12 samples, all or most of the Tol1 element sequence disappeared. Thus, in frog cells, excision of Tol1 element occurred simultaneous with an indicator. Whole regions of Tol1 element were excised in 11 of the 12 samples (A1 to A6 and A8 to A 12) and with only 1 to 7 nucleotides corresponding to a part of TSD remaining. 39 nucleotides in the right end of Tol1 element remained in sample A7, and 77 nucleotides in a chromosome region adjacent to the left side of Tol1 disappeared. A part corresponding to one TSD was included in these 77 nucleotides. It was further found that new guanosine (G) residues were introduced in 7 out of 12 samples, either by insertion of a G or by replacement of another nucleotide with a G.

3. Discussion

In this study, an indicator plasmid (plnd256GFP) was injected into an embryo from the two-cell to four-cell stages along with a complete helper plasmid (pHel851aa), for set A, or a defective helper plasmid (pHel316aa), for set B. There was no apparent difference in expression frequencies and distribution patterns of GFP in tailbud stages between set A and set B. Therefore, there does not appear to be a clear difference in incorporation efficiencies of DNA into nuclei between set A and set B. Additionally, amounts of indicators recovered from embryos were equal between set A and set B. However, there was a clear difference in PCR products between samples from set A and set B, indicating excision occurred in set A but not in set B. Accordingly, this clear difference is due to a difference in the nucleotide sequences between the complete helper plasmid and the defective helper plasmid. This difference being only an internal 6-nucleotide region corresponding to codons for the 317th and 318th amino acids in pHel851aa, which are replaced with two stop codons in pHel316aa. The above results indicate that dropout of the Tol1 portion from the indicator is due to activity of an enzyme encoded by pHel851aa, whereas a protein encoded by pHel316aa does not have such activity.

It can be concluded from the above results that Tol1 element causes excision in *X. laevis* cells. This conclusion is supported by evidence that various traces (i.e., addition or omission of nucleotides of the transferred fragment) accompanied dropout of Tol1 fu. This is because such traces have been observed in many other DNA transposable elements, with examples including hobo of *Drosophila* (Cited document 1), Activator of corn (Cited document 17), Tam3 of snapdragon (Cited document 4), mariner of *Drosophila* (Cited document 2), and Tc1 of nematode (Cited document 13).

It is interesting that G residues (cytidine (C) residues in complementary strands) were introduced in 7 samples. Since an analysis of nucleotide sequences was carried out in both strands, it is unlikely that this phenomenon is an artifact due to an experimental method. Since the phenomenon occurred in separate excisions of no less than 7 samples, it is possible that DNA repair mechanisms specific to this specific frog (or to amphibians, in general) exists and that the phenomenon reflect these mechanisms. Although the present inventors analyzed PCR products in 20 or more medaka fish and 20 or more mammalian cultured cells so far, this has not before been observed.

Excision is only a part of a transfer reaction of a DNA transposable element. However, hAT family elements transfer in an unreplication method, that is, a method of inserting an excised fragment into another site (Cited document 10). Understanding the transfer reaction, on the whole, in *X. laevis* cells will surely be realized.

Among the 12 excisions examined, there was no sample in which a nucleotide sequence accurately returned to its original state. However, this does not signify that the dropped elements are inaccurately incorporated into chromosomes. It is a phenomenon frequently observed in a DNA transposable element that, although the element is precisely cut out at an end and incorporated into a new place, there is an addition or omission of nucleotides upon transfer into a chromosome. The causes may be due to double-strand break repair (Cited document 13), nonhomologous recombination (Cited document 16), and the like. The present inventors recently cloned two Tol1 elements newly inserted in mouse chromosomes. In this example, the first to last nucleotides of the element were exactly cloned with 8 bp of TSD.

DNA transposable elements such as Sleeping Beauty and Tol2 have been used as tools for genomic manipulation in frogs (Cited documents 14 and 5). However, Tol1 has a characteristic which is superior to those elements, i.e., Tol1 can carry a long DNA fragment (see Example 2). Accordingly, Tol1 is not merely an additional genetic manipulation technique useful for frogs, but should be recognized as a useful tool for further experimentation and insights.

CITED DOCUMENTS

1. Atkinson, P. W., Warren, W. D. & O'Brochta, D. A. (1993). The hobo transposable element of *Drosophila* can be cross-mobilized in houseflies and excises like the Ac element of maize. Proceedings of the National Academy of Sciences of the USA 90, 9693-9697.

2. Bryan, G., Garza, D., Hartl, D. L. (1990). Insertion and excision of the transposable element mariner in *Drosophila*. Genetics 125, 103-114.

3. Cary, L. C., Goebel, M., Corsaro, B. G., Wang, H. G., Rosen, E., & Fraser, M. J. (1989). Transposon mutagenesis of baculoviruses: analysis of Trichoplusiani transposon IFP2 insertions within the FP-locus of nuclear polyhedrosis viruses. Virology 1 72, 156-169.

4. Coen, E. S., Carpenter, R. & Martin, C. (1986). Transposable elements generate novel spatial patterns of gene expression in *Antirrhinum majus*. Cell 47, 285-296.

5. Hamlet, M. R., Yergeau, D. A., Kuliyev, E., Takeda, M., Taira, M., Kawakami, K. & Mead, P. E. (2006). Tol2 transposon-mediated transgenesis in *Xenopus tropicalis*. Genesis 44, 438-445.

6. Ivics, Z., Hackett, P. B., Plasterk, R. H. & Izsvak, Z. (1997). Molecular reconstruction of Sleeping Beauty, a Tc1-like transposon from fish, and its transposition in human cells. Cell 91, 501-510.
7. Koga, A., Shimada, A., Kuroki, T., Hori, H., Kusumi, J., Kyono-Hamaguchi, Y. & Hamaguchi, S. (2007). The Tol1 transposable element of the medaka fish moves in human and mouse cells. Journal of Human Genetics 52, 628-635.
8. Koga, A., Suzuki, M., Inagaki, H., Bessho, Y. & Hori, H. (1996). Transposable element in fish. Nature 383, 30.
9. Koga, A., Inagaki, H., Bessho, Y. & Hori, H. (1995). Insertion of a novel transposable element in the tyrosinase gene is responsible for an albino mutation in the medaka fish, *Oryzias latipes*. Molecular and General Genetics 249, 400-405.
10. Kunze, R. (1996). The maize transposable element Activator (Ac) In: H. Saedlerand A. Gierl (ed.) Transposable Elements. Springer, Berlin. pp. 161-194.
11. Miskey, C., Izsvak, Z., Plasterk, R. H. & Ivics, Z. (2003). The Frog Prince: a reconstructed transposon from *Rana pipiens* with high transpositional activity in vertebrate cells. Nucleic Acids Research 31, 6873-6881.
12. Peng, H. B. (1991). Appendix A. Solutions and protocols. In: Kay, B. K. and Peng, H. B. (eds) *Xenopus laevis*: Practical Uses in Cell and Molecular biology. Academic Press, San Diego, pp. 661-662.
13. Plasterk, R. H. (1991). The origin of footprints of the Tc1 transposon of *Caenorhabditis elegans*. EMBO Journal 10, 1919-1925.
14. Sinzelle, L., Vallin, J., Coen, L., Chesneau, A., Du Pasquier, D., Pollet, N., Demeneix, B. & Mazabraud, A. (2006). Generation of trangenic *Xenopus laevis* using the Sleeping Beauty transposon system. Transgenic Research 15, 751-760.
15. Tsutsumi, M., Imai, S., Kyono-Hamaguchi, Y., Hamaguchi, S., Koga, A. & Hori, H. (2006). Color reversion of the albino medaka fish associated with spontaneous somatic excision of the Tol-1 transposable element from the tyrosinase gene. Pigment Cell Research 19, 243-247.
16. Weinert, B. T., Min, B. & R10, D. C. (2005). P element excision and repair by non-homologous end joining occurs in both G1 and G2 of the cell cycle. DNA Repair 4, 171-181.
17. Wessler, S. R., Baran, G., Varagona, M. & Dellaporta, S. L. (1986). Excision of Ds produces waxy proteins with a range of enzymatic activities. EMBO Journal 5, 2427-2432.
18. Wu, S. C., Meir, Y. J., Coates, C. J., Handler, A. M., Pelczar, P., Moisyadi, S. & Kaminski, J. M. (2006). piggyBac is a flexible and highly active transposon as compared to Sleeping Beauty, Tol2, and Mos1 in mammalian cells. Proceedings of the National Academy of Sciences of the USA 103, 15008-15013.

Example 4

A transfer reaction is one kind of DNA nonhomologous recombination which requires the combined actions of endonuclease, polymerase, ligase, etc. It is still unclear whether a single transfer enzyme performs each of these activities. That is, it is possible that the transfer enzyme partly relies on a host cell for certain required activities. A significant question, from both an evolutionary and biotechnological viewpoints, is whether a required factor is inherent to a host species or is present in a wide range of organisms. From an evolutionary viewpoint, this allows speculation regarding the frequency of transfer of transposable elements among species, also known as "horizontal transfer". Frequent horizontal transfer is known to be a significant contributor to evolution. From a biotechnological viewpoint, it is important to determine whether a new gene introduction system, etc., is applicable to a wide range of species. In any case, the fewer required host factors inherent to biological species, the wider range of species for which the new gene introduction system can be used. It is speculated from the above-described results (Examples 1 to 3) that Tol1 element has a transposable activity in vertebrates, in general.

Figure 24:
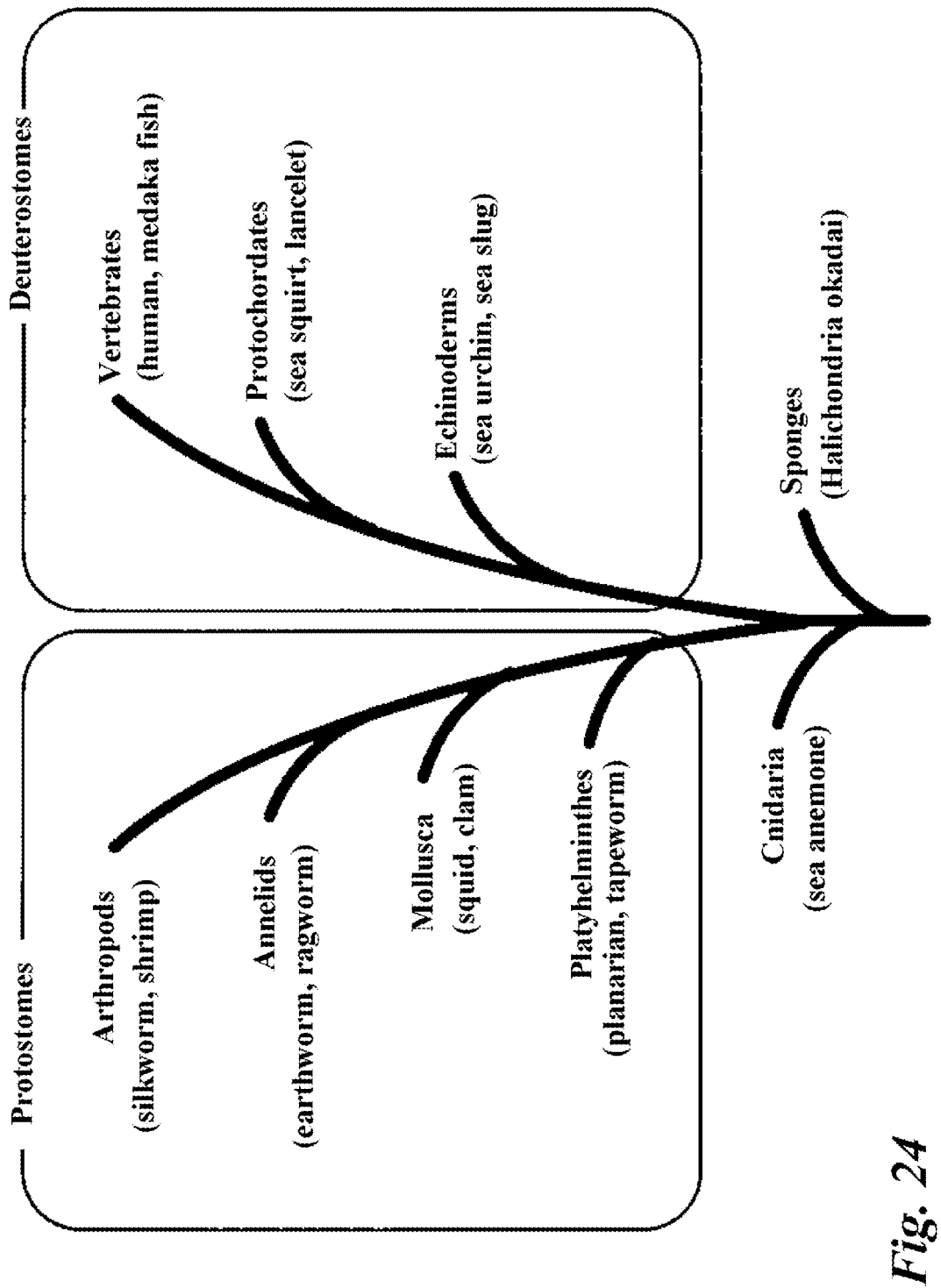
FIG. 24 illustrates a phylogenetic tree of the animal world. The drawing illustrates a standard phylogenetic tree based on phylum or subphylum.

As shown in FIG. 24, higher animals diverged into two large phyletic lines in an early stage of evolution. The two phyletic lines are protostomes and deuterostomes. In protostomes, a blastopore, which is generated during an embryo's early development, ultimately becomes the mouth; in deuterostomes the blastopore ultimate becomes the anus. Vertebrates are deuterostomes. Experiments were undertaken to determine whether Tol1 element transfers in protostomes; for this, the inventors used the silkworm, an insect.

Figure 25:
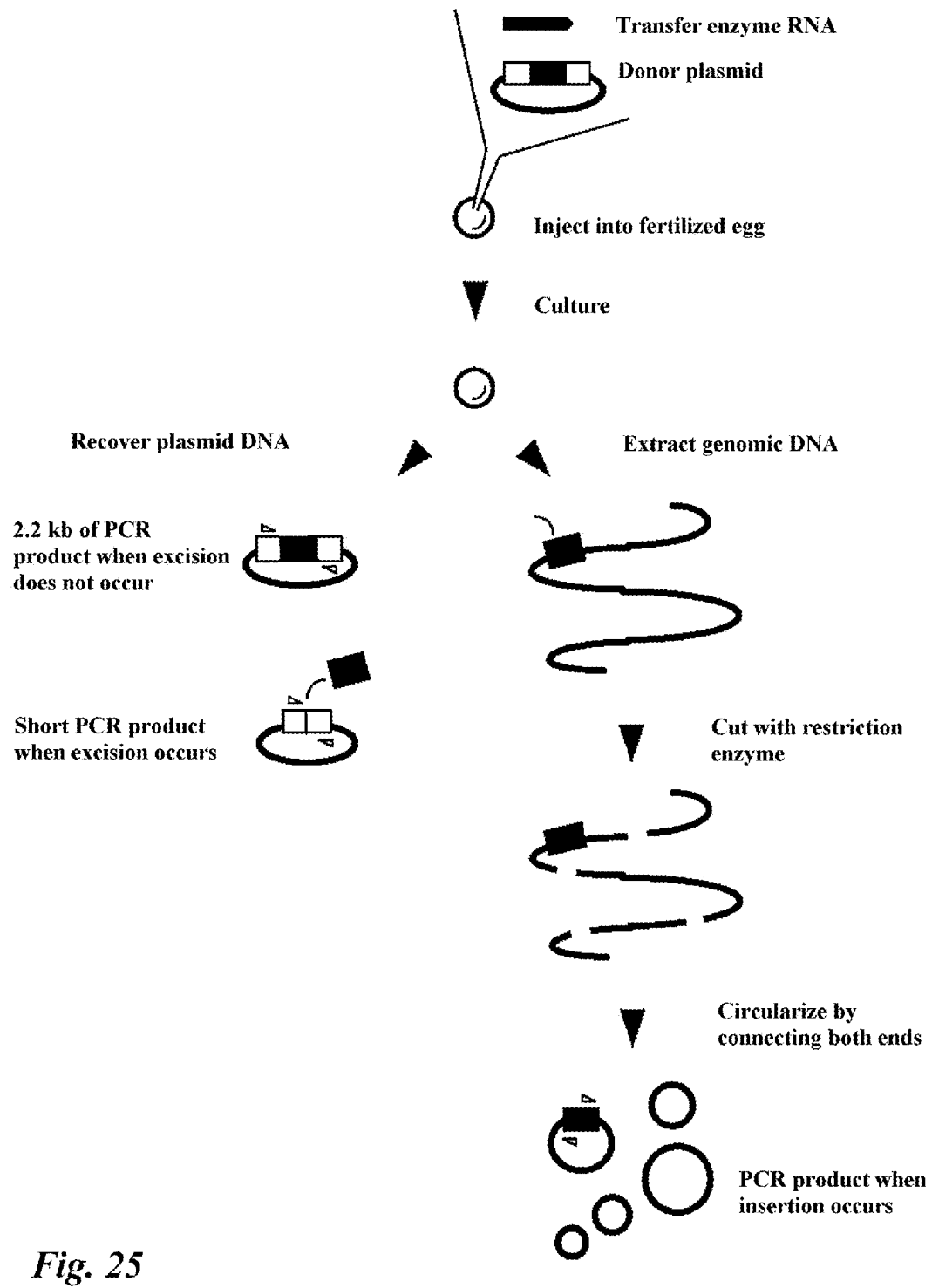
FIG. 25 illustrates the overall experiments performed herein, which diverge mid-course. The left branch illustrates detection of excision experiments and the right branch illustrates detection of insertion experiments.

1. Materials and Methods (1) Overview of Methods The overall procedure is shown in FIG. 25. DNA and RNA used and details of each step are described below.

(2) Transfer Enzyme RNA

Two plasmids (pTem851aa and pTem316aa), shown in FIG. 26, were constructed. RNAs (mRNA851aa and mRNA316aa) were synthesized using RiboMAX™ Large Scale RNA Production System (Promega Corp., Madison, Wis., USA) from pTem851aa and pTem316aa, respectively. mRNA851aa encodes the entire Tol1 transfer enzyme, i.e., 851 amino acids. mRNA316aa encodes up to the Tol1 transfer enzyme's 316th amino acid. mRNA316aa serves as a negative control. These two mRNAs have the same length. Their nucleotide sequences differ only in 6 bases in their middles, with pTem316aa having two stop codons rather than codons for Met and Lys.

(3) Donor Plasmids

Figure 27:
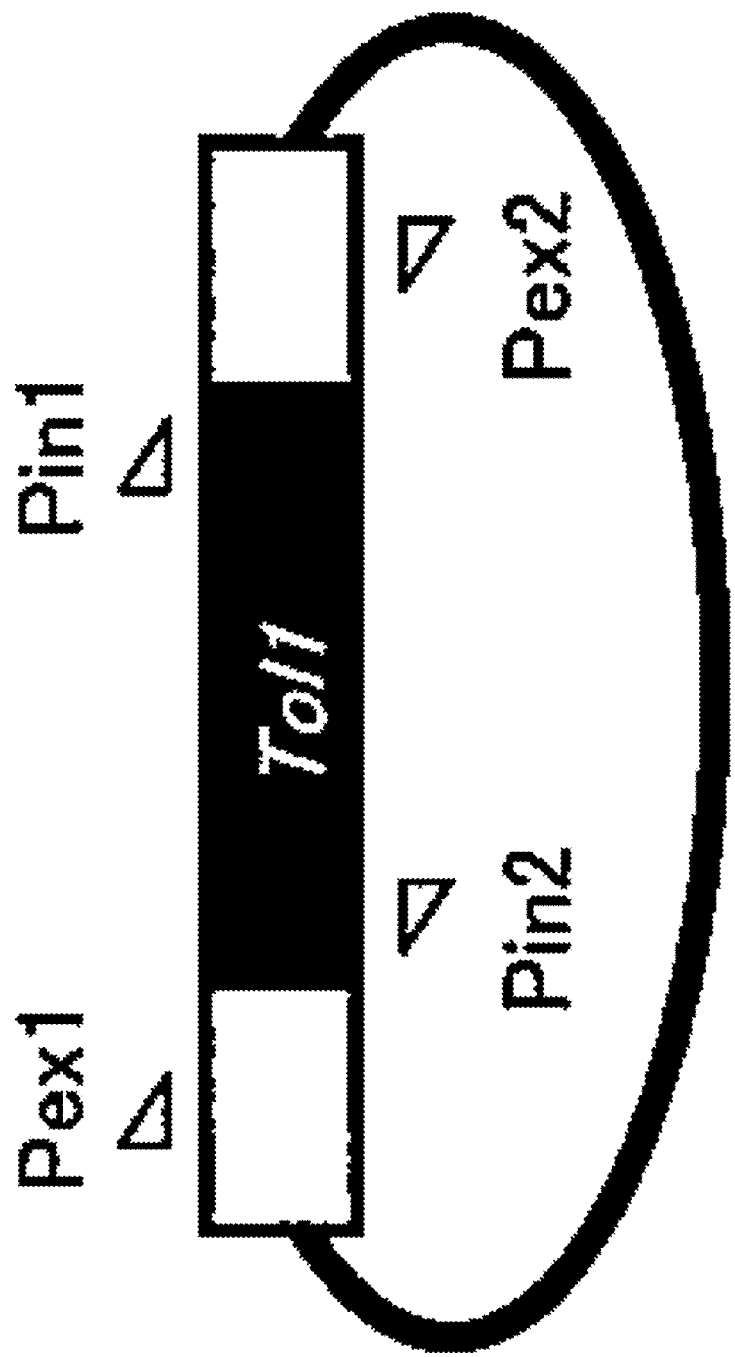
FIG. 27 shows a donor plasmid. White boxes identify a part of a tyrosinase gene (DDBJ/EMBL/GenBank Accession No. AB010101) of medaka fish. The black box identifies a Tol1 element (DDBJ/EMBL/GenBank Accession No. D84375). Triangles represent positions and directions of primers for detecting excision. nucleotide sequences are as follows: Pex1: 3,594 to 3,623 of AB010101; Pex2: 3,866 to 3,895 of AB010101; Pin1: 1,758 to 1,787 of D84375; and Pex2: 101 to 130 of D84375.

A donor plasmid as shown in FIG. 27 was constructed. This was obtained by cloning a part of a tyrosinase gene of an albino medaka fish. It contains 1855 bp of Tol1 element. It was expected that a transfer enzyme encoded by the native silkworm genome can cut out Tol1 element, and that the Tol1 element then transfers into a silkworm cell's chromosome. Here, a transfer enzyme gene is not included in the cloned 1855 bp (Cited document 5). Bacteria containing the donor plasmid were cultured in a liquid medium and plasmid DNA was extracted and purified using the QIAGEN® Plasmid Maxi Kit (QIAGEN GmbH, Hilden, Germany).

(4) Setting of Treatment Section

Three treatment conditions (A, B and C) were performed. In condition A, mRNA851aa and the donor plasmid were together injected into a fertilized silkworm egg; here, transposition should occur. In condition B, mRNA316aa and the donor plasmid were together injected into a fertilized silkworm egg; here, transposition should not occur since a transfer enzyme is incomplete. Condition C is a negative control and DNA or RNA was not injected into a fertilized egg.

(5) Injection into Silkworm

In conditions A and B, a donor plasmid and RNA were mixed so as to have final concentrations of 40 ng/µl and 160 ng/µl, and injected into fertilized eggs using a glass needle. Injection occurred within 40 minutes of the fertilized eggs being laid. Injection was performed on 250 fertilized eggs in condition A and 50 fertilized eggs in condition B. After injection, the fertilized eggs were stored in a plastic box. In condition C, 50 fertilized eggs (which were not injected with DNA and RNA) were stored in the same plastic box. The plastic box was kept warm, at 25° C., to promote development.

(6) Recovery of Plasmid DNA

After 5 to 6 hours of warming, 75, 25, and 25 embryos, respectively, were collected from conditions A, B and C. Groups of 25 embryos were placed into separate centrifuge tubes. The 75 embryos of condition A were divided into three sets of 25, which were named A1, A2, and A3. The remaining embryos of condition A continued to be kept warm at 25° C. Using the Hirt method (Cited document 3), DNA was extracted from embryos of each group. Cyclic DNA, e.g., plasmids, can be efficiently extracted by this method.

(7) Detection of Excision

PCR revealed whether Tol1 element was excised from recovered donor plasmids. The distance between primers Pex1 and Pex2 on the donor plasmid was 2.2 kb. If excision of Tol1 element occurred while the donor plasmid was present in a silkworm cell, the distance between Pex1 and Pex2 would be shortened. Therefore, a PCR product shorter than 2.2 kb indicates that excision had occurred. If only the Tol1 element part was precisely drawn out, the size of the PCR product would be 0.3 kb since Tol1 element is 1.9 kb long.

(8) Extraction of Genomic DNA

After 96 to 97 hours of warming at 25° C., 100 embryos of condition A were collected. Then, genomic DNA was extracted using standard methods: digestion with SDS and Proteinase K and DNA purification with salt and ethanol precipitation (Cited document 7). The obtained DNA was used for detection of insertion. The above-mentioned DNA extraction was performed after detection of excision because it was expected that the copy number a donor plasmid decrease over time as an embryo's cells duplicate. The donor plasmid has a region corresponding to a PCR primer used in insertion detection. Therefore, a PCR product independent from the insert would be generated. Accordingly, as the copy number of a donor plasmid decreases sensitivity of insertion detection is expected to improve.

(9) Detection of Insertion

Detection of insertion was performed using inverse PCR. Tol1 element contained in the donor plasmid lacks an EcoRI recognition site. If a Tol1 element is transferred into a silkworm chromosome and its genomic DNA is cut with EcoRI, then a DNA fragment including the Tol1 element would be cut out from the chromosome. T4 DNA ligase connects both ends of the EcoRI-cut DNA fragment to produce a circular DNA molecule. Primers Pin1 and Pin2 are annealed to both ends of Tol1 element and directed outward. PCR performed using these primers on the circular DNA molecules generates a PCR product corresponding to the length of the DNA inserted into the silkworm chromosome. The above-described sequential operations were performed to examine whether Tol1 element was inserted into a chromosome.

(10) Cloning and Sequencing

PCR products obtained in excision detection and insertion detection were cloned into a plasmid and the nucleotide sequences were mapped. The plasmid used for cloning was pT7Blue-2 (Takara Bio Inc., Otsu, Japan). A single-stranded DNA primer which annealed to a location about 100 bp upstream to the cloning point was used for sequencing.

(11) PCR Conditions

PCR was used in the above-described analysis. Ex Taq™ (Takara Bio Inc.) was used as the DNA polymerase. PCR conditions are described below.

2. Results (1) Detection of Excision

Figure 28:
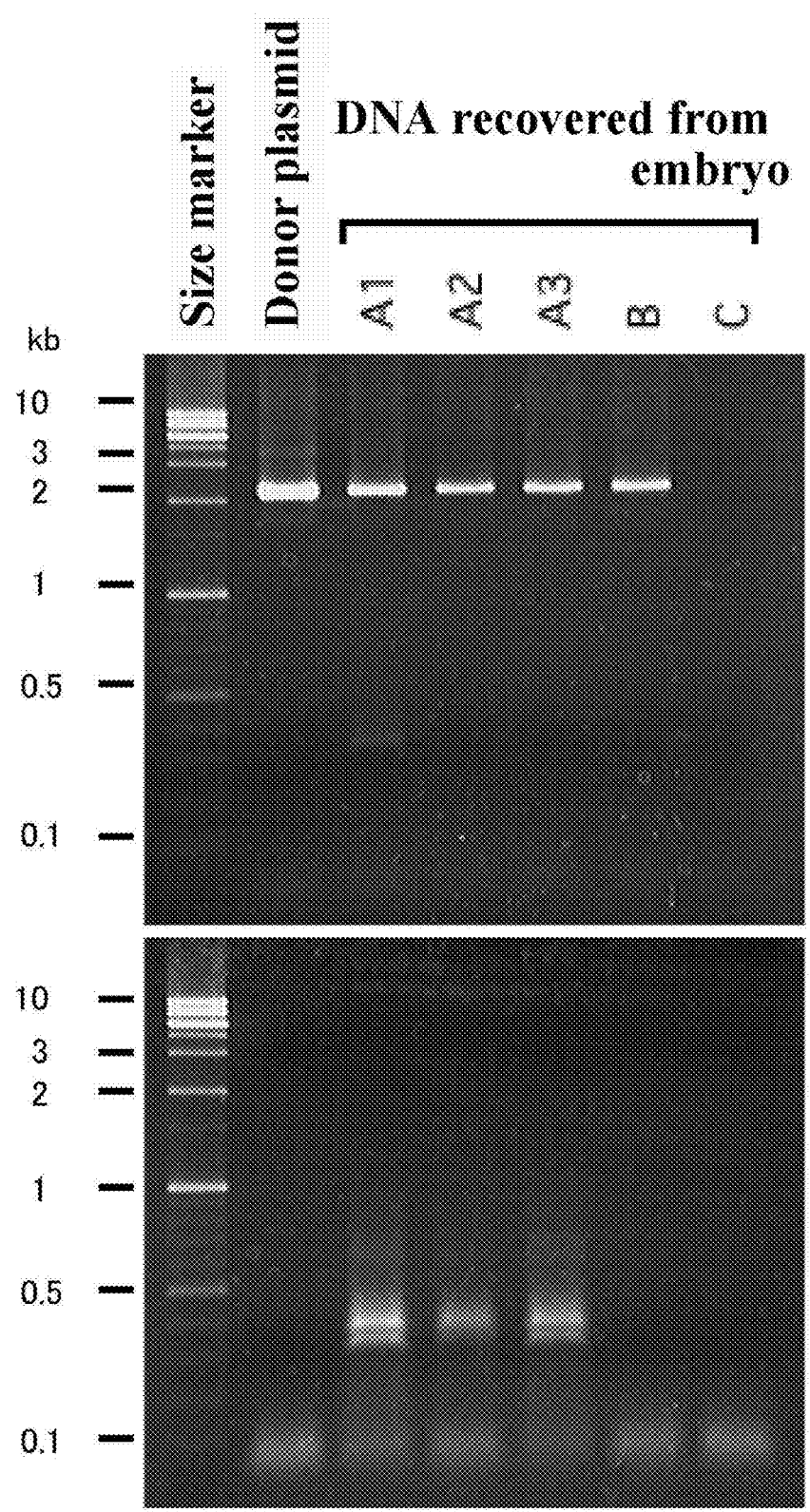
FIG. 28 shows PCR experiments for detecting excision. PCR was performed using a DNA template identified at the top of each lane. 10 pg of donor plasmid DNA was used in each PCR reaction; this is approximately the amount of DNA recovered from one embryo. Primers were Pex1 and Pex2.

For PCR templates, DNA was used which was extracted from a silkworm embryos that were warmed for 5 to 6 hours. PCR primers (Pex1 and Pex2), which are located so as to interpose Tol1 element therebetween on a donor plasmid, were used. PCR products were electrophoresed as shown in FIG. 28. PCR elongation was either for 150 seconds or 20 seconds. 150 seconds is sufficiently long to amplify 2.2 kb, which would include the whole region of Tol1 element on the donor plasmid. 2.2 kb PCR products were amplified from DNA extracted from condition A or B embryos, but not from embryos of condition C. Thus, 2.2 kb PCR products were derived from the injected donor plasmid, not from genomic DNA of a silkworm. The results further showed that the donor plasmids were recovered from embryos of either condition A or B.

Elongation for 20 seconds was carried out to efficiently amplify a PCR product from a DNA molecule in which excision had occurred. PCR products from DNA of embryos of set A1, A2, or A3 were around 0.3 kb long. 0.3 kb PCR products were not observed from DNA of embryos of condition B or C. These results suggested that excision of Tol1 element occurred only in the embryos of condition A.

(2) Confirmation of Excision

PCR products from A1, A2 and A3 were purified by ethanol precipitation and then ligated into plasmid vectors to form clones. One clone was randomly selected from each set and its nucleotide sequence was examined. Their sequences are aligned in FIG. 29. As seen in the Figure, Tol1 element regions were absent in all three clones. Further, a part of each side's target site duplication (TSD) region remained. Then, 8 to 80 bp of newly added DNA was located therebetween. Nucleotide sequences of newly added DNAs were compared to the whole nucleotide sequence of Tol1 element, but no homology portion was identified. The nucleotide sequence of TSD is CCTTTAGC (SEQ ID NO: 13), and its complementary sequence is GCTAAAGG. In many of the newly added DNAs, whole or a part of this complementary sequence seems to be continuous.

The cloning and sequencing of a PCR product clearly indicates that the whole region of Tol1 element disappeared. Thus confirming that excision of Tol1 element from the donor plasmid had occurred.

(3) Detection and Confirmation of Insertion

Genomic DNA was extracted from an embryo of condition A which was warmed for 96 to 97 hours. The genomic DNA was EcoRI digested and circularized as described above. Then, inverse PCR was performed and the product was cloned into a plasmid. When several tens of clones were obtained as bacterial colonies, two colonies were randomly selected. Plasmid DNA was extracted and sequenced. The corresponding portions are aligned in FIG. 30.

In three samples, nucleotide sequences of Tol1 element portions were confirmed and portions outside Tol1 element were not identical. When only the sequences of the outside portions were taken out from clone of a silkworm and checked with the nucleotide sequence database of silkworms (KAIOKOBLAST; See the World Wide Web (www) kaikoblast.dna.affrc.go.jp/), it was found that sequences having 90% or more homology was present in the silkworm genome. In addition, TSD was not found.

From analysis of a nucleotide sequence of an inverse PCR product, a Tol1 element portion was shown to be connected to a silkworm chromosome. Thus, insertion of Tol1 element occurred in a silkworm.

3. Discussion

At an early stage of evolution, higher animals diverged into two large phyletic lines: protostomes and deuterostomes. Vertebrates, such as humans and medaka fish, are deuterostomes. Tol1 element is a DNA transposable element present in a genome of medaka fish, and was speculated to have a transposable activity in other vertebrates. Using silkworms as a model, this study examined whether the Tol1 element transfers in protostomes. The study clearly showed that transposition occurred in an exemplary protostome.

An enzyme catalyzing transposition of Tol1 element is a transfer enzyme of Tol1 element. However, it was uncertain whether a transfer reaction requires only this enzyme or whether other factors, present in a host cell, are necessary. The above-described results that Tol1 element transfers in a protostome inspired further analyses as to whether other factors are present in a host cell. In these further analyses, it was discovered that other factors present in a host cell are not necessary in a transfer reaction of Tol1 element; alternatively, even if other factors are necessary, they are present in cells of both protostomes and deuterostomes.

The above results have a significant meaning also in the field of biotechnology. First, the fact that Tol1 element transfers in a silkworm means that the methods of gene introduction, gene trapping, and mutagenesis, which are used in a silkworm, can be performed using Tol1 element. Further, as described below, it is likely that methods using Tol1 element have properties that exceed those of methods already developed.

In a silkworm, a method using piggyBac element (Cited document 9) and a system using Minos element (Cited document 11) have already been developed. Both of these elements belong to the mariner/Tc1 family. The mariner/Tc1 family is a group of transposable elements, which are similar in their structures and transfer mechanisms, that are present in a wide distribution of organisms. The group was named for the mariner element of *Drosophila* and the Tc1 element of nematode. In addition to the mariner/Tc1 family, another large group of transposable elements is called the hAT family, which includes hobo element of *Drosophila*, Activator element of corn, and Tam3 element of snapdragon (Cited document 1). Tol1 element of medaka fish, which was shown above to transfer in a silkworm, belongs to the hAT family (Cited document 6). The hAT family elements transfer even when the whole length is long, as compared to elements of the mariner/Tc1 family. For example, in an experiment using a cultured mouse cell, it was shown that when Sleeping Beauty element (a mariner/Tc1 family element) has a whole length exceeding 9.1 kb, transposable activity is nearly lost (Cited document 12). On the other hand, Tol1 element transfers in a cultured mouse cell at a high frequency even when the Tol1 element has a whole length of 22.1 kb (Cited document 4). Consequently, its use as a vector for introduction of a long DNA fragment into a chromosome is strongly expected. Industrially-useful genes with large whole lengths, such as a fibroin gene, are present in a silkworm and its related species (Cited document 8). For such genes, Tol1 element is expected to be useful vector.

The significance of the above-described results is not limited to the field of biotechnology in regards to silkworms. This is because, it is unlikely that silkworms, among the protostomes, are unique regarding transposition of Tol1 element. Thus, it is expected that Tol1 element will transfer also in other protostomes. Accordingly, it is expected that methods such as gene introduction, gene trapping, and mutagenesis, using Tol1 element, can be applied to a wide range of organisms.

CITED DOCUMENTS

1. Calvi B. R., Hong T. J., Findley S. D., Gelbart W. M. (1991). Evidence for a common evolutionary origin of inverted repeat transposons in *Drosophila* and plants: hobo, Activator, and Tam3. Cell 66: 465-471.
2. Hikosaka A., Koga A. (2007). PCR detection of excision suggests mobility of the medaka fish Tol1 transposable element in the frog *Xenopus laevis*. Genet. Res.: in press.
3. Hirt B. (1967). Selective extraction of polyoma DNA from infected mouse cell cultures. J. Mol. Biol. 26: 365-369.
4. Koga A., Higashide I., Hori H., Wakamatsu Y., Kyono-Hamaguchi Y., Hamaguchi S. (2007b). The Tol1 element of medaka fish is transposed with only terminal regions and can deliver large DNA fragments into the chromosomes. J. Hum. Genet. 52: 1026-1030.
5. Koga A., Inagaki H., Bessho Y., Hori H. (1995). Insertion of a novel transposable element in the tyrosinase gene is responsible for an albino mutation in the medaka fish, *Oryzias latipes*. Mol. Gen. Genet. 249: 400-405.
6. Koga A., Shimada A., Kuroki T., Hori H., Kusumi J., Kyono-Hamaguchi Y., Hamaguchi S. (2007a). The Tol1 transposable element of the medaka fish moves in human and mouse cells. J. Hum. Genet. 52: 628-635.
7. Sambrook J., Russell D. W. (2001) Molecular Cloning: A Laboratory Manual, 3rd Ed. Cold Spring Harbor Laboratory Press, Cold Spring Harbor
8. Sezutsu H., Yukuhiro K. (2000). Dynamic rearrangement within the *Antheraea pernyi* silk fibroin gene is associated with four types of repetitive units. J. Mol. Evol. 51: 329-338.
9. Tamura T., Thibert C., Royer C., Kanda T., Abraham E., Kamba M., Komoto N., Thomas J. L., Mauchamp B., Chavancy G., Shirk P., Fraser M., Prudhomme J. C., Couble P. (2000).
10. Germline transformation of the silkworm *Bombyx mori* L. using a piggyBac transposon-derived vector. Nat. Biotechnol. 18: 81-84.
11. Uchino K., Imamura M., Shimizu K., Kanda T., Tamura T. (2007). Germ line transformation of the silkworm, *Bombyx mori*, using the transposable element Minos. Mol. Genet. Genomics 277: 213-220.
12. Karsi A., Moav B., Hackett P., Liu Z. (2001) Effects of insert size on transposition efficiency of the Sleeping Beauty transposon in mouse cells. Mar Biotechnol 3: 241-245.

INDUSTRIAL APPLICABILITY

The present invention provides a Tol1 element transposase, a DNA introduction system using the same, and the like. The present invention is intended for applications such as gene introduction, gene targeting, mutagenesis, trapping of genes, promoters, enhancers, etc.

The present invention is not limited to the description of the above embodiments and examples of the invention. Various modified forms within the range where a skilled person can easily conceive of are also included in the invention without departing from the description of the scope of claims for the patent.

Entire contents of treatises, unexamined patent publications, patent publications, and the like, indicated in the present specification are hereby incorporated by reference.

The invention claimed is:

1. An isolated polynucleotide encoding a Tol1 element transposase, the isolated polynucleotide comprising any of the nucleotide sequences selected from the group consisting of:
   (a) a nucleotide sequence encoding the amino acid sequence of SEQ ID NO: 2; and
   (b) the nucleotide sequence set forth in SEQ ID NO: 1, SEQ ID NO: 3, or SEQ ID NO: 4.

2. An expression construct comprising the isolated polynucleotide according to claim 1 and a promoter operably linked to the polynucleotide.

3. The expression construct according to claim 2, further comprising a poly-A sequence connected downstream of the polynucleotide.

4. A reconstructed transposon comprising the isolated polynucleotide according to claim 1 and a Tol1 element, wherein the Tol1 element is a transposase gene-defective element.

5. The transposon according to claim 4, further comprising a promoter operably linked to the polynucleotide.

6. The transposon according to claim 4, further comprising a poly-A sequence connected downstream of the polynucleotide.

7. A DNA introduction system, comprising the transposon according to claim 4.

8. A DNA introducing kit comprising:
   a donor factor, wherein the donor factor is a recombinant vector comprising a Tol1 element and an insertion site, wherein the Tol1 element is a transposase gene-defective element; and
   a helper factor, wherein the helper factor is a recombinant vector comprising the isolated polynucleotide according to claim 1.

9. The DNA introducing kit according to claim 8, wherein the recombinant vector being the helper factor further comprises a promoter operably linked to the polynucleotide.

10. The DNA introducing kit according to claim 8, wherein the recombinant vector being the helper factor further comprises a poly-A sequence connected downstream of the polynucleotide.

* * * * *

SEQUENCE LISTING

<160> NUMBER OF SEQ ID NOS: 101

<210> SEQ ID NO 1
<211> LENGTH: 2556
<212> TYPE: DNA
<213> ORGANISM: Oryzias latipes

<400> SEQUENCE: 1

```
atggagaaaa aaggtcaaa gccatctggt gcccaattta gaaagaaaag aaaagaagaa      60
gaggagaaaa gagataaaga aaaggggggca cttctaagat attttggatc gtctaccact     120
gctcaagatg agacatctac ctccctgcca gctatctcat cagccacagt cacagtctca     180
ccccctcagg atgagctacc atctacatcc tctgctactc atgtagttcc acagttgtta     240
cctgagcaaa gttttgatag tgaggctgaa gacgttgttc catctacgtc tacccagctt     300
gagacttcag aaatgcctgg tgatgaaacc ccactgaccc cgactgctga ggaccagcct     360
ctaccaactg accctgcaaa gtggccctca cctctgactg acaggatacg gatggagctg     420
gttcgaagag gaccaagtag cataccacct gactttgttt tcccaagaaa tgacagtgat     480
gggagaagtt gtcatcacca ctatttcagg aagacactag taagtggtga aaaaatagca     540
agaacttggt tgatgtattc aaaagtgaag aacagcctct tttgcttttg ttgcaaattg     600
ttttccaaca aaacattaa tttaacaact tctggtacag caaactggaa acatgcaagc     660
acatacctca cagcacacga aaaaagccca gaacacctca attgtatgaa agcatggaag     720
gaactgtcag ggaggatcag aagtgggaaa acaattgata gcaggagat ggcacttctg     780 gaagaggagc gggtgagatg gagagcagtg ctaacccgtc tcattgctat tgtgcagtca     840
ctggcagttc ggaatttggc tctaagggga cacacagaaa cactgttcac atcatcaaat     900
gggaattttt tgaaagaggt tgaactgatg gccaggtttg atcccataat gaaagatcat     960
cttaaccgtg tattaagagg aacagcaagt cacaacagct acataggcca tcatgtgcag    1020
aatgaactta ttgatttgtt gagcagcaaa atcctatccg ctatagtgga tgacatcaaa    1080
aaggcaaaat attttttcaat aattctggac tgcactctgg atataagcca cacagaacag    1140
ttgtcagtta taattagagt ggtgtcactg atggagaagc ctcagatcag gaacatttt     1200 atggggtttt tggaggcaga ggagtccaca ggccagcact ggcatccat gatcttaaac     1260 agacttgagg agttaggaat ttctttttgaa gactgcagag acaatcata tgataatggg    1320 gcaaatatga aaggcaaaaa taagggagta caagccaggc tcttagaaaa gaatccccgt    1380
gctctgtttt tgccatgcgg tgcacacaca ttgaatttag ttgtgtgtga tgctgctaag    1440
agatctgttg atgctatgag ctactttggt gtcctgcaaa agctttacac tttatttca    1500 gcctctgccc aacgatgggc catactgaag agtcaggtga gcatcactct aaagtcgtgg    1560
acagaaacaa ggtgggagag caaaatcaaa agcatcgagc ccatgaggta ccagggagct    1620
gcagtgagag aggctttaat agaagtgaga gacaagacca agacccagt tataaaggct    1680 gaggcccagt ctttgtctga agaggtaggg tcgtaccgct tcaacatctg cacagtcgta    1740
tggcatgaca ttctatctac aataaagcat gtcagcaaac tcatgcagtc tccaaatatg    1800
catgtggacc tagctgtgag tcttttgaag aagactgaac aaagtctcca gagctacagg    1860
gcaaatggct ttgtgaatgc acagatggca gccaaagaaa tgtgcaagga atgaatgtc    1920 gaggctattt tgaaacaaaa aagaataaga tccacaaagt gccaattctc gtatgaatca    1980
cacgatgagc ctttcagtga cgcacttaaa aagttggagg ttgaattttt caatgttgtt    2040
```

```
gttgatgaag ccttgtcagc catcgcggag aggttttcca cattggaagt tgtacaaaac    2100
agatttgggg ttttgaccaa tttcccaagc cttggagacg aggagctgac ggagcaatgc    2160
gaggcactag gcaacatact ccattttgag aagaactggg atttggacag tagagagctt    2220
gttcaggaaa tcaagaactt gcctaactta ccatcaacga ctccaagtct ccttgagctc    2280
atctctttca tgtctgataa ggatctatca gaaatctatc cgaacttttg gactgctctc    2340
aggattgcac tcaccttgcc agtcactgtg gctcaagcag agaggagctt ttcaaaacta    2400
aaattgatca agtcgtacct gaggtcaaca atgtcacagg agcgactcac taaccttgcc    2460
gttgttagca tcaatcactc agtaggggag cagatatcat atgatgatgt tattgacgag    2520
tttgcatcaa gaaaggctag gaaggttagg ttttag                              2556

<210> SEQ ID NO 2
<211> LENGTH: 851
<212> TYPE: PRT
<213> ORGANISM: Oryzias latipes

<400> SEQUENCE: 2

Met Glu Lys Lys Arg Ser Lys Pro Ser Gly Ala Gln Phe Arg Lys Lys
1               5                   10                  15

Arg Lys Glu Glu Glu Lys Arg Asp Lys Glu Lys Gly Ala Leu Leu
            20                  25                  30

Arg Tyr Phe Gly Ser Ser Thr Thr Ala Gln Asp Glu Thr Ser Thr Ser
        35                  40                  45

Leu Pro Ala Ile Ser Ser Ala Thr Val Thr Val Ser Pro Pro Gln Asp
    50                  55                  60

Glu Leu Pro Ser Thr Ser Ser Ala Thr His Val Val Pro Gln Leu Leu
65                  70                  75                  80

Pro Glu Gln Ser Phe Asp Ser Glu Ala Glu Asp Val Val Pro Ser Thr
                85                  90                  95

Ser Thr Gln Leu Glu Thr Ser Glu Met Pro Gly Asp Glu Thr Pro Leu
            100                 105                 110

Thr Pro Thr Ala Glu Asp Gln Pro Leu Pro Thr Asp Pro Ala Lys Trp
        115                 120                 125

Pro Ser Pro Leu Thr Asp Arg Ile Arg Met Glu Leu Val Arg Arg Gly
    130                 135                 140

Pro Ser Ser Ile Pro Pro Asp Phe Val Phe Pro Arg Asn Asp Ser Asp
145                 150                 155                 160

Gly Arg Ser Cys His His Tyr Phe Arg Lys Thr Leu Val Ser Gly
                165                 170                 175

Glu Lys Ile Ala Arg Thr Trp Leu Met Tyr Ser Lys Val Lys Asn Ser
            180                 185                 190

Leu Phe Cys Phe Cys Lys Leu Phe Ser Asn Lys Asn Ile Asn Leu
        195                 200                 205

Thr Thr Ser Gly Thr Ala Asn Trp Lys His Ala Ser Thr Tyr Leu Thr
    210                 215                 220

Ala His Glu Lys Ser Pro Glu His Leu Asn Cys Met Lys Ala Trp Lys
225                 230                 235                 240

Glu Leu Ser Gly Arg Ile Arg Ser Gly Lys Thr Ile Asp Lys Gln Glu
                245                 250                 255

Met Ala Leu Leu Glu Glu Glu Arg Val Arg Trp Arg Ala Val Leu Thr
            260                 265                 270

Arg Leu Ile Ala Ile Val Gln Ser Leu Ala Val Arg Asn Leu Ala Leu
        275                 280                 285
```

```
Arg Gly His Thr Glu Thr Leu Phe Thr Ser Ser Asn Gly Asn Phe Leu
    290                 295                 300
Lys Glu Val Glu Leu Met Ala Arg Phe Asp Pro Ile Met Lys Asp His
305                 310                 315                 320
Leu Asn Arg Val Leu Arg Gly Thr Ala Ser His Asn Ser Tyr Ile Gly
                325                 330                 335
His His Val Gln Asn Glu Leu Ile Asp Leu Leu Ser Ser Lys Ile Leu
            340                 345                 350
Ser Ala Ile Val Asp Asp Ile Lys Lys Ala Lys Tyr Phe Ser Ile Ile
        355                 360                 365
Leu Asp Cys Thr Leu Asp Ile Ser His Thr Glu Gln Leu Ser Val Ile
370                 375                 380
Ile Arg Val Val Ser Leu Met Glu Lys Pro Gln Ile Arg Glu His Phe
385                 390                 395                 400
Met Gly Phe Leu Glu Ala Glu Ser Thr Gly Gln His Leu Ala Ser
                405                 410                 415
Met Ile Leu Asn Arg Leu Glu Glu Leu Gly Ile Ser Phe Glu Asp Cys
            420                 425                 430
Arg Gly Gln Ser Tyr Asp Asn Gly Ala Asn Met Lys Gly Lys Asn Lys
        435                 440                 445
Gly Val Gln Ala Arg Leu Leu Glu Lys Asn Pro Arg Ala Leu Phe Leu
    450                 455                 460
Pro Cys Gly Ala His Thr Leu Asn Leu Val Val Cys Asp Ala Ala Lys
465                 470                 475                 480
Arg Ser Val Asp Ala Met Ser Tyr Phe Gly Val Leu Gln Lys Leu Tyr
                485                 490                 495
Thr Leu Phe Ser Ala Ser Ala Gln Arg Trp Ala Ile Leu Lys Ser Gln
            500                 505                 510
Val Ser Ile Thr Leu Lys Ser Trp Thr Glu Thr Arg Trp Glu Ser Lys
        515                 520                 525
Ile Lys Ser Ile Glu Pro Met Arg Tyr Gln Gly Ala Ala Val Arg Glu
        530                 535                 540
Ala Leu Ile Glu Val Arg Asp Lys Thr Lys Asp Pro Val Ile Lys Ala
545                 550                 555                 560
Glu Ala Gln Ser Leu Ser Glu Glu Val Gly Ser Tyr Arg Phe Asn Ile
                565                 570                 575
Cys Thr Val Val Trp His Asp Ile Leu Ser Thr Ile Lys His Val Ser
            580                 585                 590
Lys Leu Met Gln Ser Pro Asn Met His Val Asp Leu Ala Val Ser Leu
        595                 600                 605
Leu Lys Lys Thr Glu Gln Ser Leu Gln Ser Tyr Arg Ala Asn Gly Phe
    610                 615                 620
Val Asn Ala Gln Met Ala Ala Lys Glu Met Cys Lys Glu Met Asn Val
625                 630                 635                 640
Glu Ala Ile Leu Lys Gln Lys Arg Ile Arg Ser Thr Lys Cys Gln Phe
                645                 650                 655
Ser Tyr Glu Ser His Asp Glu Pro Phe Ser Asp Ala Leu Lys Lys Leu
            660                 665                 670
Glu Val Glu Phe Phe Asn Val Val Asp Glu Ala Leu Ser Ala Ile
        675                 680                 685
Ala Glu Arg Phe Ser Thr Leu Glu Val Gln Asn Arg Phe Gly Val
    690                 695                 700
Leu Thr Asn Phe Pro Ser Leu Gly Asp Glu Glu Leu Thr Glu Gln Cys
705                 710                 715                 720
```

```
Glu Ala Leu Gly Asn Ile Leu His Phe Glu Lys Asn Trp Asp Leu Asp
            725                 730                 735

Ser Arg Glu Leu Val Gln Glu Ile Lys Asn Leu Pro Asn Leu Pro Ser
        740                 745                 750

Thr Thr Pro Ser Leu Leu Glu Leu Ile Ser Phe Met Ser Asp Lys Asp
            755                 760                 765

Leu Ser Glu Ile Tyr Pro Asn Phe Trp Thr Ala Leu Arg Ile Ala Leu
        770                 775                 780

Thr Leu Pro Val Thr Val Ala Gln Ala Glu Arg Ser Phe Ser Lys Leu
785                 790                 795                 800

Lys Leu Ile Lys Ser Tyr Leu Arg Ser Thr Met Ser Gln Glu Arg Leu
            805                 810                 815

Thr Asn Leu Ala Val Val Ser Ile Asn His Ser Val Gly Glu Gln Ile
            820                 825                 830

Ser Tyr Asp Asp Val Ile Asp Glu Phe Ala Ser Arg Lys Ala Arg Lys
            835                 840                 845

Val Arg Phe
    850

<210> SEQ ID NO 3
<211> LENGTH: 2900
<212> TYPE: DNA
<213> ORGANISM: Oryzias latipes
<220> FEATURE:
<221> NAME/KEY: CDS
<222> LOCATION: (48)..(2600)

<400> SEQUENCE: 3
tgacgtgagg acatttatgc caaacaaacg ccaaaaacat ctaaaat atg gag aaa      56
                                                  Met Glu Lys
                                                    1 aaa agg tca aag cca tct ggt gcc caa ttt aga aag aaa aga aaa gaa    104
Lys Arg Ser Lys Pro Ser Gly Ala Gln Phe Arg Lys Lys Arg Lys Glu
        5                  10                  15 gaa gag gag aaa aga gat aaa gaa aag ggg gca ctt cta aga tat ttt    152
Glu Glu Glu Lys Arg Asp Lys Glu Lys Gly Ala Leu Leu Arg Tyr Phe
 20                  25                  30                  35 gga tcg tct acc act gct caa gat gag aca tct acc tcc ctg cca gct    200
Gly Ser Ser Thr Thr Ala Gln Asp Glu Thr Ser Thr Ser Leu Pro Ala
                 40                  45                  50 atc tca tca gcc aca gtc aca gtc tca ccc cct cag gat gag cta cca    248
Ile Ser Ser Ala Thr Val Thr Val Ser Pro Pro Gln Asp Glu Leu Pro
             55                  60                  65 tct aca tcc tct gct act cat gta gtt cca cag ttg tta cct gag caa    296
Ser Thr Ser Ser Ala Thr His Val Val Pro Gln Leu Leu Pro Glu Gln
         70                  75                  80 agt ttt gat agt gag gct gaa gac gtt gtt cca tct acg tct acc cag    344
Ser Phe Asp Ser Glu Ala Glu Asp Val Val Pro Ser Thr Ser Thr Gln
 85                  90                  95 ctt gag act tca gaa atg cct ggt gat gaa acc cca ctg acc ccg act    392
Leu Glu Thr Ser Glu Met Pro Gly Asp Glu Thr Pro Leu Thr Pro Thr
100                 105                 110                 115 gct gag gac cag cct cta cca act gac cct gca aag tgg ccc tca cct    440
Ala Glu Asp Gln Pro Leu Pro Thr Asp Pro Ala Lys Trp Pro Ser Pro
                120                 125                 130 ctg act gac agg ata cgg atg gag ctg gtt cga aga gga cca agt agc    488
Leu Thr Asp Arg Ile Arg Met Glu Leu Val Arg Arg Gly Pro Ser Ser
            135                 140                 145 ata cca cct gac ttt gtt ttc cca aga aat gac agt gat ggg aga agt    536
Ile Pro Pro Asp Phe Val Phe Pro Arg Asn Asp Ser Asp Gly Arg Ser
```

```
              Ile Pro Pro Asp Phe Val Phe Pro Arg Asn Asp Ser Asp Gly Arg Ser
                      150                 155                 160 tgt cat cac cac tat ttc agg aag aca cta gta agt ggt gaa aaa ata           584
Cys His His His Tyr Phe Arg Lys Thr Leu Val Ser Gly Glu Lys Ile
165                 170                 175 gca aga act tgg ttg atg tat tca aaa gtg aag aac agc ctc ttt tgc           632
Ala Arg Thr Trp Leu Met Tyr Ser Lys Val Lys Asn Ser Leu Phe Cys
180                 185                 190                 195 ttt tgt tgc aaa ttg ttt tcc aac aaa aac att aat tta aca act tct           680
Phe Cys Cys Lys Leu Phe Ser Asn Lys Asn Ile Asn Leu Thr Thr Ser
                200                 205                 210 ggt aca gca aac tgg aaa cat gca agc aca tac ctc aca gca cac gaa           728
Gly Thr Ala Asn Trp Lys His Ala Ser Thr Tyr Leu Thr Ala His Glu
            215                 220                 225 aaa agc cca gaa cac ctc aat tgt atg aaa gca tgg aag gaa ctg tca           776
Lys Ser Pro Glu His Leu Asn Cys Met Lys Ala Trp Lys Glu Leu Ser
        230                 235                 240 ggg agg atc aga agt ggg aaa aca att gat aag cag gag atg gca ctt           824
Gly Arg Ile Arg Ser Gly Lys Thr Ile Asp Lys Gln Glu Met Ala Leu
    245                 250                 255 ctg gaa gag gag cgg gtg aga tgg aga gca gtg cta acc cgt ctc att           872
Leu Glu Glu Glu Arg Val Arg Trp Arg Ala Val Leu Thr Arg Leu Ile
260                 265                 270                 275 gct att gtg cag tca ctg gca gtt cgg aat ttg gct cta agg gga cac           920
Ala Ile Val Gln Ser Leu Ala Val Arg Asn Leu Ala Leu Arg Gly His
                280                 285                 290 aca gaa aca ctg ttc aca tca tca aat ggg aat ttt ttg aaa gag gtt           968
Thr Glu Thr Leu Phe Thr Ser Ser Asn Gly Asn Phe Leu Lys Glu Val
            295                 300                 305 gaa ctg atg gcc agg ttt gat ccc ata atg aaa gat cat ctt aac cgt          1016
Glu Leu Met Ala Arg Phe Asp Pro Ile Met Lys Asp His Leu Asn Arg
        310                 315                 320 gta tta aga gga aca gca agt cac aac agc tac ata ggc cat cat gtg          1064
Val Leu Arg Gly Thr Ala Ser His Asn Ser Tyr Ile Gly His His Val
    325                 330                 335 cag aat gaa ctt att gat ttg ttg agc agc aaa atc cta tcc gct ata          1112
Gln Asn Glu Leu Ile Asp Leu Leu Ser Ser Lys Ile Leu Ser Ala Ile
340                 345                 350                 355 gtg gat gac atc aaa aag gca aaa tat ttt tca ata att ctg gac tgc          1160
Val Asp Asp Ile Lys Lys Ala Lys Tyr Phe Ser Ile Ile Leu Asp Cys
                360                 365                 370 act ctg gat ata agc cac aca gaa cag ttg tca gtt ata att aga gtg          1208
Thr Leu Asp Ile Ser His Thr Glu Gln Leu Ser Val Ile Ile Arg Val
            375                 380                 385 gtg tca ctg atg gag aag cct cag atc agg gaa cat ttt atg ggg ttt          1256
Val Ser Leu Met Glu Lys Pro Gln Ile Arg Glu His Phe Met Gly Phe
        390                 395                 400 ttg gag gca gag gag tcc aca ggc cag cac ttg gca tcc atg atc tta          1304
Leu Glu Ala Glu Glu Ser Thr Gly Gln His Leu Ala Ser Met Ile Leu
    405                 410                 415 aac aga ctt gag gag tta gga att tct ttt gaa gac tgc aga gga caa          1352
Asn Arg Leu Glu Glu Leu Gly Ile Ser Phe Glu Asp Cys Arg Gly Gln
420                 425                 430                 435 tca tat gat aat ggg gca aat atg aaa ggc aaa aat aag gga gta caa          1400
Ser Tyr Asp Asn Gly Ala Asn Met Lys Gly Lys Asn Lys Gly Val Gln
                440                 445                 450 gcc agg ctc tta gaa aag aat ccc cgt gct ctg ttt ttg cca tgc ggt          1448
Ala Arg Leu Leu Glu Lys Asn Pro Arg Ala Leu Phe Leu Pro Cys Gly
            455                 460                 465 gca cac aca ttg aat tta gtt gtg tgt gat gct gct aag aga tct gtt          1496
Ala His Thr Leu Asn Leu Val Val Cys Asp Ala Ala Lys Arg Ser Val
```

-continued

```
                Ala His Thr Leu Asn Leu Val Val Cys Asp Ala Ala Lys Arg Ser Val
                            470                 475                 480 gat gct atg agc tac ttt ggt gtc ctg caa aag ctt tac act tta ttt              1544
Asp Ala Met Ser Tyr Phe Gly Val Leu Gln Lys Leu Tyr Thr Leu Phe
485                 490                 495 tca gcc tct gcc caa cga tgg gcc ata ctg aag agt cag gtg agc atc              1592
Ser Ala Ser Ala Gln Arg Trp Ala Ile Leu Lys Ser Gln Val Ser Ile
500                 505                 510                 515 act cta aag tcg tgg aca gaa aca agg tgg gag agc aaa atc aaa agc              1640
Thr Leu Lys Ser Trp Thr Glu Thr Arg Trp Glu Ser Lys Ile Lys Ser
                520                 525                 530 atc gag ccc atg agg tac cag gga gct gca gtg aga gag gct tta ata              1688
Ile Glu Pro Met Arg Tyr Gln Gly Ala Ala Val Arg Glu Ala Leu Ile
            535                 540                 545 gaa gtg aga gac aag acc aaa gac cca gtt ata aag gct gag gcc cag              1736
Glu Val Arg Asp Lys Thr Lys Asp Pro Val Ile Lys Ala Glu Ala Gln
        550                 555                 560 tct ttg tct gaa gag gta ggg tcg tac cgc ttc aac atc tgc aca gtc              1784
Ser Leu Ser Glu Glu Val Gly Ser Tyr Arg Phe Asn Ile Cys Thr Val
565                 570                 575 gta tgg cat gac att cta tct aca ata aag cat gtc agc aaa ctc atg              1832
Val Trp His Asp Ile Leu Ser Thr Ile Lys His Val Ser Lys Leu Met
580                 585                 590                 595 cag tct cca aat atg cat gtg gac cta gct gtg agt ctt ttg aag aag              1880
Gln Ser Pro Asn Met His Val Asp Leu Ala Val Ser Leu Leu Lys Lys
                600                 605                 610 act gaa caa agt ctc cag agc tac agg gca aat ggc ttt gtg aat gca              1928
Thr Glu Gln Ser Leu Gln Ser Tyr Arg Ala Asn Gly Phe Val Asn Ala
            615                 620                 625 cag atg gca gcc aaa gaa atg tgc aag gaa atg aat gtc gag gct att              1976
Gln Met Ala Ala Lys Glu Met Cys Lys Glu Met Asn Val Glu Ala Ile
        630                 635                 640 ttg aaa caa aaa aga ata aga tcc aca aag tgc caa ttc tcg tat gaa              2024
Leu Lys Gln Lys Arg Ile Arg Ser Thr Lys Cys Gln Phe Ser Tyr Glu
645                 650                 655 tca cac gat gag cct ttc agt gac gca ctt aaa aag ttg gag gtt gaa              2072
Ser His Asp Glu Pro Phe Ser Asp Ala Leu Lys Lys Leu Glu Val Glu
660                 665                 670                 675 ttt ttc aat gtt gtt gtt gat gaa gcc ttg tca gcc atc gcg gag agg              2120
Phe Phe Asn Val Val Val Asp Glu Ala Leu Ser Ala Ile Ala Glu Arg
                680                 685                 690 ttt tcc aca ttg gaa gtt gta caa aac aga ttt ggg gtt ttg acc aat              2168
Phe Ser Thr Leu Glu Val Val Gln Asn Arg Phe Gly Val Leu Thr Asn
            695                 700                 705 ttc cca agc ctt gga gac gag gag ctg acg gag caa tgc gag gca cta              2216
Phe Pro Ser Leu Gly Asp Glu Glu Leu Thr Glu Gln Cys Glu Ala Leu
        710                 715                 720 ggc aac ata ctc cat ttt gag aag aac tgg gat ttg gac agt aga gag              2264
Gly Asn Ile Leu His Phe Glu Lys Asn Trp Asp Leu Asp Ser Arg Glu
725                 730                 735 ctt gtt cag gaa atc aag aac ttg cct aac tta cca tca acg act cca              2312
Leu Val Gln Glu Ile Lys Asn Leu Pro Asn Leu Pro Ser Thr Thr Pro
740                 745                 750                 755 agt ctc ctt gag ctc atc tct ttc atg tct gat aag gat cta tca gaa              2360
Ser Leu Leu Glu Leu Ile Ser Phe Met Ser Asp Lys Asp Leu Ser Glu
                760                 765                 770 atc tat ccg aac ttt tgg act gct ctc agg att gca ctc acc ttg cca              2408
Ile Tyr Pro Asn Phe Trp Thr Ala Leu Arg Ile Ala Leu Thr Leu Pro
            775                 780                 785 gtc act gtg gct caa gca gag agg agc ttt tca aaa cta aaa ttg atc              2456
```

```
                Val Thr Val Ala Gln Ala Glu Arg Ser Phe Ser Lys Leu Lys Leu Ile
                    790                 795                 800 aag tcg tac ctg agg tca aca atg tca cag gag cga ctc act aac ctt          2504
Lys Ser Tyr Leu Arg Ser Thr Met Ser Gln Glu Arg Leu Thr Asn Leu
    805                 810                 815 gcc gtt gtt agc atc aat cac tca gta ggg gag cag ata tca tat gat          2552
Ala Val Val Ser Ile Asn His Ser Val Gly Glu Gln Ile Ser Tyr Asp
820                 825                 830                 835 gat gtt att gac gag ttt gca tca aga aag gct agg aag gtt agg ttt          2600
Asp Val Ile Asp Glu Phe Ala Ser Arg Lys Ala Arg Lys Val Arg Phe
                840                 845                 850 tagttggtgt ttctgttat tgtattggtg ctgcagttat atttatttta gcgtgtcatt         2660
tgtgtgataa aaggtttgtg ctttataata tttattttat attatttatt caatattgag        2720
tttgattcaa tattttctta gctaactgta tttttgccat gcttatggtc ttttattttt        2780
tgtgttctta taactattat aatgctgttc agaattctga catcttttgt atccacttct        2840
taatttcaat gacaataaaa catgtcagtt gacaaagaca aaaaaaaaaa aaaaaaaaa         2900

<210> SEQ ID NO 4
<211> LENGTH: 4355
<212> TYPE: DNA
<213> ORGANISM: Oryzias latipes

<400> SEQUENCE: 4
cagtagcggt tctaggcacg ggccgtccgg gcggttgcct ggggcggaaa actgaagggg          60
ggcggcaccg gcggctcagc cctcgtaaaa tattatatgc accactattg gtttacttat         120
gtcacagttt gtgagtttgt aacagcctga acctggccgc gccgccgccc tcgccccgca         180
gctgcgctct cctgtctttg agaagtagac acaaatgtgt gtgaagaagg agaagggagg         240
gggcgcaggg tgagcacgga gcgccgccgc gtttgcgcat gcgcaaaaac ttgctggctc         300
atctttcagg ggaggcgacg gtcgcgggct tgatgaaaaa aataaaagta aaaactgcga         360
ctgcgccgtc atgtagcgaa tcagcgcccc tggctatagc tgcacgcgct cctgctggaa         420
atgtgtgaag aaaggggggg ggggggggct gcggggaatc agttcaattg tgggacgctt         480
ccaaattaag tggctaggtg gggacaaggg cgagggtttg aatctacttt ataaaacctt         540
tttataagtc agtcataagg tgacattcta taacctacat tttaataaag gtataaaaaa         600
atatattctg cttttgtggg ttaattttgt gtgaaatgcc caaatgaaaa aatggcaaca         660
caaaacaatg ctgtcactaa ggtgacagtt ggttcagtcg aaggacttga tgccttctcg         720
tgacgtgagg acatttatgc caaacaaacg ccaaaaacat ctaaaatatg agaaaaaaa          780 ggtcaaagcc atctggtgcc caatttagaa agaaaagaaa agaagaagag gagaaaagag         840
ataaagaaaa gggtaagtcc tcacagcttg atgcatgttt tttctaaatt ctaatgctac         900
ctgccctaca acaacgttgc cgatgaaaac tttattttgg tcgatgacca acactgaagt         960
aggcccaaat gttgcaaata gcatcatttt tttatttta gattttattc ttaaaaattt        1020
gagcctgcat atgaagttta ttttttattt gttttacaaa tgtgttatat ttttagccaa        1080
tagaatttcc ataaatctgt gggtagtttt aaaaaataat atttaccatt tactgcaact        1140
ctatggggac aaaacataat gtaacaggtc taaactaaaa atgtgccaat caaaggattg        1200
aagacgaaaa acatgagcta gttttcttc tctgaagtag agatcgatat agaacatgac         1260
aatttaaatt tccaattcat aaatgttttt ataaggccta tattgtagtc tatggtctttt        1320 tgaagtcagt atcaaatgca atttcagggg cacttctaag atattttgga tcgtctacca        1380
ctgctcaaga tgagacatct acctccctgc cagctatctc atcagccaca gtcacagtct        1440
```

```
cacccectca ggatgagcta ccatctacat cctctgctac tcatgtagtt ccacagttgt   1500
tacctgagca aagttttgat agtgaggctg aagacgttgt tccatctacg tctacccagc   1560
ttgagacttc aggtgggttt ttgtgtgtgt gagtgtacat gtgtaggtaa aaagacaatt   1620
gttcaactac aattgaatgt aatttttata attccgactt tgatgagta ggcctattag    1680 tgatgtttga caccaaaatg tgctttgagt aatgtgccaa tgtgccctat gatgatagaa   1740
atgcctggtg atgaaacccc actgaccccg actgctgagg accagcctct accaactgac   1800
cctgcaaagt ggccctcacc tctgactgac aggatacgga tggagctggt tcgaagagga   1860
ccaagtagca taccacctga cttttgttttc ccaagaaatg acagtgatgg agaagttgt   1920 catcaccact atttcaggaa gacactagta agtggtgaaa aaatagcaag aacttggttg   1980
atgtattcaa aagtgaagaa cagcctcttt tgcttttgtt gcaaattgtt ttccaacaaa   2040
aacattaatt taacaacttc tggtacagca aactggaaac atgcaagcac atacctcaca   2100
gcacacgaaa aaagcccaga acacctcaat tgtatgaaag catggaagga actgtcaggg   2160
aggatcagaa gtgggaaaac aattgataag caggagatgg cacttctgga agaggagcgg   2220
gtgagatgga gagcagtgct aacccgtctc attgctattg tgcagtcact ggcagttcgg   2280
aatttggctc taaggggaca cacagaaaca ctgttcacat catcaaatgg gaattttttg   2340
aaagaggttg aactgatggc caggtttgat cccataatga aagatcatct taaccgtgta   2400
ttaagaggaa cagcaagtca acagctac ataggccatc atgtgcagaa tgaacttatt   2460
gatttgttga gcagcaaaat cctatccgct atagtggatg acatcaaaaa ggcaaaatat   2520
ttttcaataa ttctggactg cactctggat ataagccaca cagaacagtt gtcagttata   2580
attagagtgg tgtcactgat ggagaagcct cagatcaggg aacattttat ggggttttg   2640 gaggcagagg agtccacagg ccagcacttg gcatccatga tcttaaacag acttgaggag   2700
ttaggaattt cttttgaaga ctgcagagga caatcatatg ataatgggc aaatatgaaa   2760 ggcaaaaata agggagtaca agccaggctc ttagaaaaga tccccgtgc tctgttttg    2820 ccatgcggtg cacacacatt gaatttagtt gtgtgtgatg ctgctaagag atctgttgat   2880
gctatgagct actttggtgt cctgcaaaag ctttacactt tattttcagc ctctgcccaa   2940
cgatgggcca tactgaagag tcaggtgagc atcactctaa agtcgtggac agaaacaagg   3000
tgggagagca aaatcaaaag catcgagccc atgaggtacc agggagctgc agtgagagag   3060
gctttaatag aagtgagaga caagaccaaa gacccagtta taaaggctga ggcccagtct   3120
ttgtctgaag aggtagggtc gtaccgcttc aacatctgca cagtcgtatg gcatgacatt   3180
ctatctacaa taaagcatgt cagcaaactc atgcagtctc caaatatgca tgtggaccta   3240
gctgtgagtc ttttgaagaa gactgaacaa agtctccaga gctacagggc aaatggcttt   3300
gtgaatgcac agatggcagc caaagaaatg tgcaaggaaa tgaatgtcga ggctattttg   3360
aaacaaaaaa gaataagatc cacaaagtgc caattctcgt atgaatcaca cgatgagcct   3420
ttcagtgacg cacttaaaaa gttggaggtt gaattttca atgttgttgt tgatgaagcc   3480
ttgtcagcca tcgcggagag gttttccaca ttggaagttg tacaaaacag atttggggtt   3540
ttgaccaatt tcccaagcct tggagacgag gagctgacgg agcaatgcga ggcactaggc   3600
aacatactcc attttgagaa gaactgggat ttggacagta gagagcttgt tcaggaaatc   3660
aagaacttgc ctaacttacc atcaacgact ccaagtctcc ttgagctcat ctctttcatg   3720
tctgataagg atctatcaga aatctatccg aacttttgga ctgctctcag gattgcactc   3780
accttgccag tcactgtggc tcaagcagag aggagctttt caaaactaaa attgatcaag   3840
```

```
tcgtacctga ggtcaacaat gtcacaggag cgactcacta accttgccgt tgttagcatc      3900
aatcactcag taggggagca gatatcatat gatgatgtta ttgacgagtt tgcatcaaga      3960
aaggctagga aggttaggtt ttagttggtg ttttctgtta ttgtattggt gctgcagtta      4020
tatttatttt agcgtgtcat ttgtgtgata aaaggtttgt gctttataat atttatttta      4080
tattatttat tcaatattga gtttgattca atattttctt agctaactgt attttttgcca    4140 tgcttatggt cttttatttt ttgtgttctt ataactatta taatgctgtt cagaattctg     4200
acatcttttg tatccacttc ttaatttcaa tgacaataaa acatgtcagt tgacaaagac     4260
aaacaaagtt ttgttgtgac tatgggggggg ggggggggggg ggggcgcctg gggagggtct   4320
cgcccgggga gtaattcagg gtagaaccgc cactg                               4355
```

<210> SEQ ID NO 5
<211> LENGTH: 14
<212> TYPE: DNA
<213> ORGANISM: Oryzias latipes

<400> SEQUENCE: 5

```
cagtagcggt tcta                                                         14
```

<210> SEQ ID NO 6
<211> LENGTH: 14
<212> TYPE: DNA
<213> ORGANISM: Oryzias latipes

<400> SEQUENCE: 6

```
tagaaccgcc actg                                                         14
```

<210> SEQ ID NO 7
<211> LENGTH: 685
<212> TYPE: PRT
<213> ORGANISM: Oryzias latipes

<400> SEQUENCE: 7

Met Phe Ile Gly Pro Leu Glu Val Thr Ser Cys His Ile Tyr Tyr His
1               5                   10                  15

Asn Ala Gln His Leu Asp Leu Glu Ile Arg Glu Ile Ile Thr Val Asn
                20                  25                  30

Gln Trp Lys Lys Met Glu Glu Val Cys Asp Ser Ser Ala Ala Ala Ser
            35                  40                  45

Ser Thr Val Gln Asn Gln Pro Gln Asp Gln His Pro Trp Pro Tyr
        50                  55                  60

Leu Arg Glu Phe Phe Ser Leu Ser Gly Val Asn Lys Asp Ser Phe Lys
65                  70                  75                  80

Met Lys Cys Val Leu Cys Leu Pro Leu Asn Lys Glu Ile Ser Ala Phe
                85                  90                  95

Lys Ser Ser Pro Ser Asn Leu Arg Lys His Ile Glu Arg Met His Pro
            100                 105                 110

Asn Tyr Leu Lys Asn Tyr Ser Lys Leu Thr Ala Gln Lys Arg Lys Ile
        115                 120                 125

Gly Thr Ser Thr His Ala Ser Ser Lys Gln Leu Lys Val Asp Ser
    130                 135                 140

Val Phe Pro Val Lys His Val Ser Pro Val Thr Val Asn Lys Ala Ile
145                 150                 155                 160

Leu Arg Tyr Ile Ile Gln Gly Leu His Pro Phe Ser Thr Val Asp Leu
                165                 170                 175

-continued

```
Pro Ser Phe Lys Glu Leu Ile Ser Thr Leu Gln Pro Gly Ile Ser Val
            180                 185                 190

Ile Thr Arg Pro Thr Leu Arg Ser Lys Ile Ala Glu Ala Ala Leu Ile
        195                 200                 205

Met Lys Gln Lys Val Thr Ala Ala Met Ser Glu Val Glu Trp Ile Ala
    210                 215                 220

Thr Thr Thr Asp Cys Trp Thr Ala Arg Arg Lys Ser Phe Ile Gly Val
225                 230                 235                 240

Thr Ala His Trp Ile Asn Pro Gly Ser Leu Glu Arg His Ser Ala Ala
                245                 250                 255

Leu Ala Cys Lys Arg Leu Met Gly Ser His Thr Phe Glu Val Leu Ala
            260                 265                 270

Ser Ala Met Asn Asp Ile His Ser Glu Tyr Glu Ile Arg Asp Lys Val
        275                 280                 285

Val Cys Thr Thr Thr Asp Ser Gly Ser Asn Phe Met Lys Ala Phe Arg
    290                 295                 300

Val Phe Gly Val Glu Asn Asn Asp Ile Glu Thr Ala Arg Arg Cys
305                 310                 315                 320

Glu Ser Asp Asp Thr Asp Ser Glu Gly Cys Gly Glu Gly Ser Asp Gly
                325                 330                 335

Val Glu Phe Gln Asp Ala Ser Arg Val Leu Asp Gln Asp Asp Gly Phe
            340                 345                 350

Glu Phe Gln Leu Pro Lys His Gln Lys Cys Ala Cys His Leu Leu Asn
        355                 360                 365

Leu Val Ser Ser Val Asp Ala Gln Lys Ala Leu Ser Asn Glu His Tyr
    370                 375                 380

Lys Lys Leu Tyr Arg Ser Val Phe Gly Lys Cys Gln Ala Leu Trp Asn
385                 390                 395                 400

Lys Ser Ser Arg Ser Ala Leu Ala Ala Glu Ala Val Glu Ser Glu Ser
                405                 410                 415

Arg Leu Gln Leu Leu Arg Pro Asn Gln Thr Arg Trp Asn Ser Thr Phe
            420                 425                 430

Met Ala Val Asp Arg Ile Leu Gln Ile Cys Lys Glu Ala Gly Glu Gly
        435                 440                 445

Ala Leu Arg Asn Ile Cys Thr Ser Leu Glu Val Pro Met Phe Asn Pro
    450                 455                 460

Ala Glu Met Leu Phe Leu Thr Glu Trp Ala Asn Thr Met Arg Pro Val
465                 470                 475                 480

Ala Lys Val Leu Asp Ile Leu Gln Ala Glu Thr Asn Thr Gln Leu Gly
                485                 490                 495

Trp Leu Leu Pro Ser Val His Gln Leu Ser Leu Lys Leu Gln Arg Leu
            500                 505                 510

His His Ser Leu Arg Tyr Cys Asp Pro Leu Val Asp Ala Leu Gln Gln
        515                 520                 525

Gly Ile Gln Thr Arg Phe Lys His Met Phe Glu Asp Pro Glu Ile Ile
    530                 535                 540

Ala Ala Ala Ile Leu Leu Pro Lys Phe Arg Thr Ser Trp Thr Asn Asp
545                 550                 555                 560

Glu Thr Ile Ile Lys Arg Gly Met Asp Tyr Ile Arg Val His Leu Glu
                565                 570                 575

Pro Leu Asp His Lys Lys Glu Leu Ala Asn Ser Ser Asp Asp Glu
            580                 585                 590

Asp Phe Phe Ala Ser Leu Lys Pro Thr Thr His Glu Ala Ser Lys Glu
        595                 600                 605
```

Leu Asp Gly Tyr Leu Ala Cys Val Ser Asp Thr Arg Glu Ser Leu Leu
            610                 615                 620

Thr Phe Pro Ala Ile Cys Ser Leu Ser Ile Lys Thr Asn Thr Pro Leu
625                 630                 635                 640

Pro Ala Ser Ala Ala Cys Glu Arg Leu Phe Ser Thr Ala Gly Leu Leu
                645                 650                 655

Phe Ser Pro Lys Arg Ala Arg Leu Asp Thr Asn Asn Phe Glu Asn Gln
            660                 665                 670

Leu Leu Leu Lys Leu Asn Leu Arg Phe Tyr Asn Phe Glu
        675                 680                 685

<210> SEQ ID NO 8
<211> LENGTH: 2319
<212> TYPE: DNA
<213> ORGANISM: Oryzias latipes

<400> SEQUENCE: 8

```
atttttgga gatcacttca ttctattttc ccttgctatt accaaaccaa ttgaattgcg      60
ctgatgccca gtttaattta aatgttattt attctgccta tgaaaatcgt tttcacatta    120
tatgaaattg gtcagacatg ttcattggtc ctttggaagt gacgtcatgt cacatctatt    180
accacaatgc acagcacctt gacctggaaa ttagggaaat tataacagtc aatcagtgga    240
agaaaatgga ggaagtatgt gattcatcag cagctgcgag cagcacagtc caaaatcagc    300
cacaggatca agagcacccg tggccgtatc ttcgcgaatt cttttcttta agtggtgtaa    360
ataaagattc attcaagatg aaatgtgtcc tctgtctccc gcttaataaa gaaatatcgg    420
ccttcaaaag ttcgccatca aacctaagga agcatattga gagaatgcac ccaaattacc    480
tcaaaaacta ctctaaattg acagcacaga agagaaagat cgggacctcc acccatgctt    540
ccagcagtaa gcaactgaaa gttgactcag ttttcccagt caaacatgtg tctccagtca    600
ctgtgaacaa agctatatta aggtacatca ttcaaggact tcatcctttc agcactgttg    660
atctgccatc atttaaagag ctgattagta cactgcagcc tggcatttct gtcattacaa    720
ggcctacttt acgctccaag atagctgaag ctgctctgat catgaaacag aaagtgactg    780
ctgccatgag tgaagttgaa tggattgcaa ccacaacgga ttgttggact gcacgtagaa    840
agtcattcat tggtgtaact gctcactgga tcaaccctgg aagtcttgaa agacattccg    900
ctgcacttgc ctgcaaaaga ttaatgggct ctcatacttt tgaggtactg ccagtgcca     960
tgaatgatat ccactcagag tatgaaatac gtgacaaggt tgtttgcaca accacagaca   1020
gtggttccaa ctttatgaag gctttcagag ttttttggtgt ggaaaacaat gatatcgaga   1080
ctgaggcaag aaggtgtgaa agtgatgaca ctgattctga aggctgtggt gagggaagtg   1140
atggtgtgga attccaagat gcctcacgag tcctggacca agacgatggc ttcgaattcc   1200
agctaccaaa acatcaaaag tgtgcctgtc acttacttaa cctagtctca agcgttgatg   1260
cccaaaaagc tctctcaaat gaacactaca agaaactcta cagatctgtc tttggcaaat   1320
gccaagcttt atggaataaa agcagccgat cggctctagc agctgaagct gttgaatcag   1380
aaagccggct tcagctttta aggccaaacc aaacgcggtg gaattcaact tttatggctg   1440
ttgacagaat tcttcaaatt tgcaaagaag caggagaagg cgcacttcgg aatatatgca   1500
cctctcttga ggttccaatg tttaatccag cagaaatgct gttcttgaca gagtgggcca   1560
acacaatgcg tccagttgca aaagtactcg acatcttgca agcggaaacg aatacacagc   1620
tggggtggct gctgcctagt gtccatcagt taagcttgaa acttcagcga ctccaccatt   1680
```

```
ctctcaggta ctgtgaccca cttgtggatg ccctacaaca aggaatccaa acacgattca   1740
agcatatgtt tgaagatcct gagatcatag cagctgccat ccttctccct aaatttcgga   1800
cctcttggac aaatgatgaa accatcataa acgaggcat ggactacatc agagtgcatc    1860
tggagccttt ggaccacaag aaggaattgg ccaacagttc atctgatgat gaagattttt   1920
tcgcttcttt gaaaccgaca acacatgaag ccagcaaaga gttggatgga tatctggcct   1980
gtgtttcaga caccagggag tctctgctca cgtttcctgc tatttgcagc ctctctatca   2040
agactaatac acctcttccc gcatcggctg cctgtgagag gcttttcagc actgcaggat   2100
tgcttttcag ccccaaaaga gctaggcttg acactaacaa ttttgagaat cagcttctac   2160
tgaagttaaa tctgaggttt tacaactttg agtagcgtgt actggcatta gattgtctgt   2220
cttatagttt gataattaaa tacaaacagt tctaaagcag gataaaacct tgtatgcatt   2280
tcatttaatg ttttttgaga ttaaaagctt aaacaagaa                          2319

<210> SEQ ID NO 9
<211> LENGTH: 4682
<212> TYPE: DNA
<213> ORGANISM: Oryzias latipes

<400> SEQUENCE: 9
cagaggtgta aagtacttga gtaattttac ttgattactg tacttaagta ttattttttgg    60 ggattttttac tttacttgag tacaattaaa aatcaatact tttactttta cttaattaca    120 ttttttttaga aaaaaagta cttttttactc cttacaattt tatttacagt caaaagtac     180 ttattttttg gagatcactt cattctattt tcccttgcta ttaccaaacc aattgaattg     240
cgctgatgcc cagtttaatt taaatgttat ttattctgcc tatgaaaatc gttttcacat     300
tatatgaaat tggtcagaca tgttcattgg tcctttggaa gtgacgtcat gtcacatcta     360
ttaccacaat gcacagcacc ttgacctgga aattagggaa attataacag tcaatcagtg     420
gaagaaaatg gaggaagtat gtgattcatc agcagctgcg agcagcacag tccaaaatca     480
gccacaggat caagagcacc cgtggccgta tcttcgcgaa ttcttttctt taagtggtgt     540
aaataaagat tcattcaaga tgaaatgtgt cctctgtctc ccgcttaata agaaatatc      600 ggccttcaaa agttcgccat caaacctaag gaagcatatt gaggtaagta cattaagtat     660
tttgttttac tgatagtttt ttttttttttt ttttttttttt ttttgggtg tgcatgtttt     720 gacgttgatg gcgcgccttt tatatgtgta gtaggcctat tttcactaat gcatgcgatt     780
gacaatataa ggctcacgta ataaaatgct aaaatgcatt tgtaattggt aacgttaggt     840
ccacgggaaa tttggcgcct attgcagctt tgaataatca ttatcattcc gtgctctcat     900
tgtgtttgaa ttcatgcaaa acacaagaaa accaagcgag aaattttttt ccaaacatgt     960
tgtattgtca aaacggtaac actttacaat gaggttgatt agttcatgta ttaactaaca   1020
ttaaataacc atgagcaata catttgttac tgtatctgtt aatctttgtt aacgttagtt   1080
aatagaaata cagatgttca ttgtttgttc atgttagttc acagtgcatt aactaatgtt   1140
aacaagatat aaagtattag taaatgttga aattaacatg tatacgtgca gttcattatt   1200
agttcatgtt aactaatgta gttaactaac gaaccttatt gtaaaagtgt taccatcaaa   1260
actaatgtaa tgaaatcaat tcaccctgtc atgtcagcct tacagtcctg tgttttttgtc  1320 aatataatca gaaataaaat taatgtttga ttgtcactaa atgctactgt atttctaaaa   1380
tcaacaagta tttaacatta taagtgtgc aattggctgc aaatgtcagt tttattaaag    1440
ggttagttca cccaaaaatg aaaataatgt cattaatgac tcgccctcat gtcgttccaa   1500
```

```
gcccgtaaga cctccgttca tcttcagaac acagtttaag atattttaga tttagtccga    1560
gagctttctg tgcctccatt gagaatgtat gtacggtata ctgtccatgt ccagaaaggt    1620
aataaaaaca tcaaagtagt ccatgtgaca tcagtgggtt agttagaatt ttttgaagca    1680
tcgaatacat tttggtccaa aaataacaaa acctacgact ttattcggca ttgtattctc    1740
ttccgggtct gttgtcaatc cgcgttcacg acttcgcagt gacgctacaa tgctgaataa    1800
agtcgtaggt tttgttattt ttggaccaaa atgtattttc gatgcttcaa ataattctac    1860
ctaacccact gatgtcacat ggactacttt gatgttttta ttacctttct ggacatggac    1920
agtataccgt acatacattt tcagtggagg gacagaaagc tctcggacta aatctaaaat    1980
atcttaaact gtgttccgaa gatgaacgga ggtgttacgg gcttggaacg acatgagggt    2040
gagtcattaa tgcatctctt tcattttggg gtgaactaac cctttaatgc tgtaatcaga    2100
gagtgtatgt gtaattgtta catttattgc atacaatata aatatttatt tgttgttttt    2160
acagagaatg cacccaaatt acctcaaaaa ctactctaaa ttgacagcac agaagagaaa    2220
gatcgggacc tccacccatg cttccagcag taagcaactg aaagttgact cagttttccc    2280
agtcaaacat gtgtctccag tcactgtgaa caaagctata ttaaggtaca tcattcaagg    2340
acttcatcct ttcagcactg ttgatctgcc atcatttaaa gagctgatta gtacactgca    2400
gcctggcatt tctgtcatta caaggcctac tttacgctcc aagatagctg aagctgctct    2460
gatcatgaaa cagaaagtga ctgctgccat gagtgaagtt gaatggattg caaccacaac    2520
ggattgttgg actgcacgta gaaagtcatt cattggtgta actgctcact ggatcaaccc    2580
tggaagtctt gaaagacatt ccgctgcact tgcctgcaaa agattaatgg gctctcatac    2640
ttttgaggta ctggccagtg ccatgaatga tatccactca gagtatgaaa tacgtgacaa    2700
ggttgtttgc acaaccacag acagtggttc caactttatg aaggctttca gagttttgg    2760 tgtgaaaaac aatgatatcg agactgaggc aagaaggtgt gaaagtgatg acactgattc    2820
tgaaggctgt ggtgagggaa gtgatggtgt ggaattccaa gatgcctcac gagtcctgga    2880
ccaagacgat ggcttcgaat tccagctacc aaaacatcaa aagtgtgcct gtcacttact    2940
taacctagtc tcaagcgttg atgcccaaaa agctctctca aatgaacact acaagaaact    3000
ctacagatct gtctttggca aatgccaagc tttatggaat aaaagcagcc gatcggctct    3060
agcagctgaa gctgttgaat cagaaagccg gcttcagctt taaggccaa accaaacgcg    3120 gtggaattca acttttatgg ctgttgacag aattcttcaa atttgcaaag aagcaggaga    3180
aggcgcactt cggaatatat gcacctctct tgaggttcca atgtaagtgt ttttcccctc    3240
tatcgatgta aacaaatgtg ggttgttttt gtttaatact cttttgattat gctgatttct    3300 cctgtaggtt taatccagca gaaatgctgt tcttgacaga gtgggccaac acaatgcgtc    3360
cagttgcaaa agtactcgac atcttgcaag cggaaacgaa tacacagctg ggtggctgc    3420 tgcctagtgt ccatcagtta agcttgaaac ttcagcgact ccaccattct ctcaggtact    3480
gtgacccact tgtggatgcc ctacaacaag gaatccaaac acgattcaag catatgtttg    3540
aagatcctga gatcatagca gctgccatcc ttctccctaa atttcggacc tcttggacaa    3600
atgatgaaac catcataaaa cgaggtaaat gaatgcaagc aacatacact tgacgaattc    3660
taatctgggc aacctttgag ccataccaaa attattcttt tatttattta tttttgcact    3720
ttttaggaat gttatatccc atctttggct gtgatctcaa tatgaatatt gatgtaaagt    3780
attcttgcag caggttgtag ttatccctca gtgtttcttg aaaccaaact catatgtatc    3840
atatgtggtt tggaaatgca gttagatttt atgctaaaat aagggatttg catgattta    3900
```

| | | | |
|---|---|---|---|
| gatgtagatg | actgcacgta | aatgtagtta atgacaaaat ccataaaatt tgttcccagt | 3960 |
| cagaagcccc | tcaaccaaac | ttttctttgt gtctgctcac tgtgcttgta ggcatggact | 4020 |
| acatcagagt | gcatctggag | cctttggacc acaagaagga attggccaac agttcatctg | 4080 |
| atgatgaaga | ttttttcgct | tctttgaaac cgacaacaca tgaagccagc aaagagttgg | 4140 |
| atggatatct | ggcctgtgtt | tcagacacca gggagtctct gctcacgttt cctgctattt | 4200 |
| gcagcctctc | tatcaagact | aatacacctc ttcccgcatc ggctgcctgt gagaggcttt | 4260 |
| tcagcactgc | aggattgctt | ttcagcccca aaagagctag gcttgacact aacaattttg | 4320 |
| agaatcagct | tctactgaag | ttaaatctga ggttttacaa ctttgagtag cgtgtactgg | 4380 |
| cattagattg | tctgtcttat | agtttgataa ttaaatacaa acagttctaa agcaggataa | 4440 |
| aaccttgtat | gcatttcatt | taatgttttt tgagattaaa agcttaaaca agaatctcta | 4500 |
| gttttctttc | ttgcttttac | ttttacttcc ttaatactca agtacaattt taatggagta | 4560 |
| cttttttact | tttactcaag | taagattcta gccagatact tttactttta attgagtaaa | 4620 |
| attttcccta | agtacttgta | ctttcacttg agtaaaattt ttgagtactt tttacacctc | 4680 |
| tg | | | 4682 |

<210> SEQ ID NO 10
<211> LENGTH: 1855
<212> TYPE: DNA
<213> ORGANISM: Oryzias latipes

<400> SEQUENCE: 10

| | | | |
|---|---|---|---|
| cagtagcggt | tctaggcacg | ggccgtccgg gcggtggcct ggggcggaaa actgaagggg | 60 |
| ggcggcaccg | gcggctcagc | cctttgtaat atattaatat gcaccactat tggtttactt | 120 |
| atgtcacagt | ttgtaagttt | gtaacagcct gaacctggcc gcgccgccgc cctcgccccg | 180 |
| cagctgcgct | ctcctgtctt | tgagaagtag acacaaatgt gtgtgaagaa ggagaaggga | 240 |
| gggggcgcgg | ggtgagcacg | gagcgtcgcc gcgtttgcgc atgcgcaaaa cctggctggc | 300 |
| tcatctttca | ggggaggcga | cggtcgcggg cttgatgaaa aaaataaaag taaaaactgc | 360 |
| gactgcgccg | tcatgtagcg | aatcagcgcc cctggctgta gctgcacgcg ctcctgctgg | 420 |
| aaatgtgtga | agagggggggg | ggggggggggg gctgcgggga atcagttcaa ttgtgggacg | 480 |
| cttccaaatt | aagtggctag | gtggggacaa gggcgggggt tgaatctac ttcataaaac | 540 |
| cttttttatat | tataagtcag | tcataaggtg acattctata acctacattt taataaaggt | 600 |
| ataaaaaata | tattctgctt | tttttgggtt aattttgtgt gaaatgtcca aataaaaaaa | 660 |
| atggcaacac | aaaacaatgc | tgtcactaag gtgacagttg gttcagtcga cggacttgat | 720 |
| gccttcttcg | tgacgtgagg | acattatgc caaacaaacg ccaataaaca tctaaaatat | 780 |
| ggaaagaaa | aggtcaaagc | catctggtgc ccaatttaga aagaaaagaa agaagaaga | 840 |
| ggagaaaaga | gataaagaaa | agggtaagtc ctcacagctt gatgcatgtt ttttctaaat | 900 |
| tctaatgcta | cctgccctac | aacaacgttg ccgatgaaaa ctttatttg gtcgatgacc | 960 |
| aacactgaat | taggcccaaa | tgttgcaaat agcgtcattt ttttttttt ttttagattt | 1020 |
| tattcttaaa | aatttgctct | gccttaactt gtaacattag ttatgattca tgtgtctgtc | 1080 |
| tgctctgctg | taacacaaag | gttttgttgg gttttgctgt tgtatactag ctcataatgt | 1140 |
| taaaaagct | gtgatggtta | cacagcatgc tggtgctgcc ataagatgct aatggggcaa | 1200 |
| ataatttgag | attggtcatt | aatttaataa tcatttgtgg cagcctaaac gttttcacaa | 1260 |
| tgttttttttg | acatttaact | ggggatttag gggttaattt tgagcctgca tatgaagttt | 1320 |

```
attttttatt tgttttacaa atgtgggatt atatttttag ccaatagaat ttccataaat    1380
ctgtaggtag tttaaaaat gaatatttac catttactgc aactctatgg ggacaaaaca    1440
taatgtaaca ggtcataact aaaaatgtgc caatcaaagg attgaagacg gaaaacatga    1500
gttaattttt cttctctgaa gtagagatcg atatagaaca tgacaattta aatttccaat    1560
tcataaatgt ttttaaaata tttatttat attatttatt taacattgag tttgattcaa     1620
tattttctta gctaactgta ttttgccat gcttatggtc ttttattttt tgtgttctga     1680
taacttttat aatgcttttc agaatttga catcttttgt atccacttct taatttcaat    1740
gacaataaaa catttcagtt gacgaagaca aacaaagttc tgttgtgact atggggggg    1800 ggggcgcctg gggatggtct cgcccgggga gtaattcagg gtagaaccgc cactg         1855
```

<210> SEQ ID NO 11
<211> LENGTH: 969
<212> TYPE: DNA
<213> ORGANISM: Artificial Sequence
<220> FEATURE:
<223> OTHER INFORMATION: Description of Artificial Sequence: Synthetic
      incomplete Tol1 element polynucleotide in which internal
      886 nucleotide pairs of Tol1-tyr have been deleted

<400> SEQUENCE: 11

```
cagtagcggt tctaggcacg ggccgtccgg gcggtggcct ggggcggaaa actgaagggg    60
ggcggcaccg gcggctcagc cctttgtaat atattaatat gcaccactat tggtttactt    120
atgtcacagt ttgtaagttt gtaacagcct gaacctggcc gcgccgccgc cctcgccccg    180
cagctgcgct ctcctgtctt tgagaagtag acacaaatgt gtgtgaagaa ggagaaggga    240 ggggcgcgg ggtgagcacg gagcgtcgcc gcgtttgcgc atgctggtgc tgccataaga    300
tgctaatggg gcaaataatt tgagattggt cattaattta ataatcattt gtggcagcct    360
aaacgttttc acaatgtttt tttgacattt aactggggat ttaggggtta attttgagcc    420
tgcatatgaa gtttattttt tatttgtttt acaaatgtgg gattatattt ttagccaata    480
gaatttccat aaatctgtag gtagtttta aaatgaatat ttaccattta ctgcaactct    540
atggggacaa aacataatgt aacaggtcat aactaaaaat gtgccaatca aaggattgaa    600
gacggaaaac atgagttaat ttttcttctc tgaagtagag atcgatatag aacatgacaa    660
tttaaatttc caattcataa atgttttaa atatttatt ttatattatt tatttaacat    720
tgagtttgat tcaatatttt cttagctaac tgtattttg ccatgcttat ggtcttttat    780
tttttgtgtt ctgataactt ttataatgct tttcagaatt ttgacatctt ttgtatccac    840
ttcttaattt caatgacaat aaaacatttc agttgacgaa gacaaacaaa gttctgttgt    900
gactatgggg gggggggcg cctggggatg gtctcgcccg ggagtaatt cagggtagaa    960 ccgccactg                                                             969
```

<210> SEQ ID NO 12
<211> LENGTH: 297
<212> TYPE: DNA
<213> ORGANISM: Artificial Sequence
<220> FEATURE:
<223> OTHER INFORMATION: Description of Artificial Sequence: Synthetic
      incomplete Tol1 element polynucleotide in which internal
      1,576 nucleotide pairs of Tol1-tyr have been deleted and
      6 kinds of restriction sites have been incorporated

<400> SEQUENCE: 12

```
cagtagcggt tctaggcacg ggccgtccgg gcggtggcct ggggcggaaa actgaagggg    60
ggcggcaccg gcggctcagc cctttgtaat atattaatat gcaccactat tggtttactt    120
```

```
atgtcacagt tgtaagtttt gtaacagcct gaacctggat ccgaattcga tatcggtacc      180
ctgcagtcta gacatttcag ttgacgaaga caaacaaagt tctgttgtga ctatgggggg      240 gggggggcgcc tggggatggt ctcgcccggg gagtaattca gggtagaacc gccactg        297
```

```
<210> SEQ ID NO 13
<211> LENGTH: 8
<212> TYPE: DNA
<213> ORGANISM: Oryzias latipes

<400> SEQUENCE: 13 cctttagc                                                                8

<210> SEQ ID NO 14
<211> LENGTH: 8
<212> TYPE: DNA
<213> ORGANISM: Oryzias latipes

<400> SEQUENCE: 14 gtcccatc                                                                8

<210> SEQ ID NO 15
<211> LENGTH: 8
<212> TYPE: DNA
<213> ORGANISM: Oryzias latipes

<400> SEQUENCE: 15 gttgcagc                                                                8

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggatcgtct accactgctc aagatgagac                                       30

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctgaagtctc aagctgggta gacgta                                           26

<210> SEQ ID NO 18
<211> LENGTH: 1800
<212> TYPE: DNA
<213> ORGANISM: Artificial Sequence
<220> FEATURE:
<223> OTHER INFORMATION: Description of Artificial Sequence: Synthetic
      polynucleotide, part of plasmid pCMV-Tag1

<400> SEQUENCE: 18
aatgcgccgc tacagggcgc gtcaggtggc acttttcggg gaaatgtgcg cggaacccct      60
atttgtttat ttttctaaat acattcaaat atgtatccgc tcatgagaca ataaccctga     120
taaatgcttc aataatattg aaaaaggaag atcctgaggc ggaaagaac cagctgtgga     180
```

```
atgtgtgtca gttagggtgt ggaaagtccc caggctcccc agcaggcaga agtatgcaaa    240
gcatgcatct caattagtca gcaaccaggt gtggaaagtc cccaggctcc ccagcaggca    300
gaagtatgca aagcatgcat ctcaattagt cagcaaccat agtcccgccc ctaactccgc    360
ccatcccgcc cctaactccg cccagttccg cccattctcc gccccatggc tgactaattt    420 ttttttattta tgcagaggcc gaggccgcct cggcctctga gctattccag aagtagtgag    480
gaggcttttt tggaggccta ggcttttgca aagatcgatc aagagacagg atgaggatcg    540
tttcgcatga ttgaacaaga tggattgcac gcaggttctc cggccgcttg ggtggagagg    600
ctattcggct atgactgggc acaacagaca atcggctgct ctgatgccgc cgtgttccgg    660
ctgtcagcgc aggggcgccc ggttcttttt gtcaagaccg acctgtccgg tgccctgaat    720
gaactgcaag acgaggcagc gcggctatcg tggctggcca cgacgggcgt tccttgcgca    780
gctgtgctcg acgttgtcac tgaagcggga agggactggc tgctattggg cgaagtgccg    840
gggcaggatc tcctgtcatc tcaccttgct cctgccgaga agtatccat catggctgat    900 gcaatgcggc ggctgcatac gcttgatccg gctacctgcc cattcgacca ccaagcgaaa    960
catcgcatcg agcgagcacg tactcggatg aagccggtc ttgtcgatca ggatgatctg   1020
gacgaagaac atcaggggct cgcgccagcc gaactgttcg ccaggctcaa ggcgagcatg   1080
cccgacggcg aggatctcgt cgtgacccat ggcgatgcct gcttgccgaa tatcatggtg   1140
gaaaatggcc gcttttctgg attcatcgac tgtggccggc tgggtgtggc ggaccgctat   1200
caggacatag cgttggctac ccgtgatatt gctgaagaac ttggcggcga atgggctgac   1260
cgcttcctcg tgctttacgg tatcgccgct cccgattcgc agcgcatcgc cttctatcgc   1320
cttcttgacg agttcttctg agcgggactc tggggttcga atgaccgac caagcgacgc   1380 ccaacctgcc atcacgagat ttcgattcca ccgccgcctt ctatgaaagg ttgggcttcg   1440
gaatcgtttt ccgggacgcc ggctggatga tcctccagcg cggggatctc atgctggagt   1500
tcttcgccca ccctaggggg aggctaactg aaacacggaa ggagacaata ccggaaggaa   1560
cccgcgctat gacggcaata aaagacaga ataaaacgca cggtgttggg tcgtttgttc   1620
ataaacgcgg ggttcggtcc cagggctggc actctgtcga taccccaccg agaccccatt   1680
ggggccaata cgcccgcgtt tcttccttt ccccacccca cccccaagt tcgggtgaag   1740 gcccagggct cgcagccaac gtcggggcgg caggccctgc catagcctca ggttactcat   1800
```

<210> SEQ ID NO 19
<211> LENGTH: 2787
<212> TYPE: DNA
<213> ORGANISM: Oryzias latipes

<400> SEQUENCE: 19

```
ccaaaaacat ctaaaatatg gagaaaaaaa ggtcaaagcc atctggtgcc caatttagaa     60
agaaaagaaa agaagaagag gagaaaagag ataagaaaaa gggggcactt ctaagatatt    120
ttggatcgtc taccactgct caagatgaga catctacctc cctgccagct atctcatcag    180
ccacagtcac agtctcaccc cctcaggatg agctaccatc tacatcctct gctactcatg    240
tagttccaca gttgttacct gagcaaagtt ttgatagtga ggctgaagac gttgttccat    300
ctacgtctac ccagcttgag acttcagaaa tgctggtga tgaaacccca ctgaccccga    360
ctgctgagga ccagcctcta ccaactgacc ctgcaaagtg gccctcacct ctgactgaca    420
ggatacggat ggagctggtt cgaagaggac caagtagcat accacctgac tttgttttcc    480
caagaaatga cagtgatggg agaagttgtc atcaccacta tttcaggaag acactagtaa    540
```

```
gtggtgaaaa aatagcaaga acttggttga tgtattcaaa agtgaagaac agcctctttt      600
gcttttgttg caaattgttt tccaacaaaa acattaattt aacaacttct ggtacagcaa      660
actggaaaca tgcaagcaca tacctcacag cacacgaaaa aagcccagaa cacctcaatt      720
gtatgaaagc atggaaggaa ctgtcaggga ggatcagaaa tgggaaaaca attgataagc      780
aggagatggc acttctggaa gaggagcggg tgagatggag agcagtgcta acccgtctca      840
ttgctattgt gcagtcactg gcagttcgga atttggctct aagggacaca acagaaacac      900
tgttcacatc atcaaatggg aattttttga aagaggttga actgatggcc aggtttgatc      960
ccataatgaa agatcatctt aaccgtgtat aagaggaaac agcaagtcac aacagctaca     1020
taggccatca tgtgcagaat gaacttattg atttgttgag cagcaaaatc ctatccgcta     1080
tagtggatga catcaaaaag gcaaaatatt tttcaataat tctggactgc actctggata     1140
taagccacac agaacagttg tcagttataa ttagagtggt gtcactgatg gagaagcctc     1200
agatcaggga acattttatg gggttttttgg aggcagagga gtccacaggc cagcacttgg     1260
catccatgat cttaaacaga cttgaggagt taggaatttc ttttgaagac tgcagaggac     1320
aatcatatga taatgggca aatatgaaag gcaaaaataa gggagtacaa gccaggctct     1380
tagaaaagaa tccccgtgct ctgttttttgc catgcggtgc acacacattg aatttagttg     1440
tgtgtgatgc tgctaagaga tctgttgatg ctatgagcta cttttggtgtc ctgcaaaagc     1500 tttacacttt atttttcagcc tctgcccaac gatgggccat actgaagagt caggtgagca     1560
tcactctaaa gtcgtggaca gaaacaaggt gggagagcaa aatcaaaagc atcgagccca     1620
tgaggtacca gggagctgca gtgagagagg ctttaataga agtgagagac aagaccaaag     1680
acccagttat aaaggctgag gcccagtctt tgtctgaaga ggtagggtcg taccgcttca     1740
acatctgcac agtcgtatgg catgacattc tatctacaat aaagcatgtc agcaaactca     1800
tgcagtctcc aaatatgcat gtggacctag ctgtgagtct tttgaagaag actgaacaaa     1860
gtctccagag ctacagggca aatggctttg tgaatgcaca gatggcagcc aaagaaatgt     1920
gcaaggaaat gaatgtcgag gctattttga aacaaaaaag aataagatcc acaaagtgcc     1980
aattctcgta tgaatcacac gatgagcctt tcagtgacgc acttaaaaag ttggaggttg     2040 aattttttcaa tgttgttgtt gatgaagcct tgtcagccat cgcggagagg ttttccacat     2100
tggaagttgt acaaaacaga tttggggttt tgaccaattt cccaagcctt ggagacgagg     2160
agctgacgga gcaatgcgag gcactaggca acatactcca ttttgagaag aactgggatt     2220
tggacagtag agagccttgtt caggaaatca agaacttgcc taacttacca tcaacgactc     2280
caagtctcct tgagctcatc tcttttcatgt ctgataagga tctatcagaa atctatccga     2340
acttttggac tgctctcagg attgcactca ccttgccagt cactgtggct caagcagaga     2400
ggagcttttc aaaaactaaa ttgatcaagt cgtacctgag gtcaacaatg tcacaggagc     2460
gactcactaa ccttgccgtt gttagcatca atcactcagt aggggagcag atatcatatg     2520
atgatgttat tgacgagttt gcatcaagaa aggctaggaa ggttaggttt tagttggtgt     2580
tttctgttat tgtattggtg ctgcagttat atttattttta gcgtgtcatt tgtgtgataa     2640
aaggtttgtg ctttataata tttattttat attatttatt caatattgag tttgattcaa     2700
tattttctta gctaactgta tttttgccat gcttatggtc ttttattttt tgtgttctta     2760
taactattat aatgctgttc agaattc                                         2787

<210> SEQ ID NO 20
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 20
gcggccaggt tcaggctgtt acaaacttac                                            30

<210> SEQ ID NO 21
<211> LENGTH: 157
<212> TYPE: DNA
<213> ORGANISM: Oryzias latipes

<400> SEQUENCE: 21
cagtagcggt tctaggcacg ggccgtccgg gcggtggcct ggggcggaaa actgaagggg           60
ggcggcaccg gcggctcagc cctttgtaat atattaatat gcaccactat tggtttactt          120
atgtcacagt ttgtaagttt gtaacagcct gaacctg                                   157

<210> SEQ ID NO 22
<211> LENGTH: 106
<212> TYPE: DNA
<213> ORGANISM: Oryzias latipes

<400> SEQUENCE: 22
acatttcagt tgacgaagac aaacaaagtt ctgttgtgac tatggggggg ggggcgcct           60 ggggatggtc tcgcccgggg agtaattcag ggtagaaccg ccactg                         106

<210> SEQ ID NO 23
<211> LENGTH: 90
<212> TYPE: PRT
<213> ORGANISM: Oryzias latipes

<400> SEQUENCE: 23

Glu Leu Val Gln Glu Ile Lys Asn Leu Pro Asn Leu Pro Ser Thr Thr
1               5                   10                  15

Pro Ser Leu Leu Glu Leu Ile Ser Phe Met Ser Asp Lys Asp Leu Ser
            20                  25                  30

Glu Ile Tyr Pro Asn Phe Trp Thr Ala Leu Arg Ile Ala Leu Thr Leu
        35                  40                  45

Pro Val Thr Val Ala Gln Ala Glu Arg Ser Phe Ser Lys Leu Lys Leu
    50                  55                  60

Ile Lys Ser Tyr Leu Arg Ser Thr Met Ser Gln Glu Arg Leu Thr Asn
65                  70                  75                  80

Leu Ala Val Val Ser Ile Asn His Ser Val
                85                  90

<210> SEQ ID NO 24
<211> LENGTH: 92
<212> TYPE: PRT
<213> ORGANISM: Arabidopsis thaliana

<400> SEQUENCE: 24

Asp Gly Asn His Leu Phe Leu Glu Leu Lys Val Leu Lys Glu Leu Leu
1               5                   10                  15

Pro Thr Glu Ile Thr Lys Ala Ile Glu Val Leu Asn Phe Leu Lys Lys
            20                  25                  30

Phe Glu Gly Cys Tyr Pro Asn Thr Trp Ile Ala Phe Arg Val Met Leu
        35                  40                  45

Thr Val Pro Val Ser Val Ala Ser Ala Glu Arg Ser Phe Ser Lys Leu
    50                  55                  60
```

Lys Leu Ile Lys Ser Tyr Ser Arg Ser Thr Met Ser Glu Glu Arg Leu
65                  70                  75                  80

Asn Ala Leu Ala Ile Leu Ser Ile Glu Arg Asp Leu
                85                  90

<210> SEQ ID NO 25
<211> LENGTH: 92
<212> TYPE: PRT
<213> ORGANISM: Arabidopsis thaliana

<400> SEQUENCE: 25

Asp Gly Ala Asp Leu Phe Met Glu Leu Lys Val Leu Arg Glu Val Leu
1               5                   10                  15

Pro Asn Glu Val Thr Lys Pro Ile Lys Val Leu Asp Phe Leu Lys Arg
            20                  25                  30

Val Glu Gly Cys Tyr Pro Asn Thr Trp Ile Ser Phe Arg Ile Leu Leu
        35                  40                  45

Thr Ile Leu Val Ser Val Ala Ser Glu Arg Ser Phe Ser Lys Leu
    50                  55                  60

Lys Leu Ile Lys Asn Tyr Leu Arg Ser Thr Met Ser Gln Asp Arg Leu
65                  70                  75                  80

Asn Gly Leu Ala Ile Leu Ser Ile Glu Arg Ala Met
                85                  90

<210> SEQ ID NO 26
<211> LENGTH: 92
<212> TYPE: PRT
<213> ORGANISM: Arabidopsis thaliana

<400> SEQUENCE: 26

Leu Ala Ser Asp Leu Phe Tyr Glu Leu Lys Ile Leu Arg Glu Ala Leu
1               5                   10                  15

Pro Lys Glu Val Arg Arg Pro Ile Glu Val Leu Asp Phe Leu Gln Lys
            20                  25                  30

Val Glu Gly Cys Tyr Pro Asn Ser Trp Ile Ala Tyr Gln Val Leu Leu
        35                  40                  45

Thr Ile Pro Val Ser Val Ala Ser Ala Glu Arg Ser Phe Ser Lys Leu
    50                  55                  60

Lys Leu Ile Lys Ser Tyr Leu Arg Ser Ser Met Ser Gln Glu Arg Leu
65                  70                  75                  80

Ser Asp Leu Ala Ile Leu Ser Ile Glu Arg Ala Leu
                85                  90

<210> SEQ ID NO 27
<211> LENGTH: 92
<212> TYPE: PRT
<213> ORGANISM: Arabidopsis thaliana

<400> SEQUENCE: 27

Asp Gly Glu Asp Leu Phe Met Glu Leu Lys Leu Leu Lys Asp Val Leu
1               5                   10                  15

Pro Lys Glu Ile Thr Lys Pro Val Glu Val Leu Asp Phe Leu Lys Arg
            20                  25                  30

Met Asp Gly Cys Tyr Pro Asn Thr Trp Ile Thr Tyr Arg Ile Leu Leu
        35                  40                  45

Thr Ile Pro Val Ser Ile Ala Ser Ala Glu Arg Thr Phe Pro Lys Leu
    50                  55                  60

Lys Leu Ile Lys Asn Tyr Leu Arg Ser Thr Val Pro Gln Glu Arg Leu

```
                 65                  70                  75                  80
Asn Gly Leu Ala Leu Ile Ser Ile Glu Gln Glu Leu
                 85                  90
```

<210> SEQ ID NO 28
<211> LENGTH: 91
<212> TYPE: PRT
<213> ORGANISM: Oryza sativa

<400> SEQUENCE: 28

```
Asp Ala Thr Glu Leu His Val Glu Leu Ile Phe Leu Gln Ser Phe Ile
1               5                  10                  15

Ser Gln Glu Lys Leu Gly Pro Val Glu Ile Leu Lys Phe Leu Lys Arg
                20                  25                  30

His Asp Cys Phe Pro Asn Ala Thr Ile Ala Tyr Arg Ile Leu Leu Thr
                35                  40                  45

Ile Pro Val Thr Ile Ala Ser Ala Glu Trp Ser Phe Ser Lys Leu Lys
        50                  55                  60

Leu Leu Lys Ser Tyr Leu Arg Ser Thr Met Ser Gln Glu Arg Leu Asn
65              70                  75                  80

Gly Leu Ala Ile Ile Ala Leu Glu Gly Gly Met
                85                  90
```

<210> SEQ ID NO 29
<211> LENGTH: 90
<212> TYPE: PRT
<213> ORGANISM: Mus musculus

<400> SEQUENCE: 29

```
Phe Tyr Arg Gln Tyr Ala Gly Phe Asn Phe Ile Ala Glu Asp Gly Ser
1               5                  10                  15

Leu Ser Phe Ile Asp Leu Gly Ser Leu Phe Ile Gln His Ala Leu His
                20                  25                  30

Asn Asn Ile Pro Cys Ile Thr Lys Leu Leu His Ile Ala Leu Ser Trp
                35                  40                  45

Pro Ile Thr Ser Ala Asn Asn Glu Lys Ser Phe Ser Thr Leu Ser His
        50                  55                  60

Leu Lys Thr Tyr Leu Leu Arg Thr Met Gly Gln Glu Lys Leu Ser Ser
65              70                  75                  80

Leu Ala Leu Ile Ala Val Glu Gln Glu Leu
                85                  90
```

<210> SEQ ID NO 30
<211> LENGTH: 90
<212> TYPE: PRT
<213> ORGANISM: Homo sapiens

<400> SEQUENCE: 30

```
Phe Tyr Arg His Tyr Ala Lys Leu Asn Phe Val Ile Asp Asp Ser Cys
1               5                  10                  15

Ile Asn Phe Val Ser Leu Gly Cys Leu Phe Ile Gln His Gly Leu His
                20                  25                  30

Ser Asn Ile Pro Cys Leu Ser Lys Leu Leu Tyr Ile Ala Leu Ser Trp
                35                  40                  45

Pro Ile Thr Ser Ala Ser Thr Glu Asn Ser Phe Ser Thr Leu Pro Arg
        50                  55                  60

Leu Lys Thr Tyr Leu Cys Asn Thr Met Gly Gln Glu Lys Leu Thr Gly
65              70                  75                  80
```

```
Pro Ala Leu Met Ala Val Glu Gln Glu Leu
            85              90
```

<210> SEQ ID NO 31
<211> LENGTH: 95
<212> TYPE: PRT
<213> ORGANISM: Ipomoea purpurea

<400> SEQUENCE: 31

```
Gln Leu Arg Val Gln Leu Glu His Phe Glu His Val Gln Gln Leu Pro
1               5                   10                  15

Asp Phe Arg Thr Leu Glu Ser Ile Ser Asp Leu Cys Arg Trp Leu Val
            20                  25                  30

Lys Thr Arg Lys Ser Asn Ile Tyr Pro Leu Val Phe Arg Val Val Thr
        35                  40                  45

Leu Val Leu Thr Leu Pro Val Ser Thr Ala Thr Thr Glu Arg Ser Phe
    50                  55                  60

Ser Ala Met Asn Ile Val Lys Thr Thr Leu Arg Asn Lys Met Glu Asp
65                  70                  75                  80

Glu Phe Leu Ser Asp Cys Leu Leu Val Tyr Ile Glu Lys Gln Ile
                85                  90                  95
```

<210> SEQ ID NO 32
<211> LENGTH: 95
<212> TYPE: PRT
<213> ORGANISM: Oryza sativa

<400> SEQUENCE: 32

```
Leu Glu Met Gln Leu Gly Thr Phe Ile Asp Asp Met Arg Arg Asp Glu
1               5                   10                  15

Arg Phe Lys Gly Leu Glu Thr Leu Ala Glu Leu Ser Ile Lys Leu Val
            20                  25                  30

Glu Thr Asn Lys His Val Leu Tyr Asp Trp Val Tyr Leu Leu Leu Lys
        35                  40                  45

Leu Val Leu Ile Leu Pro Val Ala Thr Ala Ser Val Glu Arg Val Phe
    50                  55                  60

Ser Ala Leu Ser Val Val Lys Ser Lys Leu Arg Asn Ser Met Cys Asp
65                  70                  75                  80

Lys Leu Leu Asn Asp Cys Leu Ile Thr Phe Ile Glu Arg Asp Val
                85                  90                  95
```

<210> SEQ ID NO 33
<211> LENGTH: 96
<212> TYPE: PRT
<213> ORGANISM: Homo sapiens

<400> SEQUENCE: 33

```
Asn Pro Asp Thr Leu Ser Ala Glu Leu His Cys Trp Arg Ile Lys Trp
1               5                   10                  15

Lys His Arg Gly Lys Asp Ile Glu Leu Pro Ser Thr Ile Tyr Glu Ala
            20                  25                  30

Leu His Leu Pro Asp Ile Lys Phe Phe Pro Asn Val Tyr Ala Leu Leu
        35                  40                  45

Lys Val Leu Cys Ile Leu Pro Val Met Lys Val Glu Asn Glu Arg Tyr
    50                  55                  60

Glu Asn Gly Arg Lys Arg Leu Lys Ala Tyr Leu Arg Asn Thr Leu Thr
65                  70                  75                  80

Asp Gln Arg Ser Ser Asn Leu Ala Leu Leu Asn Ile Asn Phe Asp Ile
                85                  90                  95
```

<210> SEQ ID NO 34
<211> LENGTH: 81
<212> TYPE: PRT
<213> ORGANISM: Caenorhabditis elegans

<400> SEQUENCE: 34

Glu Leu Glu Arg Trp Ile Ser Glu Pro Asn Ile Ala Phe Glu Glu Pro
1               5                   10                  15

Ile Val Phe Trp Gln Lys Ala Glu Asn Arg Thr Arg Tyr Pro Leu Leu
            20                  25                  30

Phe Gln Leu Ser Ser Ile Val Leu Cys Leu Pro Gly Ala Leu Leu Asn
        35                  40                  45

Thr Glu Asn Leu Thr Ser Ala Lys Asn Leu Leu Phe Glu His Gln Ile
    50                  55                  60

Gly Cys Glu Asp Gln Thr Asn Gln Lys Ile Leu Phe Leu His Gln Asn
65                  70                  75                  80

Met

<210> SEQ ID NO 35
<211> LENGTH: 88
<212> TYPE: PRT
<213> ORGANISM: Arabidopsis thaliana

<400> SEQUENCE: 35

Glu Leu Val Lys Tyr Leu Lys Asp Glu Leu His Val Thr Thr Glu Asn
1               5                   10                  15

Ser Leu Gly Leu Pro Phe Asp Leu Leu Asp Trp Trp Lys Thr Asn Ser
            20                  25                  30

Ser Lys Tyr Pro Ile Met Ser Leu Met Ala Arg Glu Val Leu Ala Ile
        35                  40                  45

Pro Val Ser Ser Val Ala Ser Glu Ser Ala Phe Ser Thr Gly Gly Arg
    50                  55                  60

Ile Leu Asp Gln Tyr Arg Ser Cys Leu Thr Pro Asp Met Val Glu Ala
65                  70                  75                  80

Leu Val Leu Thr Gln Asp Trp Leu
                85

<210> SEQ ID NO 36
<211> LENGTH: 81
<212> TYPE: PRT
<213> ORGANISM: Arabidopsis thaliana

<400> SEQUENCE: 36

Glu Leu Thr Gln Tyr Leu Ser Glu Ser Ile Val Pro Met Gln Thr Asp
1               5                   10                  15

Val Leu Asp Trp Trp Lys Val Asn Ser Gly Arg Tyr Pro Arg Leu Ser
            20                  25                  30

Asn Met Ala Arg Asp Phe Leu Ala Val Gln Ala Thr Ser Ala Ala Pro
        35                  40                  45

Glu Glu Ile Phe Cys Gly Lys Gly Glu Glu Ile Asp Lys Gln Lys Tyr
    50                  55                  60

Cys Met Pro His Asp Ser Thr Gln Ser Val Ile Cys Ile Arg Ser Trp
65                  70                  75                  80

Ile

<210> SEQ ID NO 37
<211> LENGTH: 84

```
<212> TYPE: PRT
<213> ORGANISM: Tolypocladium inflatum

<400> SEQUENCE: 37

Glu Tyr Glu Arg Tyr Ile Gln Thr Phe Thr His Ala Asp Asp Lys Tyr
1               5                   10                  15

Gln Phe Arg Pro Leu Ser Trp Trp Gln Glu His Glu Met Glu Tyr Pro
                20                  25                  30

Asn Leu Cys Arg Met Ala Thr Asp Leu Leu Ser Ile Pro Thr Met Ser
            35                  40                  45

Ala Glu Thr Glu Arg Ser Phe Ser Ser Ala Gly Lys Met Val Ser Pro
        50                  55                  60

Leu Arg Thr Arg Leu Asp Arg His Thr Ile Gly Met Ala Gln Gly Met
65                  70                  75                  80

Arg Ser Trp Ser

<210> SEQ ID NO 38
<211> LENGTH: 86
<212> TYPE: PRT
<213> ORGANISM: Arabidopsis thaliana

<400> SEQUENCE: 38

Thr Leu Glu Ile Tyr Leu Asp Asp Glu Pro Arg Leu Glu Met Lys Thr
1               5                   10                  15

Phe Ser Asp Met Glu Ile Leu Ser Phe Trp Lys Glu Asn Gln His Arg
                20                  25                  30

Tyr Gly Asp Leu Ala Ser Met Ala Ser Asp Leu Leu Ser Ile Pro Ile
            35                  40                  45

Thr Thr Val Ala Ser Glu Ser Ala Phe Ser Val Gly Gly Arg Val Leu
        50                  55                  60

Asn Pro Phe Arg Asn Arg Leu Leu Pro Gln Val Gln Ala Leu Ile
65                  70                  75                  80

Cys Thr Arg Asn Trp Leu
                85

<210> SEQ ID NO 39
<211> LENGTH: 83
<212> TYPE: PRT
<213> ORGANISM: Zea mays

<400> SEQUENCE: 39

Glu Leu Asp Lys Tyr Met Ser Glu Pro Leu Lys His Ser Gly Gln
1               5                   10                  15

Phe Asp Ile Leu Ser Trp Trp Arg Gly Arg Val Ala Glu Tyr Pro Ile
                20                  25                  30

Leu Thr Gln Ile Ala Arg Asp Val Leu Ala Ile Gln Val Ser Thr Val
            35                  40                  45

Ala Ser Glu Ser Ala Phe Ser Ala Gly Gly Arg Val Val Asp Pro Tyr
        50                  55                  60

Arg Asn Arg Leu Gly Ser Glu Ile Val Glu Ala Leu Ile Cys Thr Lys
65                  70                  75                  80

Asp Trp Val

<210> SEQ ID NO 40
<211> LENGTH: 83
<212> TYPE: PRT
<213> ORGANISM: Arabidopsis thaliana

<400> SEQUENCE: 40
```

```
Glu Leu Asp Gln Tyr Leu Asp Glu Thr Leu Leu Pro Arg Val Gln Glu
1               5                   10                  15

Phe Asp Val Leu Asp Trp Trp Lys Gln Asn Lys Leu Lys Tyr Pro Thr
            20                  25                  30

Leu Ser Lys Met Ala Arg Asp Ile Leu Ser Ile Pro Val Ser Ala Ala
        35                  40                  45

Ala Phe Asp Tyr Val Phe Asp Met Gly Pro Arg Glu Met Asp Glu Tyr
    50                  55                  60

Lys Thr Ser Leu Arg Pro Glu Thr Val Glu Ala Leu Ile Cys Ala Arg
65                  70                  75                  80

Glu Trp Leu
```

<210> SEQ ID NO 41
<211> LENGTH: 83
<212> TYPE: PRT
<213> ORGANISM: Oryza sativa

<400> SEQUENCE: 41

```
Thr Ile Arg Lys Asp Ile Leu Glu Pro Asn Leu Pro Pro Arg Gln Glu
1               5                   10                  15

Leu Asp Ile Ile Asn Trp Trp Lys Phe Ala Trp Ile Lys Tyr Pro Thr
            20                  25                  30

Met Gln Lys Ile Ala Arg Asp Ile Met Thr Ile Leu Val Thr Thr Val
        35                  40                  45

Ala Ser Thr Ser Thr Phe Ser Thr Ser Gly Arg Thr Ile Ser Pro His
    50                  55                  60

Arg Ser Arg Leu Thr Pro Lys Met Ala Glu Ala Leu Thr Cys Met Gln
65                  70                  75                  80

Gly Trp Ser
```

<210> SEQ ID NO 42
<211> LENGTH: 82
<212> TYPE: PRT
<213> ORGANISM: Musca domestica

<400> SEQUENCE: 42

```
Glu Phe Glu Phe Tyr Arg Lys Glu Ile Val Ile Leu Ser Glu Asp Phe
1               5                   10                  15

Lys Val Met Glu Trp Trp Asn Leu Asn Ser Lys Lys Tyr Pro Lys Leu
            20                  25                  30

Ser Lys Leu Ala Leu Ser Leu Leu Ser Ile Pro Ala Ser Ser Ala Ala
        35                  40                  45

Ser Glu Arg Thr Phe Ser Leu Ala Gly Asn Ile Ile Thr Glu Lys Arg
    50                  55                  60

Asn Arg Ile Gly Gln Gln Thr Val Asp Ser Leu Leu Phe Leu Asn Ser
65                  70                  75                  80

Phe Tyr
```

<210> SEQ ID NO 43
<211> LENGTH: 82
<212> TYPE: PRT
<213> ORGANISM: Lucilia cuprina

<400> SEQUENCE: 43

```
Glu Val Asn Arg Tyr Ser Tyr Leu Lys Ile Asn Phe Asp Val Lys Phe
1               5                   10                  15

Lys Val Leu Gln Leu Trp Glu Ser His Ser Ser Glu Tyr Pro Arg Leu
```

-continued

```
                    20                  25                  30
Tyr Lys Phe Ala Gln Lys Ile Leu Ala Ile Pro Ala Ser Ser Ala Ala
            35                  40                  45

Ser Glu Arg Val Phe Ser Ala Ala Gly Asn Ile Ile Thr Glu Lys Arg
    50                  55                  60

Asn Arg Ile Gly Pro Lys Thr Val Asn Asn Leu Leu Phe Leu Asn Ser
65                  70                  75                  80

Leu Cys

<210> SEQ ID NO 44
<211> LENGTH: 83
<212> TYPE: PRT
<213> ORGANISM: Fusarium oxysporum

<400> SEQUENCE: 44

Glu Leu Asp Glu Phe Met Ala Arg Ala Asn Arg Ala Asp Val Glu Val
1               5                   10                  15

Glu Asp Pro Leu Glu Trp Trp Val Cys His Ala Ser Asp Tyr Pro Ile
            20                  25                  30

Leu Ser Lys Met Ala Phe Asp Leu Phe Ser Cys Pro Ala Met Ser Ala
        35                  40                  45

Glu Cys Glu Arg Val Phe Ser Gln Thr Lys Lys Val Ile Thr Asp Glu
    50                  55                  60

Arg Asn Arg Leu Lys Ser Asp Thr Val Ala Ala Leu Glu Cys Gln Lys
65                  70                  75                  80

His Leu Leu

<210> SEQ ID NO 45
<211> LENGTH: 82
<212> TYPE: PRT
<213> ORGANISM: Bactrocera tryoni

<400> SEQUENCE: 45

Glu Val Glu Arg Tyr Ser Arg Glu Val Glu Met Thr Gly Asn Phe
1               5                   10                  15

Asn Leu Met Glu Trp Trp Gln Ser Asn Gln Ser Lys Tyr Pro His Leu
            20                  25                  30

Ser Lys Phe Ala Leu Gln Ile His Ala Ile Pro Ala Ser Ser Ala Ala
        35                  40                  45

Ala Glu Arg Ser Phe Ser Leu Ala Gly Asn Leu Ile Thr Glu Lys Arg
    50                  55                  60

Asn Arg Ile Ala Pro Gly Ser Val Asp Ser Leu Leu Phe Leu Asn Thr
65                  70                  75                  80

Tyr Tyr

<210> SEQ ID NO 46
<211> LENGTH: 85
<212> TYPE: PRT
<213> ORGANISM: Arabidopsis thaliana

<400> SEQUENCE: 46

Glu Leu Asp Ile Tyr Leu Gly Glu Pro Thr Leu Asp Met Ala Ala Phe
1               5                   10                  15

Arg His Phe Asn Val Leu Ala Tyr Trp Lys Asp Asn Ser Cys Arg Phe
            20                  25                  30

Lys Glu Leu Ser Ser Met Ala Cys Asp Val Leu Ser Ile Pro Ile Thr
        35                  40                  45
```

```
Thr Val Ala Ser Glu Ser Ser Phe Ser Ile Gly Ser Gly Val Leu Ser
    50                  55                  60

Lys Tyr Arg Ser Ser Leu Leu Pro Glu Asn Ile Gln Ala Leu Ile Cys
 65                  70                  75                  80

Thr Arg Asn Trp Leu
                85

<210> SEQ ID NO 47
<211> LENGTH: 85
<212> TYPE: PRT
<213> ORGANISM: Arabidopsis thaliana

<400> SEQUENCE: 47

Asn Leu Gln Asn Tyr Leu Asp Asp Pro Arg Leu Asp Leu Arg Ser Phe
 1               5                  10                  15

Thr Asp Met Glu Val Leu Ser Tyr Trp Lys Gly Asp Gly Gln Arg Tyr
                20                  25                  30

Gly Asp Leu Ala Ser Leu Ala Ser Ala Ile Leu Ser Ile Pro Ile Thr
            35                  40                  45

Thr Val Ala Ala Glu Ser Ser Phe Ser Ile Gly Gly Arg Ile Leu Asn
    50                  55                  60

Pro Phe Arg Asn Arg Leu Leu Ser Arg Asn Val Gln Ala Leu Leu Cys
 65                  70                  75                  80

Thr Arg Asn Trp Leu
                85

<210> SEQ ID NO 48
<211> LENGTH: 83
<212> TYPE: PRT
<213> ORGANISM: Oryza sativa

<400> SEQUENCE: 48

Glu Val Asp Lys Tyr Leu Ser Glu Asp Asn Glu Pro Asp Thr Pro Lys
 1               5                  10                  15

Phe Asp Ile Leu Lys Trp Trp Lys Ala Asn Ser Thr Arg Phe Pro Ile
                20                  25                  30

Leu Ser His Leu Ala Cys Asp Leu Leu Ala Ile Pro Ile Thr Ser Val
            35                  40                  45

Ala Ser Glu Ser Ala Phe Ser Ala Gly Gly Arg Thr Leu Asp Asp Phe
    50                  55                  60

Arg Thr Ser Leu Thr Pro Arg Met Val Glu Arg Leu Val Cys Ala Asn
 65                  70                  75                  80

Asp Trp Leu

<210> SEQ ID NO 49
<211> LENGTH: 87
<212> TYPE: PRT
<213> ORGANISM: Arabidopsis thaliana

<400> SEQUENCE: 49

Glu Leu Asp Ile Tyr Leu Lys Ala Glu Val Asn Pro Lys Thr Leu
 1               5                  10                  15

Pro Gly Met Glu Trp Asp Val Leu Ser Trp Trp Arg Leu Asn Ser Gln
                20                  25                  30

Lys Tyr Pro Val Leu Ser Glu Ile Ala Arg Asp Val Leu Ala Met Gln
            35                  40                  45

Val Ser Ser Val Ala Ser Glu Ser Ala Phe Ser Thr Ser Gly Arg Leu
    50                  55                  60
```

```
Leu Glu Pro Ser Arg Ser Cys Leu Thr His Tyr Met Val Glu Thr Leu
 65                  70                  75                  80

Val Cys Leu Glu Gln Trp Leu
                 85
```

<210> SEQ ID NO 50
<211> LENGTH: 83
<212> TYPE: PRT
<213> ORGANISM: Arabidopsis thaliana

<400> SEQUENCE: 50

```
Glu Leu Asp Gln Tyr Leu Glu Ser Leu Ile Pro Arg Ser Gln Asp
  1               5                  10                  15

Phe Glu Val Leu Gly Trp Trp Ser Leu Asn Arg Thr Lys Tyr Pro Thr
                 20                  25                  30

Leu Ser Lys Met Ala Ala Asp Val Leu Ser Val Pro Phe Cys Thr Val
                 35                  40                  45

Ser Pro Asp Ser Val Phe Asp Thr Glu Val Lys Lys Met Asp Asn Tyr
             50                  55                  60

Arg Ser Ser Leu Arg His Val Thr Leu Glu Ala Leu Phe Cys Ala Lys
 65                  70                  75                  80

Asp Trp Phe
```

<210> SEQ ID NO 51
<211> LENGTH: 81
<212> TYPE: PRT
<213> ORGANISM: Bactrocera dorsalis

<400> SEQUENCE: 51

```
Ser Leu Glu Gln Tyr Leu Arg Gln Asp Phe Val Glu Arg His Gln Asn
  1               5                  10                  15

Pro Leu Asn Tyr Trp Asp Ser Lys Lys Ala Thr Phe Pro Glu Leu Tyr
                 20                  25                  30

Glu Leu Ser Asn Lys Tyr Leu Cys Ile Pro Ala Thr Ser Val Pro Ser
                 35                  40                  45

Glu Arg Val Phe Ser Lys Ala Gly Gln Ile Ile Asn Asp Arg Arg Asn
             50                  55                  60

Arg Leu Lys Gly Glu Lys Leu Asp Gln Ile Met Phe Leu Asn Ser Asn
 65                  70                  75                  80

Phe
```

<210> SEQ ID NO 52
<211> LENGTH: 80
<212> TYPE: PRT
<213> ORGANISM: Ascobolus immersus

<400> SEQUENCE: 52

```
Glu Leu Glu Ala Phe Leu Ser Glu Pro Cys Gln Lys Val Pro Asn Pro
  1               5                  10                  15

Val Glu Trp Trp Ile Val Asn Gln Asp Arg Phe Pro Leu Leu Ser Lys
                 20                  25                  30

Leu Ala Leu Asn Ile Leu Ser Ile Pro Ala Met Ser Ala Glu Cys Glu
                 35                  40                  45

Arg Val Phe Ser Asn Ala Lys Leu Ile Leu Thr Glu Arg Arg Arg Thr
             50                  55                  60

Ile Gly Asp Glu Ala Leu Glu Ala Asn Gln Val Leu Arg Ala Trp Ile
 65                  70                  75                  80
```

```
<210> SEQ ID NO 53
<211> LENGTH: 81
<212> TYPE: PRT
<213> ORGANISM: Homo sapiens

<400> SEQUENCE: 53

Glu Leu Ser Asn Phe Lys Ser Gln Lys Val Leu Gly Leu Asn Glu Asp
1               5                   10                  15

Pro Leu Lys Trp Trp Ser Asp Arg Leu Ala Leu Phe Pro Leu Leu Pro
            20                  25                  30

Lys Val Leu Gln Lys Tyr Trp Cys Val Thr Ala Thr Arg Val Ala Pro
        35                  40                  45

Glu Arg Leu Phe Gly Ser Ala Ala Asn Val Val Ser Ala Lys Arg Asn
    50                  55                  60

Arg Leu Ala Pro Ala His Val Asp Glu Gln Val Phe Leu Tyr Glu Asn
65                  70                  75                  80

Ala

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cttgcatggt ctcctttagc cagtagcg                                            28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cgccactgcc tttagcagac attcactg                                            28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agggaaacca ttccaaaccc cagtagcg                                            28

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cgccactgcc aaacccatg ctttaacc                                             28

<210> SEQ ID NO 58
<211> LENGTH: 28
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 58
gggtcagtct tattcttggg cagtagcg                                        28

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cgccactgtt cttgggcaaa gggagaat                                        28

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
cttacgagag cgctcataca cagtagcg                                        28

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cgccactgct catacagctc acttcata                                        28

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
aaggcattgg atcccattac cagtagcg                                        28

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cgccactgcc cattacagat ggttgtga                                        28

<210> SEQ ID NO 64
<211> LENGTH: 28
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 64
ctagcctgaa ggaccagggg cagtagcg                                            28

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cgccactgac cagggcttg aaaggtgg                                             28

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gcctgcttct gcctcccgag cagtagcg                                            28

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cgccactgct cccgagtgct ggggtcaa                                            28

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
acaacgtcgt gactgggaaa cagtagcg                                            28

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cgccactgct gggaaaaccc tggcgtta                                            28

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70 tggtttttttt cccctgttta cagtagcg                                      28

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cgccactgcc tgtttaggat agcttgct                                       28

<210> SEQ ID NO 72
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
tgtgagcgga taacaatttc acacaggaaa cagctatgac catgattacg ccaagcttgc    60
atggtccctt tagccagtag cggttctagg cacgggccgt ccgggcggtg gc           112

<210> SEQ ID NO 73
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atctgactgt ttaatacaca catacccatc cgaaggtcct tagaaaccaa gcaatttagc    60
ctcacagtaa gaatcagtag cggttctagg cacgggccgt ccgggcggtg gc           112

<210> SEQ ID NO 74
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
actatctatg tttagtactc tgctatacat gtaaacaaac actgtgataa atgtttatgt    60 cattttagc acttcagtag cggttctagg cacgggccgt ccgggcggtg gc            112

<210> SEQ ID NO 75
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gggatggtct cgcccgggat tcagggtaga accgccactg cctttagcga cattcactgg    60
ccgtcgtttt acaacgtcgt gactgggaaa accctggcgt tacccaactt aatc         114

<210> SEQ ID NO 76

```
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
gggatggtct cgcccgggat tcagggtaga accgccactg gtaagaattt acagacggtg      60
aagagtcagg gtttatttat ttacatctaa agtattttgc gtggcacctg cctc           114

<210> SEQ ID NO 77
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gggatggtct cgcccgggat tcagggtaga accgccactg tagcacttgc agaatagtat      60
ataattatgc ttaagcaatc tcttatactt aggttttcaa attctcagtg ggaa            114

<210> SEQ ID NO 78
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tgtggaattg tgagcggata acaatttcac acaggaaaca gctatgacca tgattacgcc      60
aagcttgcat ggtccctta gccagtagc                                        89

<210> SEQ ID NO 79
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
atggtctcgc ccggggagta attcagggta gaaccgccac tgcctttagc gacattca       58

<210> SEQ ID NO 80
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgtggaattg tgagcggata acaatttcac acaggaaaca gctatgacca tgattacgcc      60
aagcttgcat ggtccctta g                                                81

<210> SEQ ID NO 81
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 81
gctttagcga cattca                                                    16

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctttagcgac attca                                                     15

<210> SEQ ID NO 83
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
tgtggaattg tgagcggata acaatttcac acaggaaaca gctatgacca tgattacgcc    60
aagcttgcat ggtcccttt                                                 79

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tagcgacatt ca                                                        12

<210> SEQ ID NO 85
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tgtggaattg tgagcggata acaatttcac acaggaaaca gctatgacca tgattacgcc    60
aagcttgcat ggtcccctt                                                 78

<210> SEQ ID NO 86
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgtggaattg tgagcggata acaatttcac acaggaaaca gctatgacca tgattacgcc    60
aagcttgcat ggtccctg                                                  78

<210> SEQ ID NO 87
<211> LENGTH: 77
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 87
tgtggaattg tgagcggata acaatttcac acaggaaaca gctatgacca tgattacgcc       60
aagcttgcat ggtccct                                                     77

<210> SEQ ID NO 88
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tgtggaattg tgagcggata acaatttcac acaggaaaca gctatgacca tgattacgcc       60
aagcttgcat ggtccc                                                      76

<210> SEQ ID NO 89
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctttagcgac attca                                                       15

<210> SEQ ID NO 90
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gtctcgcccg gggagtaatt cagggtagaa ccgccactgc ctttagcgac attca            55

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tcgatgacag ggagcgctgg cctttagcca gtagcggttc                            40

<210> SEQ ID NO 92
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tcgatgacag ggagcgctgg cctttagcta aagctaaagg ctttagcttt cttcaaccgg       60
acgtgtc                                                                67
```

```
<210> SEQ ID NO 93
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
tcgatgacag ggagcgctgg cctttagcct aaagtgttcg agcccaacgg gccgcagtac    60
cctcacagcg ggatcgatga cagggagcgc tggcctttag gctaaaggct ttagctttct   120
tcaaccggac gtgtc                                                    135

<210> SEQ ID NO 94
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tcgatgacag ggagcgctgg cctttaggct aaaggcttta gctttcttca accggacgtg    60
tc                                                                   62

<210> SEQ ID NO 95
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
ctgtggggcc ctgtctggtc gcgggttctg tgcagacgtc tcggtttcag acgagcccaa    60
cgggccgcag taccctcaca gcgggatcga tgacagggag cgctggcctt tagccagtag   120
cggttctagg cacgggccgt ccgg                                          144

<210> SEQ ID NO 96
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
acgcagtggc tccaggtagt atggaataga ggaatagact ttcttcacac tagtaaaaca    60
atggtagacg tgatggaaaa caagtgtgct cacaacatca cacaattaaa aattcagtag   120
cggttctagg cacgggccgt ccgg                                          144

<210> SEQ ID NO 97
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
aagtgagctg tattaccgat agtaacatgc tatgacaatg aatacgggct gacgatctga    60
tcaagagtgc gggaaatatt gcgagaagga tgccacgcat tggtcacttc gaaacagtag   120
```

```
cggttctagg cacgggccgt ccgg                                            144
```

```
<210> SEQ ID NO 98
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
ggggagtaat tcagggtaga accgccactg cctttagctt tcttcaaccg dacgtgtcgt     60
tgtgcaggaa actatggagg gtttaactgt ggggaatgca gattcggtta ctggggctcc   120
aactgtgctg agtacagaga gtca                                           144
```

```
<210> SEQ ID NO 99
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (106)..(106)
<223> OTHER INFORMATION: a, c, t, g, unknown or other

<400> SEQUENCE: 99
ggggagtaat tcagggtaga accgccactg tctgcgtatt attaattctc gctccgggaa     60
ctatccgaga gatattagca agacaataat acactaaaag tatttnctac gattctcgcg   120
agacgtatga taatataatg gcag                                           144
```

```
<210> SEQ ID NO 100
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
ggggagtaat tcagggtaga accgccactg ctaaggagat agagaataag ggttttatct     60
gaagggtagg caacgcactg gcgtaaacgc tggtgaccgt gggcggcggt gaatcactta   120
ccatcaggtg acccgtcttg ctcg                                           144
```

```
<210> SEQ ID NO 101
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gaaccgccac tgcctttagc tttcttcaac cggacgtgtc                            40
```